US007670778B2

(12) United States Patent
Horvitz et al.

(10) Patent No.: US 7,670,778 B2
(45) Date of Patent: Mar. 2, 2010

(54) **TUMOR SUPPRESSOR PATHWAY IN *C. ELEGANS***

(75) Inventors: H. Robert Horvitz, Auburndale, MA (US); Ewa M. Davison, Somerville, MA (US); Xiaowei Lu, San Francisco, CA (US)

(73) Assignee: Massachusetts Institute of Technolgoy, Cambridge, MA (US)

( * ) Notice: Subject to any disclaimer, the term of this patent is extended or adjusted under 35 U.S.C. 154(b) by 0 days.

(21) Appl. No.: 11/973,006

(22) Filed: Oct. 4, 2007

(65) Prior Publication Data

US 2008/0213777 A1 Sep. 4, 2008

Related U.S. Application Data

(63) Continuation of application No. 10/839,896, filed on May 6, 2004, now abandoned, which is a continuation of application No. 09/872,523, filed on Jun. 1, 2001, now abandoned.

(60) Provisional application No. 60/208,802, filed on Jun. 2, 2000.

(51) Int. Cl.
*C12Q 1/68* (2006.01)

(52) U.S. Cl. ........................... 435/6; 435/7.1; 436/501; 436/518

(58) Field of Classification Search ....................... None
See application file for complete search history.

(56) References Cited

FOREIGN PATENT DOCUMENTS

| | | | |
|---|---|---|---|
| WO | WO 98/54299 | | 12/1998 |
| WO | WO0011168 | * | 3/2000 |
| WO | WO 01/94545 | | 12/2001 |

OTHER PUBLICATIONS

Beitel et al., "The *C. elegans* Gene *lin*-9, which Acts in an Rb-Related Pathway, is Required for Gonadal Sheath Cell Development and Encodes a Novel Protein," *Gene* 254:253-263 (2000).

Ceol and Horvitz, "*dpl-1* DP and *efl-1* E2F Act with *lin-35* Rb to Antagonize Ras Signaling in *C. elegans* Vulval Development," *Mol. Cell* 7:461-473 (2001).

Clark et al., "The *Caenothabditis elegans* Locus *lin-15*, a Negative Regulator of a Tyrosine Kinase Signaling Pathway, Encodes Two Different Proteins," *Genetics* 137:987-997 (1994).

Davison and Horvitz, "Cloning and Characterization of the Class A Synthetic Multivulva Genes," Abstract 263, 12$^{th}$ International *C. elegans* Meeting, Madison, Wisconsin, Jun. 2-6, 1999 (printed on Sep. 27, 2001 from http://elegans.swmed.edu/wli/[wm99p263]).

Doll et al., "Characterization of New Genes Required for the Negative Regulation of Vulval Induction, Including the New Class B synMuv Gene *lin-61*," Abstract 85, East Coast Worm Meeting 2000, Atlanta, Georgia, Jun. 9-11, 2000 (printed on Sep. 27, 2001 from http://elegans.swmed.edu/wli/[ecwm2000p85]).

Fay et al., "The Synthetic Multivulval Genes of *C. elegans*: Functional Redunancy, Ras-Antagonism, and Cell Fate Determination," *Genesis* 26:279-284 (2000).

Ferguson and Horvitz, "The Multivulva Phenotype of Certain *Caenorhabditis elegans* Mutants Results from Defects in Two Functionally Redundant Pathways," *Genetics* 123:109-121 (1989).

GenBank Accession No. C29407 (1996).

GenBank Accession No. C35953 (1996).

GenBank Accession No. C39398 (1996).

GenBank Accession No. C42682 (1996).

GenBank Accession No. C47800 (1996).

GenBank Accession No. AU112450 (2000).

GenBank Accession No. AU116296 (2000).

Horvitz and Sulston, "Isolation and Genetic Characterization of Cell-Lineage Mutants of the Nematode *Caenorhabditis elegans*," *Genetics* 96:435-454 (1980).

Hsieh et al., "The Ring Finger/B-Box Factor TAM-1 and a Retinoblastoma-Like Protein LIN-35 Modulate Context-Dependent Gene Silencing in *Caenorhabditis elegans*," *Genes Dev.* 13:2958-2970 (1999).

Huang et al., "The *lin-15* Locus Encodes Two Negative Regulators of *Caenorhabditis elegans* Vulval Development," *Mol. Biol. Cell* 5:395-412 (1994).

Kim et al., "Construction of a Gorilla Fosmid Library and Its PCR Screening System," *Genomics* 82(5):571-574 (2003), Abstract Only.

NCBI accession No. Z71266 (Apr. 19, 1996).

Lu and Horvitz, "*lin-35* and *lin-53*, Two Genes that Antagonize a *C. elegans* Ras Pathway, Encode Proteins Similar to Rb and Its Binding Protein RbAp48," *Cell* 95:981-991 (1998).

Solari and Ahringer, "NURD-Complex Genes Antagonise Ras-Induced Vulval Development in *Caenorhabditis elegans*," *Curr. Biol.* 10:223-226 (2000).

Stedman's Medical Dictionary, 27$^{th}$ Edition, Definition of "Cosmid," Downloaded from URL>>pdrel.thompsonhc.com on Oct. 28, 2003.

International Search Report for PCT/US01/17909 dated Nov. 30, 2001.

International Preliminary Report on Patentability for PCT/US01/17909 dated Jul. 30, 2002.

* cited by examiner

*Primary Examiner*—Misook Yu
(74) *Attorney, Agent, or Firm*—Clark & Elbing LLP; Kristina Bieker-Brady

(57) ABSTRACT

The invention provides novel lin-8, lin-56, and lin-61 genes and polypeptides involved in cell fate determination and in cell proliferation. In addition, the invention includes mutants of these three genes, as well as methods for utilizing these genes, and their encoded polypeptides, in diagnosing and treating abnormal cell proliferation.

8 Claims, 13 Drawing Sheets

```
                         10        20        30        40
                     ....*....|....*....|....*....|....*....|
consensus          1 FDWEDYL---EETGARAAPVELF---DKQPVDSPPNGFKV 34
lin-61           146 VNYVNNCi-dGEIVGQTSLSPKF---DEGKALLSKHRFKV 181
lin-61            23 YLWESYLhqfEKGKTSFIPVEAF---NRNLTVNFNECVKE 59
lin-61           388 FRWDEYL---EKESAETLPLDLF---KPMPSQERLDKFKV 421
hl(3)mbt         206 WSWESYL---EEQKAITAPVSLFq--DSQAVTHNKNGFKL 240
hl(3)mbt         314 FSWSQYM---CSTRAQAAPKHMF---VSQSHSPPPLGFQV 347
hl(3)mbt         422 FCWEKYL---EETGASAVPTWAF-------KVRPPHSFLV 451
tumor sup(Dm)    819 FRWSEYLk--SKGKDVAAPIHLF----LNPFPISPNCFEI 852
tumor sup(Dm)    926 FSWSRYL---VKTGGKAAPRALFghlNMQQQMDVRNGFAV 962
tumor sup(Dm)   1035 FIWDDYI---SEVGGMAASKELF-------TPRQPMEYQE 1064
scmh1 (mouse)     28 FTWDKYL---KETCSVPAPVHCF----KQSYTPPSNEFKI 60
scml2 (human)    139 SSWPMFLl-kTLNGSEMASATLF---KKEPPKPPLNNFKV 174

                         50        60        70        80
                     ....*....|....*....|....*....|....*....|
consensus         35 -------GMKLEAVDP------RNPSLICVATVVEVKGYR 61
lin-61           182 -------GQRLELLNY------SNSTEIRVARIQEICGRR 208
lin-61            60 -------GVIFETVVHdydkncDSIQVRWFARIEKVCGYR 92
lin-61           422 iliskrvGLRLEAADM------CENQFICPATVKSVHGRL 455
hl(3)mbt         241 -------GMKLEGIDP------QHPSMYFILTVAEVCGYR 267
hl(3)mbt         348 -------GMKLEAVDR------MNPSLVCVASVTDVVDSR 374
hl(3)mbt         452 -------NMKLEAVDR------RNPALIRVASVEDVEDHR 478
tumor sup(Dm)    853 -------GMKLEAIDP------ENCSLFCVCSIVEVRGYR 879
tumor sup(Dm)    963 -------GMHLEAEDL------NDTGKICVATVTDILDER 989
tumor sup(Dm)   1065 -------RMKLEVVDQ------RNPCLIRPATVVTRKGYR 1091
scmh1 (mouse)     61 -------SMKLEAQDP------RNTTSTCIATVVGLTGAR 87
scml2 (human)    175 -------GMKLEAIDK------KNPYLICPATIGDVKGDE 201

                         90       100       110       120
                     ....*....|....*....|....*....|....*....|
consensus         62 LLLHFD----------GWDDR------YDFWCDADSPDIF 85
lin-61           209 MNVSITkkdfpeslpdADDDRqvfssgSQYWIDEGSFFIF 246
lin-61            93 VLAQFI----------GAD--------TKFWLNILSDDMF 114
lin-61           456 INVNFD----------GWDEE------FDELYDVDSHDIL 479
hl(3)mbt         268 LRLHFD----------GYSEC------HDFWVNANSPDIH 291
hl(3)mbt         375 FLVHFD----------NWDDT------YDYWCDPSSPYIH 398
hl(3)mbt         479 IKIHFD----------GWSHG------YDFWIDADHPDIH 502
tumor sup(Dm)    880 LKLSFD----------GYSSM------YDFWVNADSQDIF 903
tumor sup(Dm)    990 IRVHFD----------GWDDC------YDLWVHITSPYIH 1013
tumor sup(Dm)   1092 VQLHLD----------CWPTE------YYFWLEDDSPDLH 1115
scmh1 (mouse)     88 LRLRLD----------GSDNK------NDFWRLVDSSEIQ 111
scml2 (human)    202 VHITFD----------GWSGA------FDYWCKYDSRDIF 225

                        130
                     ....*....|....*
consensus         86 PVGWCEKNGHPLQPP 100
lin-61           249 PVGFAAVNGYQLNAK 263
lin-61           115 GLANAAM-SDPNMDK 128
lin-61           480 PIGWCEAHSYVLQPP 494
hl(3)mbt         292 PAGWFEKTGHKLQLP 306
hl(3)mbt         399 PVGWCQKQGKPLTPP 413
hl(3)mbt         503 PAGWCSKTGHPLQPP 517
tumor sup(Dm)    904 PPGWCDETARVLQAP 918
tumor sup(Dm)   1014 PCGWHEGRQQLIVPP 1028
tumor sup(Dm)   1116 PIGWCEATSHELETP 1130
scmh1 (mouse)    112 PIGNCEKNGGMLQPP 126
scml2 (human)    226 PAGWCRLTGDVLQPP 240
```

Figure 7

TUMOR SUPPRESSOR PATHWAY IN *C. ELEGANS*

CROSS REFERENCE TO RELATED APPLICATIONS

This application is a continuation of, and claims benefit of the filing date of U.S. patent application Ser. No. 10/839,896 filed May 6, 2004 now abandoned, which is a continuation of U.S. patent application Ser. No. 09/872,523, filed Jun. 1, 2001 now abandoned, which claims the benefit of the filing date of U.S. Provisional Application No. 60/208,802, filed Jun. 2, 2000. These applications are hereby incorporated by reference.

STATEMENT AS TO FEDERALLY SPONSORED RESEARCH

The present research was supported by a grant from the National Institutes of Health (Number GM 24663). The U.S. government has certain rights to this invention.

BACKGROUND OF THE INVENTION

The field of the invention is cell proliferation.

The nematode *Caenorhabditis elegans* (*C. elegans*) is well suited for developmental genetic studies because the entire cell lineage has been mapped and is essentially invariant from one animal to the next. Thus, by comparing the cell lineage of a wild-type animal to that of a mutant animal, the changes in cell fates caused by the mutation can be determined.

A number of mutations that alter cell lineage in *C. elegans*, termed lin mutations, were obtained in genetic screens conducted by Horvitz and Sulston in the late 1970's. A subset of the mutations affected the formation of the vulva, a structure on the ventral surface of *C. elegans* hermaphrodites through which eggs are laid and through which sperm enters during cross-fertilization. Six vulval precursor cells have the potential to undertake a vulval cell lineage, as defined by the number and pattern of cell divisions. In a wild-type animal only three of these cells actually undertake vulval cell fates and these three cells generate the 22 cells that make up the adult vulva. In multivulva (Muv) animals, most or all of the six vulval precursor cells undertake vulval cell fates. In addition to the cells required for the formation of a normal vulva, these mutant animals generate an excess of cells which cause the formation of raised, vulva-like structures on the ventral surface of the animal. On the other hand, a vulvaless (Vul) phenotype results when no or too few vulval precursor cells adopt vulval cell fates.

Genetic and molecular analyses of Muv and Vul animals have defined a Ras signal transduction pathway that mediates induction of the hermaphrodite vulva. This pathway includes the LIN-3 EGF-like ligand, the LET-23 receptor tyrosine kinase, the SEM-5 adaptor, LET60 Ras, the KSR-1 kinase, LIN-45 MEK-2, and the MPK-1 MAP kinase, and regulates the activities of the ETS transcription factor LIN-1 and the winged-helix transcription factor LIN-31 (reviewed by Horvitz and Sternberg, Nature 351:535-41, 1991; Sundaram and Han, Bioessays 18:473-480, 1996; Tan et al., Cell 93:569-580, 1998). Mutant animals in which this pathway is ectopically activated can display a Muv phenotype, whereas mutant animals that have reduced Ras pathway signaling can display a Vul phenotype.

The synthetic multivalva (synMuv) genes act in two functionally-redundant pathways as negative regulators of the nematode Ras signaling pathway. The first synthetic multivulva mutant was identified by Horvitz and Sulston. The two genetic loci mutated in this mutant were termed lin-8 and lin-9. Reduction-of-function mutations in both of these loci were required for a multivulva phenotype. Subsequent genetic screens identified a set of loci which fall into the same class as lin-8, termed class A genes, and genes which fall into the same class as lin-9, termed class B genes. In general, an animal with a reduction-of-function mutation in any class A gene and a reduction-of-function mutation in any class B gene will display a multivulva phenotype, while animals carrying one or more mutations of the same class have a wild-type vulval phenotype. These two classes appear to define two functionally redundant pathways that negatively regulate the expression of vulval cell fates.

Thus far at least four class A loci (lin-8, lin-15A, lin-38, and lin-56) and at least fourteen class B loci (lin-9, lin-15B, lin-35, lin-36, lin-37, lin-13, lin-52, lin-53, lin-54, lin-55 (dpl-1), lin-61, hda-1, tam-1 (Hsieh et al., Genes & Dev. 13:2958-2970, 1999), and the *C. elegans* E2F1 homolog (efl-1)) have been identified genetically. lin-15 encodes both A and B activities in two non-overlapping transcripts. In addition, lin-37, lin-35, lin-53, lin-52, lin-54, lin-55 (dpl-1), lin-15A, lin-15B, lin-36, lin-9, lin-55, and efl-1 have been cloned (Ceol and Horvitz, Molecular Cell 7:461-473, 2001; Clark et al., Genetics 137:987-997, 1994; Huang et al., Mol. Biol. Cell 5:395-411, 1994; Beitel et al., Gene 254:253-263, 2000; and PCT WO 98/54299).

A number of the synMuv family members encode polypeptides with sequence similarity to polypeptides involved in cancer development and progression. For example, lin-35 encodes a homolog of the mammalian pocket protein family, which includes retinoblastoma protein (Rb), p107, and p130. This family of proteins has been the subject of intense study since the cloning of Rb in 1986. Rb is a tumor suppressor gene; mutations that inactivate Rb predispose individuals to tumor formation. Most commonly, inactivation of Rb results in a type of eye cancer, retinoblastoma, although inactivating mutations in Rb have been found in other types of tumors. The Rb protein is thought to function as a negative regulator of cell cycle progression. A number of molecules that interact, both directly and indirectly, with Rb and the other pocket proteins have been characterized in mammalian cells.

Another synMuv family member, lin-53, encodes a homolog of p48, a protein which has been shown to bind Rb. Although the functional significance of the interaction between p48 and Rb is not fully understood, recent studies suggest that p48 may play a role in remodeling chromatin structure. In addition, lin-55(dpl-1) encodes a homolog of the DP family of proteins (Ceol and Horvitz, Molecular Cell 7:461-473, 2001). DP family members, together with E2F proteins, bind DNA at specific sites, thereby regulating the transcription of genes that are essential for cell cycle progression. Furthermore, pocket proteins such as Rb bind to the DP-E2F complex to repress transcription.

As in the nematode, Ras pathways have been found to control cell proliferation in a range of organisms from the yeast *Saccharomyces cerevisiae* to humans. The Ras pathway defines one class of oncogene signaling pathways; members of this pathway, most commonly Ras itself, have been shown to be mutated in a broad range of human cancers (Hunter, Cell 88:333-346, 1997). Accordingly, analysis of the Ras pathway, in particular the vulval induction pathway, in *C. elegans* addresses the significant need of increasing our understanding of cancer in general.

SUMMARY OF THE INVENTION

We isolated and cloned three novel *C. elegans* genes, lin-8, lin-56, and lin-61, that are part of two synMuv pathways and we characterized several mutations in these genes. lin-8, lin-56, and lin 61 genes, their mutants, and the proteins they encode, may be used in genetic and biochemical model systems to further our understanding of cell proliferative diseases, including cancer, as well as in diagnosing and treating cell proliferative diseases.

Accordingly, the first aspect of the invention features a substantially pure nucleic acid encoding a LIN-8 polypeptide, where the LIN-8 polypeptide includes at least 130 contiguous amino acids of SEQ ID NO: 1 and modulates cell proliferation. In a preferred embodiment of this aspect of the invention, the amino acid sequence of the LIN-8 polypeptide includes SEQ ID NO:1, and in another embodiment, the LIN-8 polypeptide has an amino acid alteration relative to the sequence of SEQ ID NO:1, for example, one that increases cell proliferation.

In other preferred embodiments of this aspect, the polynucleotide sequence of the nucleic acid includes SEQ ID NO:2, or at least 400 contiguous nucleotides of SEQ ID NO:2. In addition, the polynucleotide sequence of the nucleic acid may include a mutant lin-8 nucleic acid sequence, for example, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, or SEQ ID NO:46.

A second aspect of the invention features a polypeptide having an amino acid sequence identical to any one of SEQ ID NO:17, SEQ ID NO:19, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or SEQ ID NO:47.

In a third aspect, the invention encompasses a substantially pure nucleic acid encoding a LIN-56 polypeptide, where the LIN-56 polypeptide includes at least 110 contiguous amino acids of SEQ ID NO:3 and modulates cell proliferation. In addition, the amino acid sequence of the LIN-56 polypeptide may be SEQ ID NO:3. In a preferred embodiment of this aspect of the invention, the LIN-56 polypeptide has an amino acid alteration relative to the sequence of SEQ ID NO:3, for example, one that increases cell proliferation.

In additional embodiments of this aspect of the invention, the polynucleotide sequence of the nucleic acid includes SEQ ID NO:4, or at least 400 contiguous nucleotides of SEQ ID NO:4. Furthermore, the polynucleotide sequence of the nucleic acid may be a mutant lin-56 nucleic acid sequence, such as SEQ ID NO:48.

A fourth aspect of the invention features a substantially pure nucleic acid encoding a LIN-61 polypeptide, where the LIN-61 polypeptide includes at least 130 contiguous amino acids of SEQ ID NO:5 and modulates cell proliferation. In preferred embodiments of this aspect, the amino acid sequence of the LIN-61 polypeptide may be SEQ ID NO:5, or the LIN-61 polypeptide has an amino acid alteration relative to the sequence of SEQ ID NO:5, for example, one that increases cell proliferation.

In another embodiment of this aspect of the invention, the polynucleotide sequence of the nucleic acid may be SEQ ID NO:6, or it may include at least 400 contiguous nucleotides of SEQ ID NO:6. Furthermore, the polynucleotide sequence of the nucleic acid may be a mutant lin-61 nucleic acid sequence, for example, one having the sequence of SEQ ID NO:73, SEQ ID NO:74, SEQ ID NO:75, or SEQ ID NO:78.

A fifth aspect of the invention encompasses a polypeptide having an amino acid sequence identical to any one of SEQ ID NO:70, SEQ ID NO:71, or SEQ ID NO:72.

In a sixth aspect, the invention features a vector including a nucleic acid having a polynucleotide sequence, for example, SEQ ID NO:2, SEQ ID NO:4, SEQ ID NO:6, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:73, SEQ ID NO:74, or SEQ ID NO:75. Preferably, this vector is capable of directing expression of the nucleic acid, for example, in a cell.

A seventh aspect of the invention encompasses a transgenic cell including a nucleic acid sequence encoding a lin-8, a lin-56, or a lin-61 polypeptide, where the nucleic acid sequence is located in the genome of the cell in a position in which it does not naturally occur. In addition, the nucleic acid sequence may be operably linked to a heterologous promoter.

Additional aspects of the invention feature purified antibodies which specifically bind to a LIN-8, LIN-56, or LIN-61 polypeptide.

In further aspects, the invention provides methods of modulating proliferation of a cell which involve administering a proliferation-modulating amount of a polypeptide, or a nucleic acid encoding a polypeptide, having the amino acid sequence of SEQ ID NO:1, SEQ ID NO:3, or SEQ ID NO:5 to a cell for example, a mammalian cell, such as a human cell. In addition, the nucleic acid sequence may be contained in a vector.

In another aspect, the invention features a method of identifying a compound that modulates cell proliferation, involving: (a) providing a cell expressing a nucleic acid, for example, a lin-8, lin-56, or lin-61 nucleic acid, or a reporter gene, operably linked to a lin-8, lin-56, or lin-61 promoter, (b) contacting the cell with a candidate compound; and (c) measuring the expression of the nucleic acid, where an alteration in the level of expression of the nucleic acid indicates the presence of a compound that modulates cell proliferation. In preferred embodiments, step (c) involves measuring the expression of the protein encoded by the nucleic acid, for example by using an antibody that specifically binds to a LIN-8, LIN-56, or LIN-61 polypeptide, or step (c) may also involve measuring the mRNA level of the nucleic acid.

An additional aspect of the invention provides a method of identifying a candidate compound, for example, a polypeptide, that binds to a LIN-8, LIN-56, or LIN-61 polypeptide, involving: (a) providing the polypeptide; (b) contacting the polypeptide with a candidate compound; and (c) measuring the binding of the candidate compound to the polypeptide, where the binding indicates the presence of a candidate compound that binds a LIN-8, LIN-56, or LIN-61 polypeptide.

Furthermore, in another aspect, the invention provides a method of diagnosing an animal, for example, a mammal, such as a human, for the presence of a cell proliferation disease, such as cancer, or for an increased likelihood of developing a cell proliferation disease. This method involves determining whether a nucleic acid sample obtained from the animal includes a mutant lin-8, lin-56, or lin-61 nucleic acid, where the presence of the mutant lin-8, lin-56, or lin-61 nucleic acid indicates that the animal has a cell proliferation disease, or is at an increased likelihood of developing a cell proliferation disease. In preferred embodiments of this aspect of the invention, the mutant lin-8 nucleic acid may be, for example, lin-8(n2738), lin-8(n2731), lin-8(n3606), lin-8 (n3595), lin-8(n2739), lin-8(n3586), lin-8(n3588), lin-8 (n111), lin-8(n2741), lin-8(n3585), lin-8(n3646), lin-8 (n2376), lin-8(n2378), lin-8(n2403), lin-8(n2724), lin-8 (n3607), lin-8(n3591), lin-8(n3609), or lin-8(n3581), the mutant lin-56 nucleic acid may be, for example, lin-56 (n3355) or lin-56(n2728), and the mutant lin-61 nucleic acid may be, for example, lin-61(n3446), lin-61(n3447), lin-61 (n3624), or lin-61(n3635).

In an additional aspect, the invention features a method of diagnosing an animal, for example, a mammal, such as a human, for the presence of a cell proliferation disease, or an increased likelihood of developing a cell proliferation disease. This method involves measuring lin-8, lin-56, or lin-61 nucleic acid expression in a sample obtained from the animal, where an alteration in the expression, relative to a sample obtained from an unaffected animal, indicates that the animal has a cell proliferation disease, or an increased likelihood of developing a cell proliferation disease. In a preferred embodiment of this aspect, nucleic acid expression is measured by measuring the amount of the LIN-8, LIN-56, or LIN-61 polypeptide, for example, by using an antibody that specifically binds to a LIN-8, LIN-56, or LIN-61 polypeptide in the sample. However, nucleic acid expression may also be measured by measuring the amount of lin-8, lin-56, or lin-61 mRNA in the sample.

In a final aspect, the invention provides a method of identifying a nucleic acid that modulates cell proliferation. This method involves: (a) expressing in a cell (i) a first nucleic acid operably linked to a first promoter, where the first promoter may be the lin-8, lin-56, or lin-61 promoter, and (ii) a second nucleic acid operably linked to a second promoter; and (b) measuring the expression of the first nucleic acid, where a modulation in the expression of the first nucleic acid in the presence of the second nucleic acid, indicates that the second nucleic acid modulates cell proliferation. In a preferred embodiment of this aspect, the first nucleic acid is a lin-8, lin-56, or lin-61 nucleic acid. Furthermore, the measuring in step (b) may also involve comparing the amount of modulation in the expression of the first nucleic acid seen in the presence of the second nucleic acid with that seen in the presence of a control nucleic acid that does not modulate cell proliferation.

Definitions

By a "lin-8 nucleic acid" is meant a nucleic acid sequence, or fragment thereof, that is substantially identical to SEQ ID NO:2, or portions thereof. Preferably a "lin-8 nucleic acid" is identical to at least 100, 200, 300, 390, 400, 450, 500, 600, 700, 800, 900, 1000, 1100, or 1200 contiguous nucleotides of SEQ ID NO:2, its complement, or to the corresponding RNA sequence. However, a "lin-8 nucleic acid" may also be identical to SEQ ID NO:2. In addition, a "lin-8 nucleic acid" may be characterized by its ability to modulate cell proliferation. Furthermore, a "lin-8 nucleic acid" may refer to a nucleic acid sequence including nucleic acids 375-989, 400-900, 450-850, 500-800, or 550-750 of SEQ ID NO:2, or to a nucleic acid that hybridizes under highly stringent conditions to these regions of SEQ ID NO:2. For example, highly stringent conditions include hybridization at about 42° C. and about 50% formamide, 0.1 mg/mL sheared salmon sperm DNA, 1% SDS, 2×SSC, 10% Dextran sulfate, a first wash at about 65° C., about 2×SSC, and 1% SDS, followed by a second wash at about 65° C. and about 0.1×SSC. Alternatively, highly stringent conditions may include hybridization at about 42° C. and about 50% formamide, 0.1 mg/mL sheared salmon sperm DNA, 0.5% SDS, 5×SSPE, 1×Denhardt's, followed by two washes at room temperature and 2×SSC, 0.1% SDS, and two washes at between 55-60° C. and 0.2×SSC, 0.1% SDS. The terms "gene" and "nucleic acid sequence" may be used interchangeably.

By a "mutant lin-8 nucleic acid" or a "mutated lin-8 nucleic acid" is meant a nucleic acid sequence, or fragment thereof, differing from the wild-type lin-8 nucleic acid sequence by at least one nucleotide. This nucleotide difference may result, for example, in the "mutant lin-8 nucleic acid" encoding a truncated LIN-8 protein or one containing a missense mutation. Preferably, the "mutant lin-8 nucleic acid" is identical to at least 100, 200, 300, 390, 400, 500, 600, 700, 800, 900, or 1000 contiguous nucleotides of SEQ ID NO:2, its complement, or the corresponding mRNA sequence. Most preferably, the "mutant lin-8 nucleic acid" is the lin-8(n2738), lin-8(n2731), lin-8(n3606), lin-8(n3595), lin-8(n2739), lin-8 (n3586), lin-8(n3588), lin-8(n111), lin-8(n2741), lin-8 (n3585), lin-8(n3646), lin-8(n2376), lin-8(n2378), lin-8 (n2403), lin-8(n2724), lin-8(n3607), lin-8(n3591), lin-8 (n3609), or lin-8(n3581) nucleic acid sequence. Furthermore, a *C. elegans* carrying a mutant lin-8 nucleic acid sequence and a reduction of function mutation in any synMuv class B gene will display a multivulva phenotype.

By a "lin-56 nucleic acid" is meant a nucleic acid sequence, or fragment thereof that is substantially identical to SEQ ID NO:4, or portions thereof. Preferably a "lin-56 nucleic acid" is identical to at least 100, 200, 300, 330, 390, 400, 450, 500, 600, 700, 800, 900, or 1000 contiguous nucleotides of SEQ ID NO:4, its complement, or to the corresponding RNA sequence. However, a "lin-56 nucleic acid" may also be identical to SEQ ID NO:4. In addition, a "lin-56 nucleic acid" may be characterized by its ability to modulate cell proliferation. Furthermore, a "lin-56 nucleic acid" may refer to a nucleic acid sequence including nucleic acids 376-1108, 400-1000, 400-700, 450-950, 450-800, 500-900, 550-850, or 600-800 of SEQ ID NO:4, or to a nucleic acid that hybridizes under highly stringent conditions to these regions of SEQ ID NO:4. For example, highly stringent conditions include hybridization at about 42° C. and about 50% formamide, 0.1 mg/mL sheared salmon sperm DNA, 1% SDS, 2×SSC, 10% Dextran sulfate, a first wash at about 65° C., about 2×SSC, and 1% SDS, followed by a second wash at about 65° C. and about 0.1×SSC. Alternatively, highly stringent conditions may include hybridization at about 42° C. and about 50% formamide, 0.1 mg/mL sheared salmon sperm DNA, 0.5% SDS, 5×SSPE, 1×Denhardt's, followed by two washes at room temperature and 2×SSC, 0.1% SDS, and two washes at between 55-60° C. and 0.2×SSC, 0.1% SDS.

By a "mutant lin-56 nucleic acid" or a "mutated lin-56 nucleic acid" is meant a nucleic acid sequence, or fragment thereof, differing from the wild-type lin-56 nucleic acid sequence by at least one nucleotide. This nucleotide difference may result, for example, in the "mutant lin-56 nucleic acid" encoding a truncated LIN-56 protein or one containing a missense mutation. Preferably, the "mutant lin-56 nucleic acid sequence" is identical to at least 100, 200, 330, 390, 400, 500, 600, 700, 800, 900, or 1000 contiguous nucleotides of SEQ ID NO:4, its complement, or the corresponding mRNA sequence. Most preferably, the "mutant lin-56 nucleic acid" is the lin-56(n3355) nucleic acid sequence. Furthermore, a *C. elegans* carrying a mutant lin-56 nucleic acid sequence and a reduction of function mutation in any synMuv class B gene will display a multivulva phenotype.

By a “lin-61 nucleic acid” is meant a nucleic acid sequence, or fragment thereof, that is substantially identical to SEQ ID NO:6, or portions thereof. Preferably a “lin-61 nucleic acid” is identical to at least 100, 200, 300, 390, 400, 450, 500, 600, 700, 800, 900, 1000, 1100, 1200, 1300, or 1400 contiguous nucleotides of SEQ ID NO:6, its complement, or to the corresponding RNA sequence. However, a “lin-61 nucleic acid” may also be identical to SEQ ID NO:6. In addition, a “lin-61 nucleic acid” may be characterized by its ability to modulate cell proliferation. Furthermore, a “lin-61 nucleic acid” may refer to a nucleic acid sequence including nucleic acids 375-1150, 400-1100, 400-1000, 450-950, 500-1000, 500-900, or 550-850 of SEQ ID NO:6, or to a nucleic acid that hybridizes under highly stringent conditions to these regions of SEQ ID NO:6. For example, highly stringent conditions include hybridization at about 42° C. and about 50% formamide, 0.1 mg/mL sheared salmon sperm DNA, 1% SDS, 2×SSC, 10% Dextran sulfate, a first wash at about 65° C., about 2×SSC, and 1% SDS, followed by a second wash at about 65° C. and about 0.1×SSC. Alternatively, highly stringent conditions may include hybridization at about 42° C. and about 50% formamide, 0.1 mg/mL sheared salmon sperm DNA, 0.5% SDS, 5×SSPE, 1×Denhardt’s, followed by two washes at room temperature and 2×SSC, 0.1% SDS, and two washes at between 55-60° C. and 0.2×SSC, 0.1% SDS.

However, a “lin-61 nucleic acid” may also be identical to at least 100, 200, 300, 390, 450, 500, 600, 700, 800, 900, 1000, 1100, 1200, 1300, or 1400 contiguous nucleotides of SEQ ID NO:76, its complement, or to the corresponding RNA sequence. In addition, a “lin-61 nucleic acid” may be identical to SEQ ID NO:76.

By a “mutant lin-61 nucleic acid” or a “mutated lin-61 nucleic acid” is meant a nucleic acid sequence, or fragment thereof, differing from the wild-type lin-61 nucleic acid sequence by at least one nucleotide. This nucleotide difference may result, for example, in the “mutant lin-61 nucleic acid” encoding a truncated LIN-61 protein or one containing a missense mutation. Preferably, the “mutant lin-61 nucleic acid” is identical to at least 100, 200, 300, 390, 400, 500, 600, 700, 800, 900, 1000, 1100, 1200, 1300, or 1400 contiguous nucleotides of SEQ ID NO:6, its complement, or the corresponding mRNA sequence. Most preferably, the “mutant lin-61 nucleic acid” is the lin-61(n3446), lin-61(n3447), or lin-61(n3624) nucleic acid sequence. However, a mutant “lin-61 nucleic acid,” for example, a lin-61(sy223) or lin-61(n3635) nucleic acid sequence, may also be identical to at least 100, 200, 300, 390, 400, 500, 600, 700, 800, 900, 1000, 1100, 1200, 1300, or 1400 contiguous nucleotides of SEQ ID NO:76, its complement, or the corresponding mRNA sequence. Furthermore, a *C. elegans* carrying a mutant lin-61 nucleic acid sequence and a reduction of function mutation in any synMuv class A gene will display a multivulva phenotype.

By a “lin-8(n111) nucleic acid” is meant a nucleic acid sequence having SEQ ID NO:16, its complement, or the corresponding RNA sequence.

By a “lin-8(n2741) nucleic acid” is meant a nucleic acid sequence having SEQ ID NO:18, its complement, or the corresponding RNA sequence.

By a “lin-8(n2738) nucleic acid” is meant a nucleic acid sequence having SEQ ID NO:20, its complement, or the corresponding RNA sequence.

By a “lin-8(n2731) nucleic acid” is meant a nucleic acid sequence having SEQ ID NO:22, its complement, or the corresponding RNA sequence.

By a “lin-8(n3585) nucleic acid” is meant a nucleic acid sequence having SEQ ID NO:24, its complement, or the corresponding RNA sequence.

By a “lin-8(n3646) nucleic acid” is meant a nucleic acid sequence having SEQ ID NO:26, its complement, or the corresponding RNA sequence.

By a “lin-8(n3606) nucleic acid” is meant a nucleic acid sequence having SEQ ID NO:28, its complement, or the corresponding RNA sequence.

By a “lin-8(n2376) nucleic acid” is meant a nucleic acid sequence having SEQ ID NO:30, its complement, or the corresponding RNA sequence.

By a “lin-8(n2378) nucleic acid” is meant a nucleic acid sequence having SEQ ID NO:32, its complement, or the corresponding RNA sequence.

By a “lin-8(n3595) nucleic acid” is meant a nucleic acid sequence having SEQ ID NO:34, its complement, or the corresponding RNA sequence.

By a “lin-8(n2403) nucleic acid,” a “lin-8(2724) nucleic acid,” or a “lin-8(3607) nucleic acid” is meant a nucleic acid sequence having SEQ ID NO:36, its complement, or the corresponding RNA sequence.

By a “lin-8(n3581) nucleic acid” is meant a nucleic acid sequence having SEQ ID NO:38, its complement, or the corresponding RNA sequence.

By a “lin-8(n3609) nucleic acid” is meant a nucleic acid sequence having SEQ ID NO:40, its complement, or the corresponding RNA sequence.

By a “lin-8(n2739) nucleic acid” is meant a nucleic acid sequence having SEQ ID NO:42, its complement, or the corresponding RNA sequence.

By a “lin-8(n3586) nucleic acid,” or a “lin-8(n3588) nucleic acid” is meant a nucleic acid sequence having SEQ ID NO:44, its complement, or the corresponding RNA sequence.

By a “lin-8(n3591) nucleic acid” is meant a nucleic acid sequence having SEQ ID NO:46, its complement, or the corresponding RNA sequence.

By a “lin-56(n3355) nucleic acid” is meant a nucleic acid sequence having SEQ ID NO:48, its complement, or the corresponding RNA sequence.

By a “lin-56(n2728) nucleic acid” is meant a deletion encompassing all or part of a lin-56 nucleic acid sequence in an isolated nucleic acid containing the genomic region that normally contains a lin-56 nucleic acid sequence.

By a “lin-61 (n3446) nucleic acid” is meant a nucleic acid sequence having SEQ ID NO:73, its complement, or the corresponding RNA sequence.

By a “lin-61(n3447) nucleic acid” is meant a nucleic acid sequence having SEQ ID NO:74, its complement, or the corresponding RNA sequence.

By a “lin-61(n3624) nucleic acid” is meant a nucleic acid sequence having SEQ ID NO:75, its complement, or the corresponding RNA sequence.

By a “lin-61(sy223) nucleic acid” is meant a nucleic acid sequence having SEQ ID NO:77, its complement, or the corresponding RNA sequence.

By a “lin-61(n3635) nucleic acid” is meant a nucleic acid sequence having SEQ ID NO:78, its complement, or the corresponding RNA sequence.

By “LIN-8 polypeptide” or “LIN-8 protein” is meant a polypeptide or protein encoded by a lin-8 nucleic acid sequence. Preferably, a “LIN-8 polypeptide” is identical to at least 30, 50, 100, 130, 200, 250, 300, or 350 contiguous amino acids of SEQ ID NO:1. Most preferably, a “LIN-8 polypeptide” is identical to SEQ ID NO:1 and has a LIN-8 biological activity described below.

By a "mutant LIN-8 polypeptide" is meant a LIN-8 polypeptide that differs by at least one amino acid from a wild-type LIN-8 polypeptide. In addition, a mutant LIN-8 polypeptide may also be a truncated protein, for example, due to the presence of a premature stop codon in the nucleic acid sequence encoding the mutant LIN-8 polypeptide. In addition, a "mutant LIN-8 polypeptide" is preferably 50%, 60%, 70%, 75%, 80%, 85%, 90%, 95%, or even 99% identical to at least 30, 50, 100, 130, 200, 250, 300, or 350 contiguous amino acids of SEQ ID NO:1. Furthermore, the mutant LIN-8 polypeptide preferably is the polypeptide encoded by lin-8 (n2738), lin-8(n2731), lin-8(n3606), lin-8(n3595), lin-8 (n2739), lin-8(n3586), lin-8(n3588), lin-8(n111), lin-8 (n2741), lin-8(n3585), lin-8(n3646), lin-8(n2376), lin-8 (n2378), lin-8(n2403), lin-8(n2724), lin-8(n3607), lin-8 (n3591), lin-8(n3609), or lin-8(n3581). Most preferably, a "mutant LIN-8 polypeptide" is identical to SEQ ID NO:17, SEQ ID NO:19, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, or SEQ ID NO:47.

By "LIN-56 polypeptide" or "LIN-56 protein" is meant a polypeptide or protein encoded by a lin-56 nucleic acid sequence. Preferably, a "LIN-56 polypeptide" is identical to at least 30, 50, 100, 130, 200, 250, or 300 contiguous amino acids of SEQ ID NO:3. Most preferably, a "LIN-56 polypeptide" is identical to SEQ ID NO:3 and has a LIN-56 biological activity described below.

By a "mutant LIN-56 polypeptide" is meant a LIN-56 polypeptide that differs by at least one amino acid from a wild-type LIN-56 polypeptide. In addition, a mutant LIN-56 polypeptide may also be a tuncated protein, for example, due to the presence of a premature stop codon in the nucleic acid sequence encoding the mutant LIN-56 polypeptide. In addition, a "mutant LIN-56 polypeptide" is preferably 50%, 60%, 70%, 75%, 80%, 85%, 90%, 95%, or even 99% identical to at least 30, 50, 100, 130, 200, 250, or 300 contiguous amino acids SEQ ID NO:3. Furthermore, the mutant LIN-56 polypeptide is preferably the polypeptide encoded by a lin-56(n3355) nucleic acid.

By "LIN-61 polypeptide" or "LIN-61 protein" is meant a polypeptide or protein encoded by a lin-61 nucleic acid sequence. Preferably, a "LIN-61 polypeptide" is identical to at least 30, 50, 100, 130; 200, 250, 300, 350, or 400 contiguous amino acids of SEQ ID NO:5. Most preferably, a "LIN-61 polypeptide" is identical to SEQ ID NO:5 and has a LIN-61 biological activity described below.

By a "mutant LIN-61 polypeptide" is meant a LIN-61 polypeptide that differs by at least one amino acid from a wild-type LIN-61 polypeptide. In addition, a mutant LIN-61 polypeptide may also be a truncated protein, for example, due to the presence of a premature stop codon in the nucleic acid sequence encoding the mutant LIN-61 polypeptide. In addition, a "mutant LIN-61 polypeptide" is preferably 50%, 60%, 70%, 75%, 80%, 85%, 90%, 95%, or even 99% identical to at least 30, 50, 100, 130, 200, 250, 300, 350, or 400 contiguous amino acids SEQ ID NO:5. Preferably, a "mutant LIN-61 polypeptide" is encoded by a lin-61(n3446), lin-61(n3447), or lin-61(3624) nucleic acid. Most preferably, a "mutant LIN-61 polypeptide" is identical to SEQ ID NO:70, SEQ ID NO:71, or SEQ ID NO:72.

By an "amino acid alteration," as used herein, is meant a change in an amino acid sequence, relative to the wild-type sequence. Such a change may be, for example, the substitution of one or more amino acids with heterologous amino acids, as well as the addition or deletion of one or more amino acids. In addition, an "amino acid alteration" may result in a truncated protein.

By "heterologous promoter" is meant a nucleic acid sequence that drives expression of a nucleic acid sequence, e.g., a gene, with which is not naturally associated.

By a "synMuv gene" is meant a nucleic acid sequence encoding LIN-9, LIN-15A, LIN-15B, LIN-37, LIN-35, LIN-53, LIN-55, LIN-52, LIN-54, and the E2F-1 gene of *C. elegans*, and the LIN-54 genes of the mouse and human. SynMuv genes also include those which encode polypeptides encoded by ESTs zp44h06.s1, zr79e11.r1, and EST180962 and any other nucleic acid sequence identified as a synMuv sequence known in the art.

By "synMuv polypeptide" or "synMuv protein" is meant a polypeptide encoded by a synMuv gene.

By "LIN-8 biological activity," "LIN-56 biological activity," or "LIN-61 biological activity" is meant an activity of a LIN-8, LIN-56, or LIN-61 polypeptide, when expressed or overexpressed, either alone or in combination, with another polypeptide in a cell which is absent or decreased in the absence of the LIN-8, LIN-56, or LIN-61 polypeptide. A LIN-8, LIN-56, or LIN-61 biological activity includes modulating or altering cell proliferation. Another activity is rescuing (i.e., suppressing) a LIN-8, LIN-56, or LIN-61 mutant phenotype. Less preferably, a LIN-8, LIN-56, or LIN-61 biological activity involves binding to other known synMuv polypeptides, in vivo or in vitro. Another LIN-8, LIN-56, or LIN-61 biological activity is binding to an antibody that recognizes a LIN-8, LIN-56, or LIN-61 polypeptide. Finally, a LIN-8, LIN-56, or LIN-61 biological activity may also be the ability of the nucleic acid sequence encoding the polypeptide to hybridize to a detectably-labeled probe from a lin-8, lin-56, or lin-61 nucleic acid sequence under high, or less preferably, low stringency conditions.

By "modulating cell proliferation" or "altering cell proliferation" is meant increasing or decreasing the number of cells which undergo cell division in a given cell population or altering the fate of a given cell. It will be appreciated that the degree of modulation provided by LIN-8, LIN-56, LIN-61, or a modulatory compound, in a given assay will vary, but that one skilled in the art can determine the statistically significant change (e.g., a p-value$\leqq$0.05) in the level of cell proliferation which identifies a modulatory compound.

By "inhibiting cell proliferation" is meant any decrease in the number of cells that undergo division relative to an untreated control. Preferably, the decrease is at least 25%, more preferably the decrease is at least 50%, and most preferably the decrease is at least 75%, 80%, or even 100%.

By "a cell proliferation disease," is meant a disorder that is due to any genetic alteration within a differentiated cell that results in the abnormal proliferation of the cell. Examples of such changes include mutations in genes involved in the regulation of the cell cycle, of growth control, or of apoptosis, and further can include tumor suppressor genes and proto-oncogenes. In addition, "a cell proliferation disease" may be the result of, for example, an inappropriately high level of cell division, or an inappropriately low level of apoptosis, or both Specific examples of cell proliferation diseases are various types of cancer including cancers of the reproductive system, such as cervical cancer and ovarian cancer.

By "unaffected animal," as used herein, is meant an animal that does not have, or is not at an increased likelihood of developing, a cell proliferation disease.

By "specifically binds," as used herein in reference to an antibody, is meant an antibody that recognizes a specific protein, or shows staining in a sample, but does not recognize a specific protein, or show staining, in a sample not containing the protein of interest. Assays used to determine binding include, for example, Western blotting, affinity column purification, and tissue staining. A sample not containing the protein of interest may be obtained from an organism mutant for the protein of interest.

By "polypeptide" is meant any chain of amino acids, regardless of length or post-translational modification (e.g., glycosylation or phosphorylation).

By "substantially identical" is meant a polypeptide or nucleic acid exhibiting at least 50%, preferably 60%, 70%, 75%, or 80%, more preferably 90% or 95%, and most preferably 99% homology to a reference amino acid or nucleic acid sequence. For polypeptides, the length of comparison sequences will generally be at least 16 amino acids, preferably at least 20 amino acids, more preferably at least 25, 35, 50, 75, 100, 110, 130, 150, 200, 250, 300, or 310 amino acids, and most preferably the full-length amino acid sequence. For nucleic acids, the length of comparison sequences will generally be at least 50 nucleotides, preferably at least 60 nucleotides, more preferably at least 75, 110, 200, 330, 390, 450, 600, 800, 900, or 1000 nucleotides, and most preferably the full-length nucleotide sequence.

Sequence identity may be measured using sequence analysis software on the default setting (i.e., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

A polypeptide which is substantially identical to a LIN-8, LIN-56, or LIN-61 polypeptide (SEQ ID NOS:1, 3, or 5) may be, for example, another substantially pure naturally-occurring mammalian LIN-8, LIN-56, or LIN-61 polypeptide as well as an allelic variant; a natural mutant; an induced mutant; and a DNA sequence that encodes a polypeptide. In addition, such polypeptides may also be any polypeptides specifically bound by antisera directed to a LIN-8, LIN-56, or LIN-61 polypeptide. Furthermore, polypeptides that are substantially identical to LIN-8, LIN-56, or LIN-61 polypeptides also include chimeric polypeptides that have a LIN-8, LIN-56, or LIN-61 polypeptide portion. Preferably, this LIN-8, LIN-56, or LIN-61 polypeptide portion contains at least 50, 75, 90, 110, 130, 150, 200, 250, or 300 contiguous amino acids of SEQ ID NOS:1, 3, or 5.

By a "substantially pure polypeptide" is meant a polypeptide, for example, LIN-8, LIN-56, or LIN-61, that has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, a LIN-8, LIN-56, or LIN-61 polypeptide. A substantially pure LIN-8, LIN-56, or LIN-61 polypeptide may be obtained, for example, by extraction from a natural source (e.g., a fibroblast, neuronal cell or lymphocyte cell); by expression of a recombinant nucleic acid encoding a LIN-8, LIN-56, or LIN-61 polypeptide; or by chemically synthesizing the polypeptide. Purity can be measured by any appropriate method, e.g., column chromatography, polyacrylamide gel electrophoresis, or by HPLC analysis.

A protein is substantially free of naturally associated components when it is separated from those contaminants, which accompany it in its natural state. Thus, a protein, which is chemically synthesized or produced in a cellular system different from the cell from which it naturally originates, will be substantially free from its naturally associated components. Accordingly, substantially pure polypeptides include those derived from eukaryotic organisms but synthesized in *E. coli* or other prokaryotes.

By a "substantially pure DNA" or "a substantially pure nucleic acid sequence" is meant a nucleic acid sequence or DNA that is free of the genes which, in the naturally-occurring genome of the organism from which the nucleic acid sequence or DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence or an antisense DNA or RNA sequence.

By "antisense" is meant a nucleic acid sequence, regardless of length, that is complementary to the coding strand gene encoding a nucleic acid sequence of interest, for example, a lin-8, lin-56, or lin-61 nucleic acid sequence. Preferably, the antisense nucleic acid is capable of decreasing the biological activity of the polypeptide encoded by the nucleic acid sequence of interest when present in a cell. Preferably the decrease is at least 10%, relative to a control, more preferably 25%, 50%, or 75%, and most preferably 100%.

By "analog of LIN-8", "analog of LIN-56", or "analog of LIN-61," is meant differing from a naturally-occurring LIN-8, LIN-56, or LIN-61 polypeptide by amino acid sequence differences, by post-translational modifications, or by both. Analogs of the invention will generally exhibit at least 85%, more preferably 90%, and most preferably 95% or even 99% identity with all or part of a naturally occurring LIN-8, LIN-56, or LIN-61 amino acid sequence (SEQ ID NOS:1, 3, or 5). The length of sequence comparison is at least 25, 50, 75, 100, 110, 130, 150, 200, 250, or 300 contiguous amino acid residues, and more preferably more than 310 amino acid residues, for example, the full-length sequence. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes.

In addition, analogs may differ from the naturally-occurring LIN-8, LIN-56, or LIN-61 polypeptide by alterations in primary sequence. These include genetic variants, both natural and induced (for example, resulting from random mutagenesis by irradiation or exposure to ethanemethylsulfate (EMS) or by site-specific mutagenesis as described in Sambrook, Fritsch and Maniatis, *Molecular Cloning: A Laboratory Manual* (2d ed.), Cold Spring Harbor Press, 1989, or Ausubel et al., *Current Protocols in Molecular Biology,* Wiley Interscience, New York, 2000). Also included are cyclized peptides, molecules, and analogs which contain residues other than L-amino acids, e.g., D-amino acids or non-naturally-occurring or synthetic amino acids, e.g., β or γ amino acids.

As used herein, the term "LIN-8 polypeptide fragment", "LIN-56 polypeptide fragment", or "LIN-61 polypeptide fragment," means at least 20 contiguous amino acids, preferably at least 50 contiguous amino acids, more preferably at least 100 contiguous amino acids, and most preferably at least 110, 130, 150, 200, 250, 300, 310 or more contiguous amino acids of SEQ ID NOS:1, 3, or 5. Fragments of LIN-8, LIN-56, or LIN-61 polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events). Preferable fragments or analogs according to the invention are those which facilitate specific detection of a lin-8, lin-56, or lin-61 nucleic acid or amino acid sequence in a sample to be diagnosed.

By "transformed cell" is meant a cell into which (or into an ancestor of which) has been introduced, by means of recombinant DNA techniques, a DNA molecule encoding (as used herein) a LIN-8, LIN-56, LIN-61 polypeptide, or a reporter gene.

By "transgene" is meant any piece of DNA that is inserted by artifice into a cell, and becomes part of the genome of the organism that develops from that cell. Such a transgene may include a gene that is partly or entirely heterologous (i.e., foreign) to the transgenic organism, or may represent a gene homologous to an endogenous gene of the organism. Self-replicating units, such as artificial chromosomes, are included.

By "transgenic" is meant any cell that includes a DNA sequence inserted by artifice into a cell and that becomes part of the genome of the organism that develops from that cell. As used herein, the transgenic organism is generally a transgenic nematode (e.g., *C. elegans*), non-human mammal (e.g., a rodent such as a rat or mouse), or a plant, and the DNA sequence (transgene) is inserted by artifice into the nuclear genome.

By "transformation" is meant any method for introducing foreign molecules into a cell. Microinjection, lipofection, calcium phosphate precipitation, retroviral delivery, electroporation, and biolistic transformation are just a few of the teachings which may be used. For example, biolistic transformation is a method for introducing foreign molecules into a cell using velocity driven microprojectiles such as tungsten or gold particles. Such velocity-driven methods originate from pressure bursts, which include, but are not limited to, helium driven, air-driven, and gunpowder-driven techniques. Biolistic transformation may be applied to the transformation or transfection of a wide variety of cell types and intact tissues including, without limitation, intracellular organelles, bacteria, yeast, fungi, algae, animal tissue, and cultured cells.

By "positioned for expression" is meant that a nucleic acid molecule is positioned adjacent to a nucleic acid sequence that directs transcription and translation of the sequence (i.e., facilitates the production of, e.g., a LIN-8, LIN-56, or LIN-61 polypeptide, a recombinant protein or an RNA molecule).

By "reporter gene" is meant a gene whose expression may be assayed; such genes include, without limitation, those encoding glucuronidase (GUS), luciferase, chloramphenicol transacetylase (CAT), green fluorescent protein (GFP), and β-galactosidase.

By "promoter" is meant minimal sequence sufficient to direct transcription. Also included in the invention are those promoter elements that are sufficient to render promoterdependent gene expression controllable for specific cell-types or tissues. In addition, such promoters may also render gene expression inducible by external signals or agents. These promoter elements may be located in the 5' or 3' regions of the native gene, for example, a lin-8, lin-56, or lin-61 gene.

By "operably linked" is meant that a gene and a regulatory sequence(s) are connected in such a way as to permit gene expression when the appropriate molecules (e.g., transcriptional activator proteins) are bound to the regulatory sequence (s).

By "detectably-labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as $^{32}P$ or $^{35}S$) and nonradioactive labeling (e.g., chemiluminescent labeling, such as fluorescein labeling).

By "purified antibody" is meant an antibody that is at least 60%, by weight, free from proteins and naturally-occurring organic molecules with which it is naturally associated. Preferably, the preparation is at least 75%, more preferably 80%, 85%, or 90%, and most preferably at least 99%, by weight, antibody, e.g., a LIN-8, LIN-56, or LIN-61 specific antibody. A purified antibody may be obtained, for example, by affinity chromatography using recombinantly-produced protein or conserved motif peptides and standard techniques.

By "specifically binds" is meant an antibody which recognizes and binds a protein, but which does not substantially recognize and bind other molecules in a sample, e.g., a biological sample, which naturally includes additional proteins.

By a "candidate compound" or "test compound" is meant a chemical, be it naturally-occurring or artificially-derived, that is surveyed for its ability to modulate cell proliferation, by employing one of the assay methods described herein. Candidate compounds may include, for example, peptides, polypeptides, synthetic organic molecules, naturally-occurring organic molecules, nucleic acid molecules, and components thereof.

Other features and advantages of the invention will be apparent from the following description of the preferred embodiments thereof, and from the claims.

BRIEF DESCRIPTION OF THE DRAWINGS

FIG. 7 shows the sequence homology of the mbt repeats present in LIN-61 (SEQ ID NO:5) compared with mbt repeats from transcriptional repressors in other species (SEQ ID NOS:7-15).

DETAILED DESCRIPTION OF THE INVENTION

1. Introduction

Figure 1:
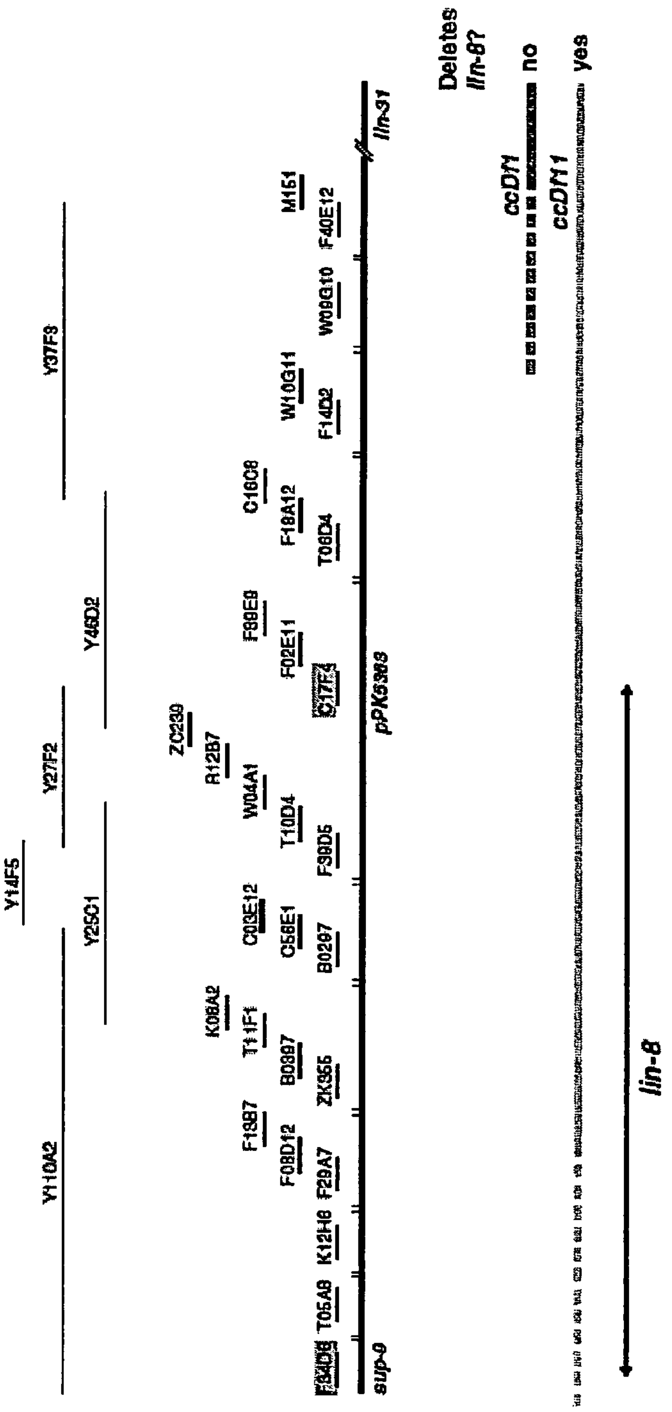
FIG. 1 is a schematic representation of the mapping of lin-8.

We have cloned lin-8, lin-56, and lin-61 of the *C. elegans* synMuv gene family. lin-8 and lin-56 are class A genes, and lin-61 is a class B gene. These genes function in cell proliferation and are members of a tumor suppressor pathway, which is related to a tumor suppressor pathway of clinical importance in humans. Accordingly, the genes described herein, mutations in these genes, as well as the previously known synMuv genes, may be used to identify new tumor suppressors in other species, such as mammals, and may be used to identify therapeutic compounds. The encoded polypeptides, and nematodes carrying the newly cloned genes or mutations in these genes may similarly be employed.

lin-8 encodes a novel polypeptide. The invention provides the polypeptide sequence (SEQ ID NO:1), the nucleic acid sequence (SEQ ID NO: 2), and lin-8 mutants, for example, lin-8(n2738), lin-8(n2731), lin-8(n3606), lin-8(n3595), lin-8 (n2739), lin-8(n3586), lin-8(n3588), lin-8(n111), lin-8 (n2741), lin-8(n3585), lin-8(n3646), lin-8(n2376), lin-8 (n2378), lin-8(n2403), lin-8(n2724), lin-8(n3607), lin-8 (n3591), lin-8(n3609) and lin-8(n3581).

We also cloned lin-56 and describe the LIN-56 polypeptide sequence (SEQ ID NO: 3) and the lin-56 nucleic acid sequence (SEQ ID NO: 4) in the present invention, as well as lin-56 mutants, such as lin-56(n3355) and lin-56(n2728).

In addition, we cloned lin-61 (SEQ ID NO:6). The polypeptide encoded by this gene (SEQ ID NO:5) has homology with *C. elegans* and human polypeptides of unknown function, and to *Drosophila* polycomb group members and their related human proteins. Furthermore, we identified lin-61 mutants, for example, lin-61(n3446), lin-61(n3447), lin-61(n3624), and lin-61(n3635).

The present invention also provides mammalian homologs of the novel lin-8, lin-56, or lin-61 genes, which may be obtained using routine methods known to those skilled in the art. Such homologs may function in activating, enhancing, or otherwise intensifying the effects of tumor suppressors or oncogenes in mammals.

Genetic enhancer or suppressor screens may be performed to identify new genes that may function in initiating, enhancing, or otherwise interfacing with this tumor suppressor pathway. In addition, the identification of the lin-8, lin-56, or lin-61 genes, in combination with what is known about proliferative disease pathways in mammals, allows one skilled in the art to readily devise drug screens involving these genes to search for compounds that affect cell proliferation. Specifically, compounds that block the Muv phenotype of animals with a mutation in lin-4, lin-56, or lin-61 mutant animals are potential anti-tumor agents. The Muv phenotype may be present, for example, in a *C. elegans* with either a mutation in lin-8 or lin-56 in combination with a reduction of function mutation in a synMuv B gene, or a mutation in lin-61 in combination with a reduction of function mutation in a synMuv A gene. Compounds that stimulate cell division in animals with a single, silent lin-8, lin-56, or lin-61 mutation are likely to be agonists of cell proliferation and may act in a manner analogous to growth factors.

By providing insight regarding the function of the lin-8, lin-56, or lin-61 members of the synMuv genes in tumor suppression, and by identifying mutants in these genes, we have provided, in concert with generally known molecular biology and nematode genetic methods, the necessary elements of such methods and the compounds required for the practice of such methods.

2. Cloning of lin-8

The lin-8(n111) allele was isolated in an EMS screen for cell-lineage mutants (Horvitz and Sulston, Genetics 96:435-454, 1980). The lin-8 gene was mapped to the eight-map-unit interval between sup-9 and lin-31 on chromosome II (Ferguson and Horvitz, Genetics 123:109-121, 1989). As there were no other cloned genes in this interval that could be used for finer mapping, we used deficiencies to more precisely locate lin-8 on the physical map. The left endpoints of three deletions, ccDfl1, ccDfl, and ccDf2, that remove lin-31 but not sup-9 had previously been roughly located and we further mapped the left endpoint of ccDf1 using PCR techniques. Analysis of the phenotypes of the Df heterozygotes revealed that lin-8 is only deleted by ccDf11, thus placing lin-8 between sup-9 and M151 (FIG. 1).

Figure 2:
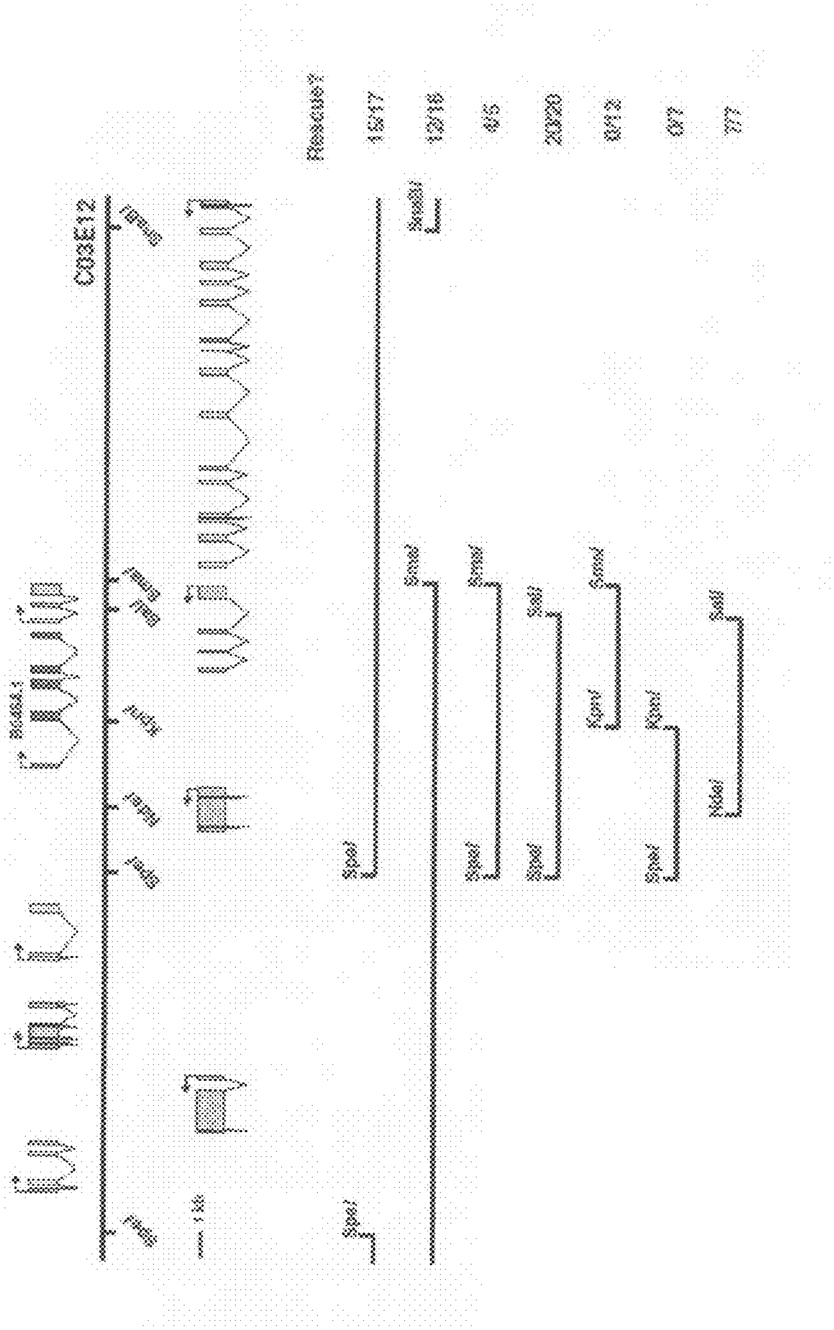
FIG. 2 is a schematic representation of the rescue of LIN-8 by B0454.1.

Further mapping against the polymorphism pPK5363 placed lin-8 between sup-9 and C17F4. We identified a pool of two cosmids in this region that rescued the lin-8(lf) synMuv phenotype in germline transformation experiments. We further determined that this rescue effect was attributable to the single cosmid C03E12. Germline transformation experiments with subclones of C03E12 indicated that lin-8 is encoded by the predicted gene B0454.1 (FIG. 2). RNAi of this open reading frame produces a class A synMuv phenotype. Furthermore, nineteen alleles of lin-8 have been sequenced and all alleles contain mutations within B0454.1 (Table 1).

TABLE 1

Mutations Identified in lin-8 Alleles

| lin-8 allele | WT sequence | Mutant Sequence | Amino Acid Change |
|---|---|---|---|
| n2738 | TGG | TAG | W79amber |
| n2731 | CAA | TAA | Q113ochre |
| n3606 | TGG | TGA | W147opal |
| n3595 | TGG | TAG | W163amber |
| n3609 | CAG | TAG | Q279amber |
| n2739 | AGA | TGA | R304opal |
| n3586, n3588 | CAA | TAA | Q340ochre |
| n111 | CTG | CCG | L20P |
| n2741 | GTG | ATG | V68M |
| n3585 | CGC | CAC | R127H |
| n3646 | CGC | CAC | R146H |
| n2376 | GAG | AAG | E148K |
| n2378 | CGC | TGC | R154C |
| n2403, n2724, n3607 | GAG | AAG | E164K |
| n3591 | GAG | AAG | E347K |
| n3581 | GTG | -TG | frameshift after aa192 |

Figure 3:
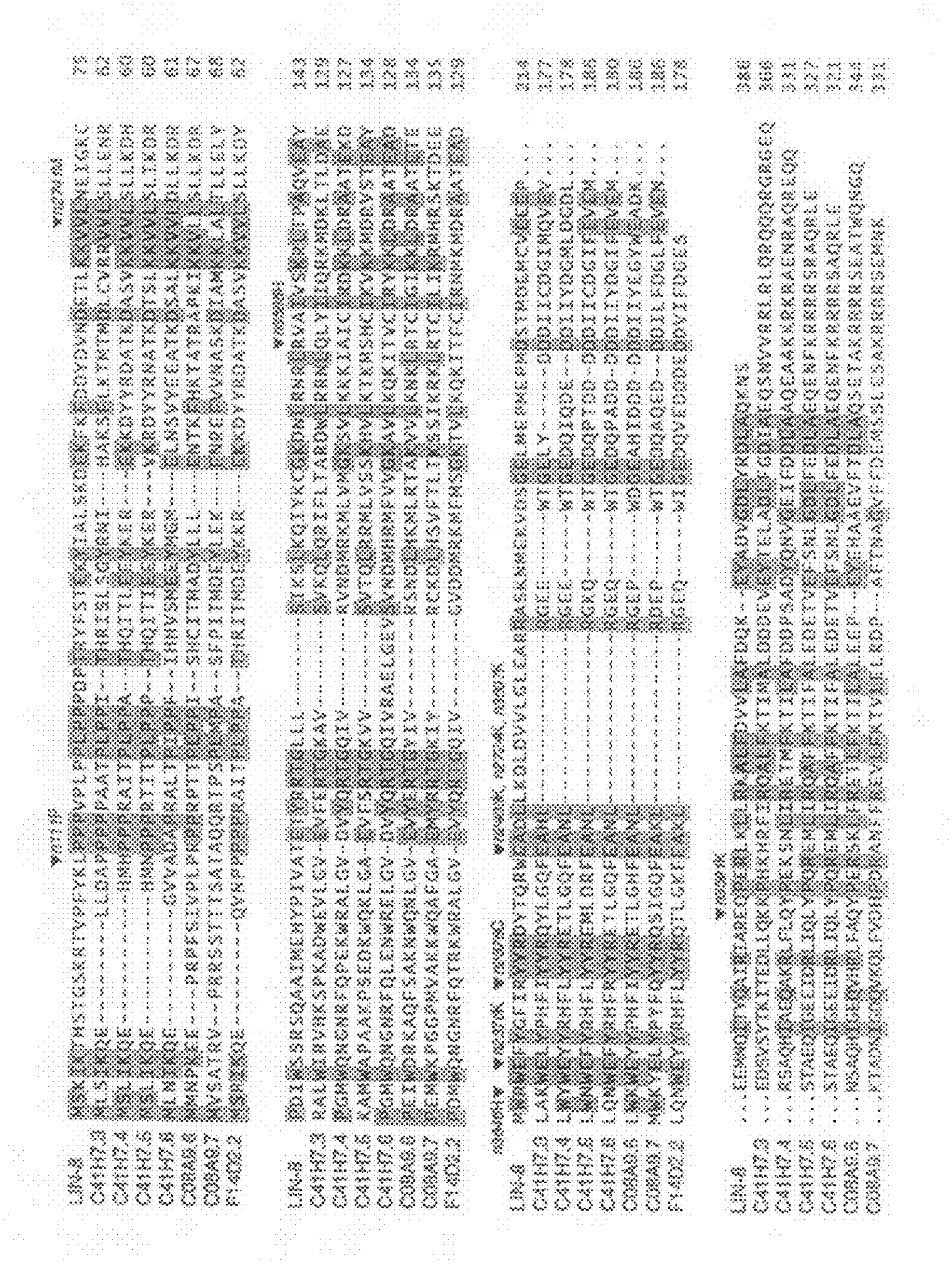
FIG. 3 shows the sequence homology of LIN-8 (SEQ ID NO:1) with several other polypeptides in *C. elegans* (SEQ ID NOS:55-67).

The LIN-8 polypeptide is 386 amino acids in length, is novel, and appears to be highly charged. However, the LIN-8 polypeptide shares sequence homology with several other *C. elegans* polypeptides (FIG. 3).

3. Cloning of lin-56

Figure 4:
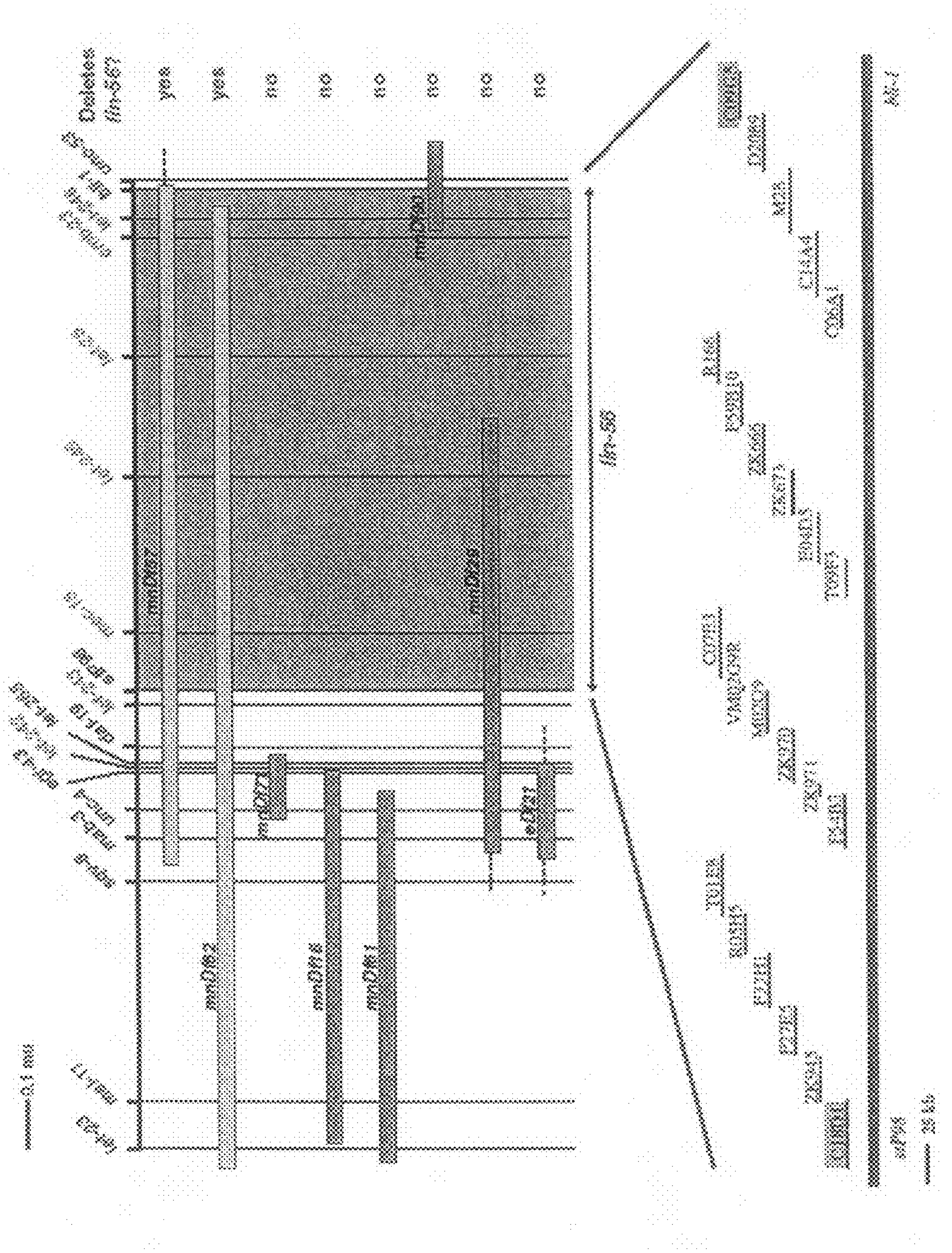
FIG. 4 is a schematic representation of the mapping of lin-56.
Figure 5:
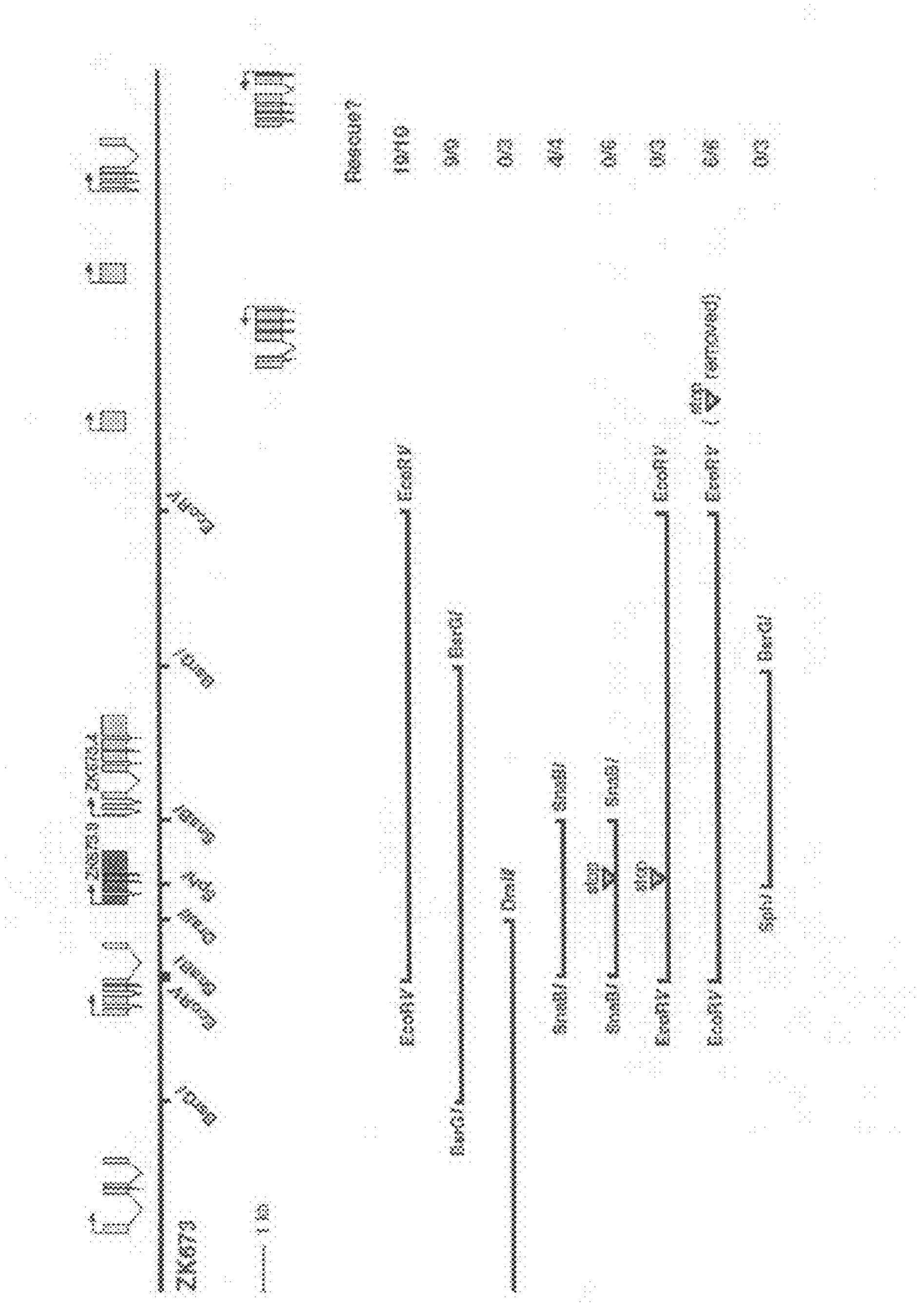
FIG. 5 is a schematic representation of the rescue of lin-56 by ZK673.3.

Identified as part of a screen to isolate new synMuv class A genes, lin-56 was previously mapped to the three-map-unit interval between dpy-10 and unc-53, close to unc-4, on chromosome II. We used the numerous deficiencies available in this region to further delineate the physical position of lin-56. The phenotypes of the Df heterozygotes suggested that lin-56 is positioned between the cloned markers stP98 and bli-1 (FIG. 4). We identified a pool of five cosmids in this region that rescued the lin-56(lf) synMuv phenotype in germline transformation experiments using a lin-56(n2728); lin-15B (n744) strain. This rescue effect was attributed to the single cosmid ZK673 (FIG. 5).

Further germline transformation experiments with ZK673 subclones limited the lin-56 candidates to two predicted genes, ZK673.3 and ZK673.4. Using a combination of Southern blotting and PCR techniques, we determined that lin-56 (n2728) contains an 11.2 kb deletion that completely eliminates these two genes and also removes the 3' end of a third gene, ZK673.2. RNAi of ZK673.3, but not ZK673.4, produced a synMuv phenotype in a lin-15B(n744) background.

We have also identified a second lin-56 allele, designated lin-56(n3355), isolated in a lin-56(n2728) non-complementation screen. Sequencing of this gene revealed that lin-56 (n3355) contains a stop codon in ZK673.3, confirming our identification of this open reading frame as lin-56.

Figure 6:
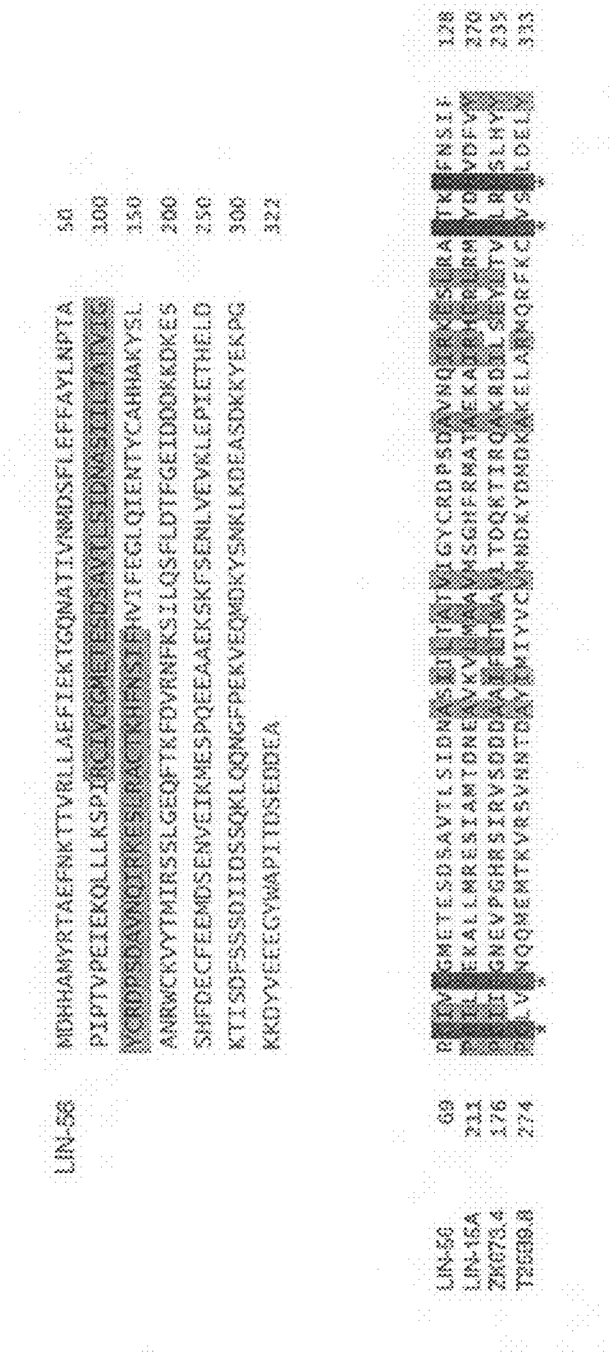
FIG. 6 shows the LIN-56 polypeptide sequence (SEQ ID NO:3) as well as an alignment indicating the homology of an internal region of LIN-56 (SEQ ID NO:51) with several other *C. elegans* polypeptides (SEQ ID NOS:52-54).

The LIN-56 polypeptide is 322 amino acids in length (SEQ ID NO:3). This polypeptide appears to be novel and highly charged. LIN-56 does have an internal sequence (SEQ ID NO:51) that shares weak similarities with sequences in ZK673.4, LIN-15A, and a predicted polypeptide T25B9.8 (SEQ ID NOS:52-54) (FIG. 6). This region (SEQ ID NO:51) contains a C3H motif, which consists of a series of three cysteines followed by a histidine (C-x(2)-C-x(16)-A-x(7)-V-x(9)-A-x(11)-C-x(2)-H), where "x" can be any amino acid and where the number in parentheses indicates the number of "x" amino acids present at that position of the motif. The C3H motif suggests the presence of a metal binding domain, for example, a zinc-finger domain. However, the spacing of these residues is unlike that seen in any of the traditional motifs of this type.

In addition, antibodies to LIN-56 have been generated, using the full length LIN-56 polypeptide to form a fusion protein with glutathione S-transferase. These antibodies were purified against a fusion between full length LIN-56 and maltose binding protein (MBP). The antibodies recognize the LIN-56 polypeptide in nematode extracts, as assessed by Western blot analysis.

4. Cloning of lin-61

Figure 8:
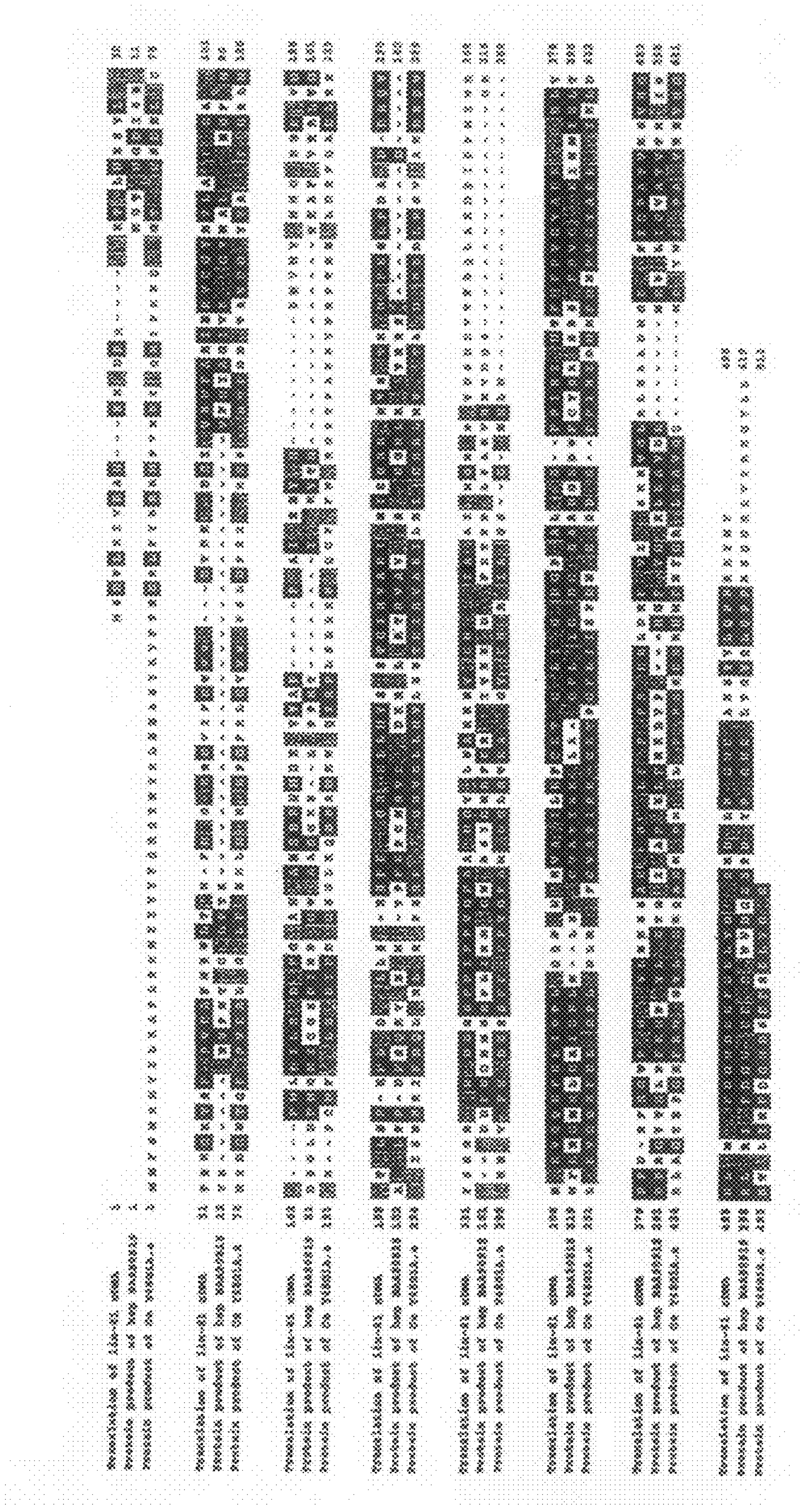
FIG. 8 shows a sequence alignment between LIN-61 (SEQ ID NO:5) and predicted worm (SEQ ID NO:69) and human (SEQ ID NO:68) proteins of unknown function.

We cloned the class B synthetic multivulva gene lin-61 by means of mapping, transformation rescue with cosmid R06C7, and the direct sequencing of multiple mutant alleles (see below). The cDNA sequence was determined based on the intron/exon structure of the genomic DNA. The predicted cDNA contains an SL1 splice leader sequence. Based upon a combination of sequence from the 5' and 3' ends of the cDNAs, and the genomic sequence of predicted ORF R06C7.7, we found lin-61 to encode a protein highly similar to predicted human and *C. elegans* proteins of undetermined function (FIG. 8).

The predicted LIN-61 protein contains motifs associated with transcriptional repressor proteins in species ranging from *Drosophila* to human, indicating that LIN-61 may play a similar role in transcriptional repression. The predicted LIN-61 protein contains four mbt repeats. These motifs are present in members of the *Drosophila melanogaster* polycomb family of transcriptional repressor proteins, including the proteins lethal(3) malignant brain tumor (1(3)mbt), and sex combs on the midleg (SCM). These motifs are also present in homologs of polycomb family members in other species, including human (FIG. 7). Analysis of mutant SCM alleles in *Drosophila* suggests that these mbt repeats are essential for SCM function (Bowermann et al., Genetics 150: 675-686, 1998).

In addition, we found lin-61 to be 41.1% identical at the nucleotide level to *Drosophila* 1(3)mbt, and to be 40.8% identical at the nucleotide level to the human 1(3)mbt homolog. Homology at the protein level, however, is much greater within the mbt repeats.

We have isolated five alleles of lin-61 in addition to the mutation sy223 that originally defined the gene. A total of five alleles (including sy223) have been sequenced in our lab. sy223 is a single base pair alteration (G to A at position 2228 of SEQ ID NO:76) altering the splice acceptor site prior to the final exon of lin-61, lin-61(n3446) is single base pair alteration (C to T at position 1234 of SEQ ID NO:6) causing an in frame ochre stop codon in place of Glutamine 413 of SEQ ID NO:5 and lin-61(n3447) is a single base pair alteration (G to A at position 1061 of SEQ ID NO:6) causing an Serine to Asparagine missense mutation at amino acid 355 of SEQ ID NO:5. Furthermore, we identified lin-61(n3624) to be a single base pair alteration (C to T at position 394 of SEQ ID NO:6) that causes a Proline to Serine missense mutation at amino acid 133 of SEQ ID NO:5 and lin-61(n3635) to encompass a single base pair alteration (G to A at position 1137 of SEQ ID NO:76) in the splice acceptor site prior to the putative fourth exon of the protein.

Each of these alleles causes a synthetic multivulva phenotype in combination with a class A synMuv gene. This is the only phenotype we have discovered to be associated with these mutations, and the allele lin-61(n3446) has wild-type vulval morphology when not in combination with a class A synMuv gene.

Figure 11:
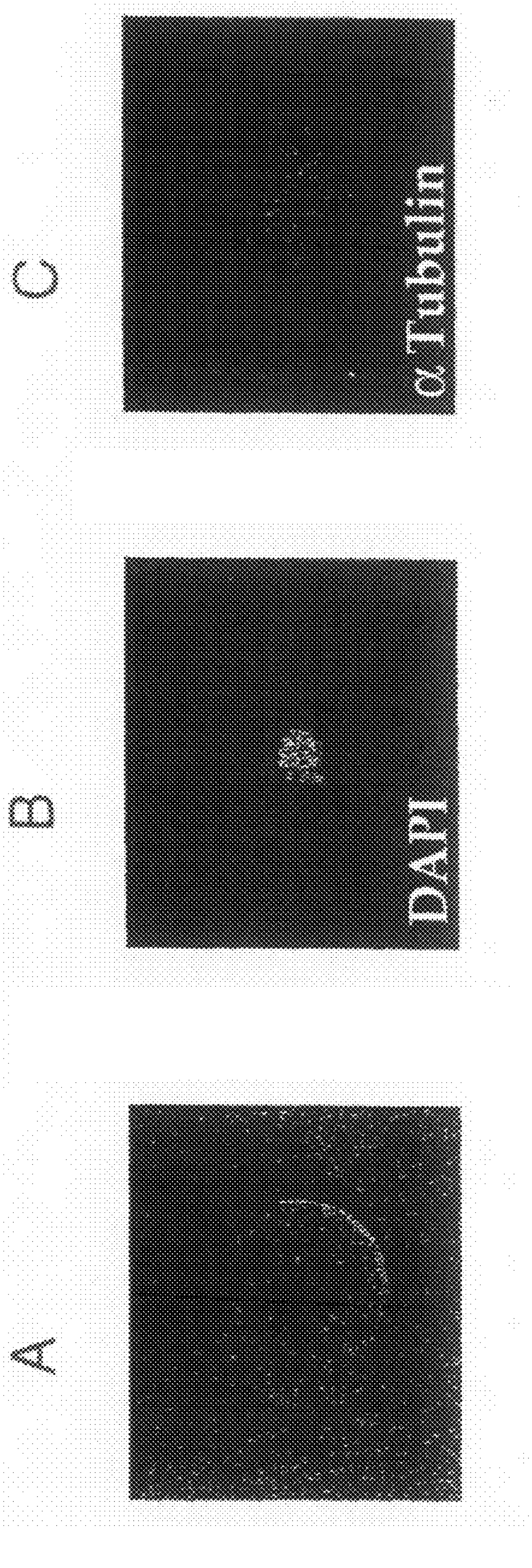
FIG. 11 shows that lin-61(RNAi) embryos display a failure in chromosome condensation during the first abortive mitotic division.
Figure 12:
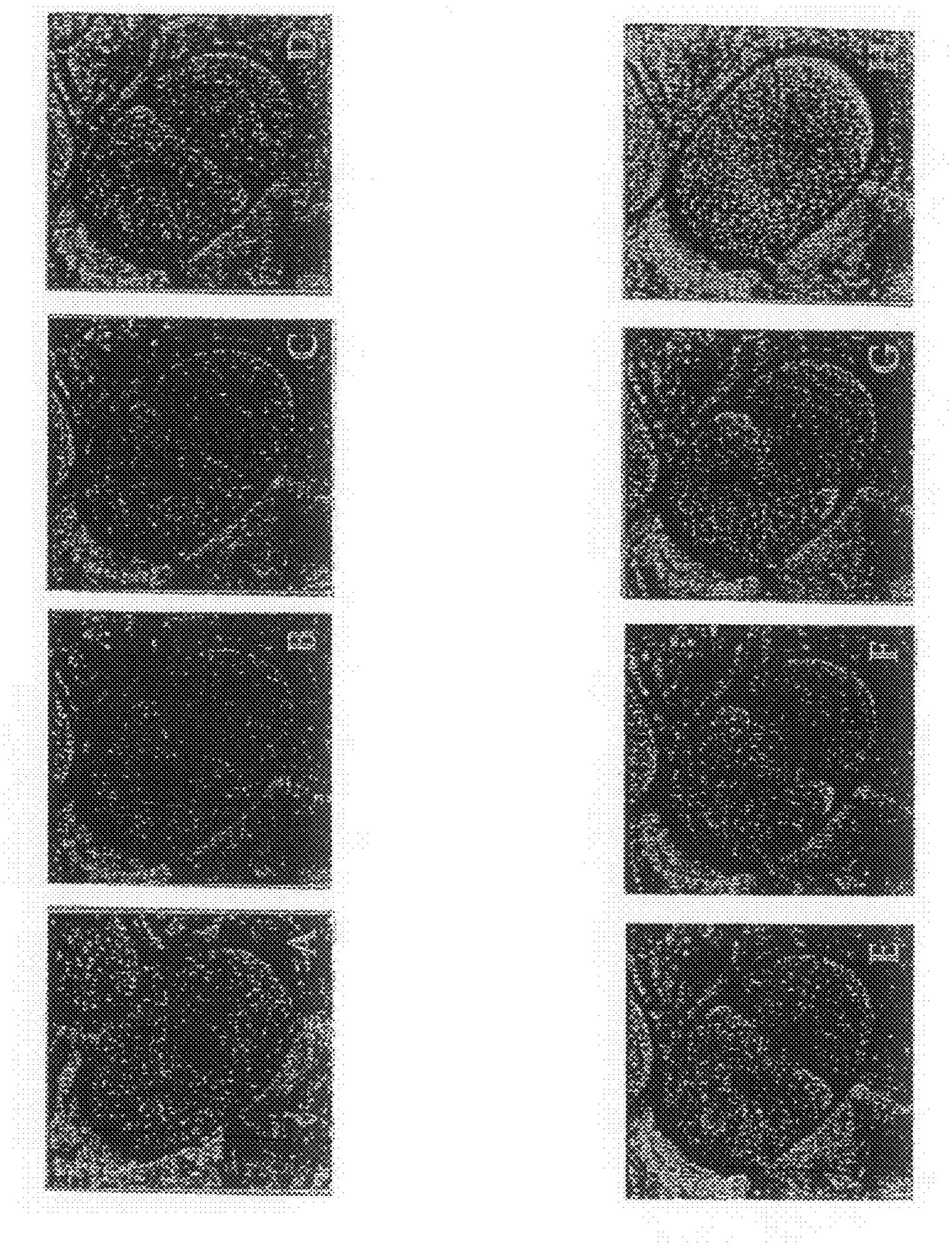
FIG. 12 shows that lin-61(RNAi) embryos display early embryonic lethality and a failure to complete cytokineses.
Figure 13:
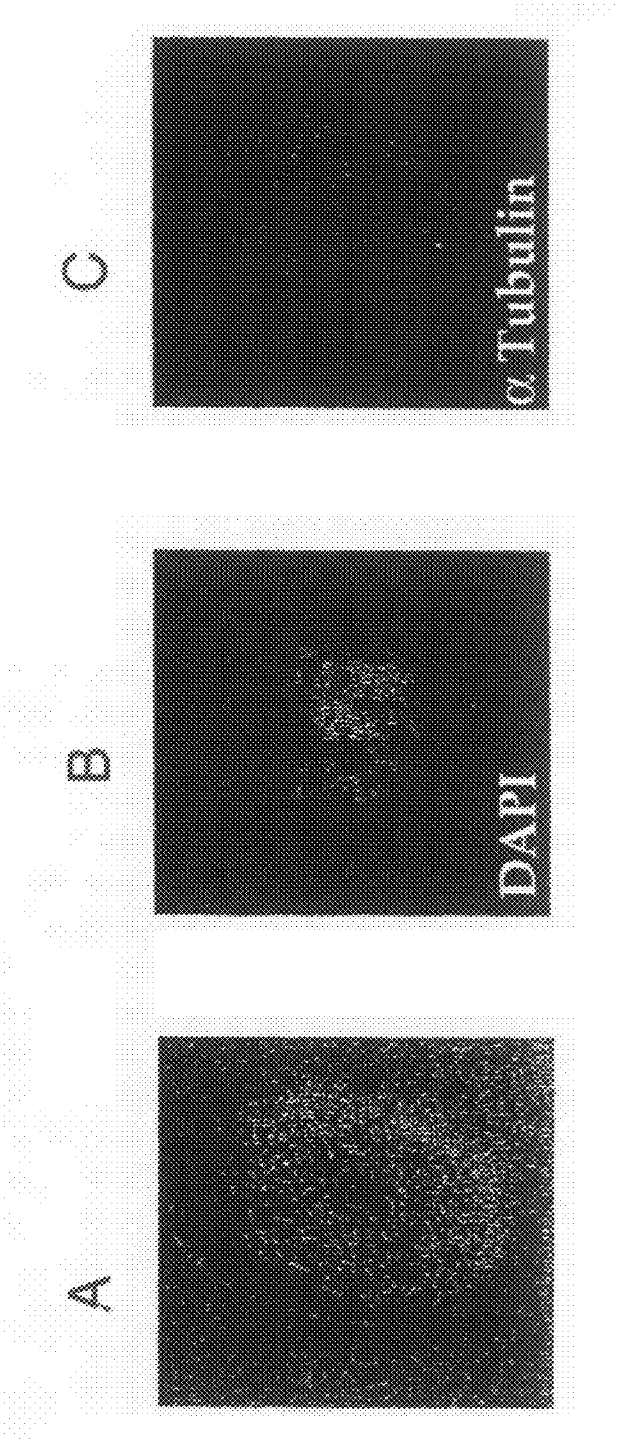
FIG. 13 shows that lin-61(RNAi) embryos arrest as multiply nucleated single cytoplasms.

None of the lin-61 alleles described above represent a clear molecular null. We have therefore sought to determine the phenotype associated with complete loss of lin-61 function by means of RNA-mediated gene interference (RNAi). When wild-type animals or animals containing a mutation in a class A synMuv gene are injected with dsRNA synthesized from cDNA corresponding to a portion of lin-61, they produce progeny which suffer from completely penetrant embryonic lethality. This phenotype includes an inability to complete cytokinesis beginning at the single cell stage (FIG. 12A). In these embryos, the cytolinetic furrow forms and, at first, ingresses essentially normally (FIG. 12B-D), but subsequently regresses (FIG. 12E-G), resulting in a polyploid single cytoplasm (FIG. 12H). DNA replication continues to occur in the absence of completed cytokinesis, and the embryos display a terminal phenotype in which high levels of DNA (as visualized by DAPI staining (FIG. 13B)) and multiple mitotic spindles (as visualized by anti-tubulin antibody staining (FIG. 13C)) are present within what is often a single cytoplasm (FIG. 13A). Moreover, embryos from lin-61 (RNAi) mothers (FIG. 11A) display a failure to condense mitotic chromosomes (as visualized by DAPI staining (FIG. 11B)). In these embryos, the mitotic spindle was visualized with an anti-tubulin antibody (FIG. 11C).

We further examined the developmental functions of lin-61 by injecting lin-61 dsRNA into RNAi defective rde-1 hermaphrodites and then mating these animals with N2 males (a technique described by Herman, Development 128:581-590, 2001). Cross progeny were then observed in an effort to gain an understanding of the phenotype produced after the reduction of zygotic lin-61 activity, while maintaining at least some maternal lin-61 function. Unlike lin-61(RNAi), this approach yields animals that reach adulthood but display a host of developmental abnormalities including uncoordinated movement, abnormal development of the male tail, and possible abnormalities in the structure of the vulva.

Based on these results we conclude that lin-61 functions in a variety of embryonic and post-embryonic developmental processes in addition to its role in vulval development and cell proliferation.

5. Characterization of Interactions among the lin-8, lin-56, lin-61 and Other synMuv Gene Products.

Standard yeast two-hybrid techniques are used to characterize the physical interactions between the lin-8, lin-56, lin-61 and other synMuv gene products, for example, as described in U.S. Ser. No. 09/220,091, incorporated herein by reference. These two-hybrid systems can also be used to detect therapeutic compounds, which disrupt the synMuv protein-protein interactions, including interactions between lin-8, lin-56, and lin-61 gene products and other synMuv gene products. For example, in a genome-wide yeast two-hybrid screen, using LIN-35 as a bait, we showed LIN-8 and LIN-35 to interact.

Interactions among the lin-8, lin-56, lin-61 and other synMuv gene products can also be examined using other methods known to one skilled in the art. For example such interactions can be determined by performing GST pull-down experiments using the appropriate fusion proteins, as described in U.S. Ser. No. 09/220,091. Alternatively, interactions may be further investigated through the use of triple mutants using the appropriate genes, as also described in U.S. Ser. No. 09/220,091.

6. Non-Vulval Phenotypes in lin-8 and lin-11 Mutants lin-8 and lin-6 are also involved in a non-vulval phenotype. During the course of a *C. elegans* screen using a cell-type specific reporter, which results in the expression of green fluorescent protein, we discovered that a class of mutants exists in which this reporter is ectopically expressed in pharyngeal tissue, especially in the posterior pharynx. We refer to this phenotype to as the "green pharynx phenotype." Further studies have revealed that loss-of-function mutations in any of several genes (lin-8, lin-13, lin-61) belonging to both the class A and class B synMuv pathways can cause the green pharynx phenotype. In the case of lin-8, all but one allele (n2376, E148K) tested exhibit the green pharynx phenotype, providing a single, distinct loss-of-function phenotype for this gene.

In addition, some of the synMuv B genes are homologues of NuRD complex components and loss-of-function mutations in other components of the NuRD chromatin remodeling complex (e.g., lin-40/egr-1 and chd-3) can also cause the green pharynx phenotype. Furthermore, the green pharynx phenotype has been observed with two distinct cell fate-specific reporters (pkd-2::gfp and lin-11::gfp).

The green pharynx phenotype is observed irrespective of whether the reporter transgene is integrated into the genome or whether it is present extra-chromosomally, indicating that chromosomal integration is not required. Additionally, when using an integrated reporter, the phenotype does not appear to be highly dependent on the site of chromosomal integration and the phenotype is observed with both low and high copy number transgenes.

Our data indicate that the synMuv A and B genes may act in similar processes, and may work together in contexts other than vulval development and provide additional evidence that lin-8, lin-13 and lin-61 act in transcriptional repression.

7. Cloning lin-8, lin-56 and lin-61 Vertebrate Genes

The invention described herein provides the identity of class A synMuv genes lin-8 and lin-56, and the class B synMuv gene lin-61. In view of what is know in the field regarding the synMuv family and its relationship to related genes in the Rb tumor suppressor pathway, we conclude that these newly cloned genes are also involved in pathways that modulate tumor suppression. It is likely that *C. elegans* lin-8, lin-56 and lin-61 genes have ortholog counterparts in vertebrates, for example mammalian genes. One skilled in the art will recognize that these orthologs can be identified using standard techniques in molecular biology, such as screening of cDNA or genomic libraries, degenerate PCR, and the like, described in, for example, Ausubel et al. (supra). Orthologs can also be identified using computer-based search programs such as BLAST and dbEST to isolate expressed sequence tags (ESTs) with regions of similarity or identity to a lin-8, lin-56 or lin-61 gene.

Vertebrate counterparts of *C. elegans* lin-8, lin-56 and lin-61 are candidate tumor suppressor genes. Thus, one can screen for mutations in the human homologs of these genes in patients diagnosed with cancer or in immortal cell lines. Similarly, the polypeptides encoded by these genes are candidate targets for anti-cancer drugs. A drug which increases synMuv polypeptide activity, for example, LIN-8, LIN-56, or LIN-61 biological activity, may decrease proliferation of tumor cells. In addition, polypeptides which interact with other synMuv polypeptides or which regulate synMuv gene expression are also candidate tumor suppressors; these polypeptides can be isolated using standard techniques, as described herein or, for example, in Ausubel et al. (supra).

8. LIN-8, LIN-56, or LIN-61 Polypeptide Expression

A lin-8, lin-56, or lin-61 nucleic acid sequence may be expressed in a prokaryotic or eukaryotic cell. In addition, it may be desirable to express the nucleic acid sequence under the control of an inducible promoter for the purposes of polypeptide production.

In general, LIN-8, LIN-56, or LIN-61 polypeptides may be produced by transformation of a suitable host cell with all or part of a LIN-8, LIN-56, or LIN-61-encoding cDNA fragment (e.g., the cDNAs described above) in a suitable expression vehicle.

Those skilled in the field of molecular biology will understand that any of a wide variety of expression systems may be used to provide the recombinant protein. The precise host cell used is not critical to the invention. The LIN-8, LIN-56, or LIN-61 polypeptide may be produced in a prokaryotic host (e.g., *E. coli*) or in a eukaryotic host (e.g., nematodes, *Saccharomyces cerevisiae*, insect cells, e.g., Sf-21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al. (supra)). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Palo Alto, Calif.). If desired, this system may be used in conjunction with other protein expression techniques, for example, the myc tag approach described by Evan et al. (Mol. Cell. Biol. 5:3610-3616, 1985).

Alternatively, a LIN-8, LIN-56, or LIN-61 polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding a LIN-8, LIN-56, or LIN-61 polypeptide is cloned into an expression vector which includes the dihydrofolate reductase (DHFR) gene. Integration of the plasmid, and, therefore, the LIN-8, LIN-56, or LIN-61 polypeptide-encoding gene, into the host cell chromosome is selected for by inclusion of 0.01-300 μM methotrexate in the cell culture medium (as described in Ausubel et al. (supra)). This dominant selection can be accomplished in most cell types and recombinant protein expression can be increased by DHFR-mediated amplification of the transfected gene. In addition, methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al. (supra)). Any of the host cells described above or, preferably, a DHFR-deficient CHO cell line (e.g., CHO DHFR$^{(-)}$ cells, ATCC Accession No. CRL 9096) are among the host cells preferred for DHFR selection of a stably-transfected cell line or DHFR-mediated gene amplification.

Once the recombinant LIN-8, LIN-56, or LIN-61 protein is expressed, it is isolated, e.g., using affinity chromatography. In one example, an anti-LIN-8, LIN-56, or LIN-61 protein antibody (e.g., produced as described herein) may be immobilized on a column and used to isolate the LIN-8, LIN-56, or LIN-61 protein. Lysis and fractionation of LIN-8, LIN-56, or LIN-61 protein-harboring cells prior to affinity chromatography may be performed by standard methods (see, e.g., Ausubel et al. (supra)).

Once isolated, the recombinant protein can, if desired, be further purified, e.g., by high pressure liquid chromatography (see, e.g., Fisher, *Laboratory Techniques In Biochemistry And Molecular Biology*, eds., Work and Burdon, Elsevier, 1980).

Polypeptides of the invention, particularly short LIN-8, LIN-56, or LIN-61 protein fragments, can also be produced by chemical synthesis (e.g., by the methods described in *Solid Phase Peptide Synthesis,* 2nd ed., 1984, The Pierce Chemical Co., Rockford, Ill.).

These general techniques of polypeptide expression and purification can also be used to produce and isolate useful LIN-8, LIN-56, or LIN-61 fragments or analogs (described herein).

9. Anti-LIN-8, LIN-56, or LIN-61 Antibodies

In general, to generate a LIN-8, LIN-56, or LIN-61-specific antibody, a lin-8, lin-56, or lin-61 coding sequence may be expressed as a C-terminal fusion with glutathione S-transferase (GST) (Smith et al., Gene 67:31-40, 1988). The fusion protein can be purified on glutathione-sepharose beads, eluted with glutathione cleaved with thrombin (at the engineered cleavage site), and purified to the degree necessary for immunization of rabbits. Primary immunizations can be carried out with Freund's complete adjuvant and subsequent immunizations with Freund's incomplete adjuvant. Antibody titres are monitored by Western blot and immunoprecipitation analyses using the thrombin-cleaved LIN-8, LIN-56, or LIN-61 polypeptide fragment of the GST-LIN-8, -LIN-56, or -LIN-61 fusion protein. Immune sera are affinity purified using, for example, CNBr—Sepharose-coupled LIN-8, LIN-56, or LIN-61 protein. Antiserum specificity is determined using a panel of unrelated GST proteins (including GSTp53, Rb, HPV-16 E6, and E6-AP) and GST-trypsin (which was generated by PCR using known sequences).

As an alternate or adjunct immunogen to GST fusion proteins, peptides corresponding to relatively unique regions of LIN-8, LIN-56, or LIN-61 may be generated and coupled to keyhole limpet hemocyanin (KLH) through an introduced C-terminal lysine. Antiserum to each of these peptides is similarly affinity purified on peptides conjugated to BSA, and specificity tested in ELISA and Western blots assays using peptide conjugates, and by Western blot and immunoprecipitation techniques using LIN-8, LIN-56, or LIN-61 expressed as a GST fusion protein.

Alternatively, monoclonal antibodies may be prepared using the LIN-8, LIN-56, or LIN-61 proteins described above and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., In *Monoclonal Antibodies and T Cell Hybridomas*, Elsevier, N.Y., 1981; Ausubel et al., (supra)). Once produced, monoclonal antibodies are also tested for specific recognition by Western blot or immunoprecipitation analysis (by the methods described in Ausubel et al. (supra). Antibodies which specifically recognize LIN-8, LIN-56, or LIN-61 are considered to be useful in the invention; such antibodies may be used, e.g., in an immunoassay to monitor the level of LIN-8, LIN-56, or LIN-61 produced by an animal (for example, to determine the amount or subcellular location of LIN-8, LIN-56, or LIN-61).

Preferably antibodies of the invention are produced using fragments of the LIN-8, LIN-56, or LIN-61 polypeptide that are positioned outside highly conserved regions and appear likely to be antigenic, by criteria such as those provided by the Peptidestructure program of the Genetics Computer Group Sequence Analysis Package (Program Manual for the GCG Package, Version 7, 1991) using the algorithm of Jameson and Wolf (CABIOS 4:181, 1988). In one specific example, such fragments are generated by standard PCR techniques and cloned into the pGEX expression vector (Ausubel et al. (supra). Fusion proteins are expressed in *E. coli* and purified using a glutathione agarose affinity matrix, as described in Ausubel et al. (supra). To attempt to minimize the potential problems of low affinity or specificity of antisera, two or three such fusions are generated for each polypeptide, and each fusion is injected into at least two rabbits. Antisera are raised by injections in a series, preferably including at least three booster injections.

To demonstrate the utility of this approach, we generated polyclonal antibodies against a fusion of full-length LIN-8 with maltose binding protein (MBP) (see Example 1 for the detailed protocol used). In order to increase the sensitivity of the antibodies, they were affinity-purified against a GST::LIN-8 fusion, and pre-adsorbed with extract from lin-8 (n2731) worms.

Figure 9:
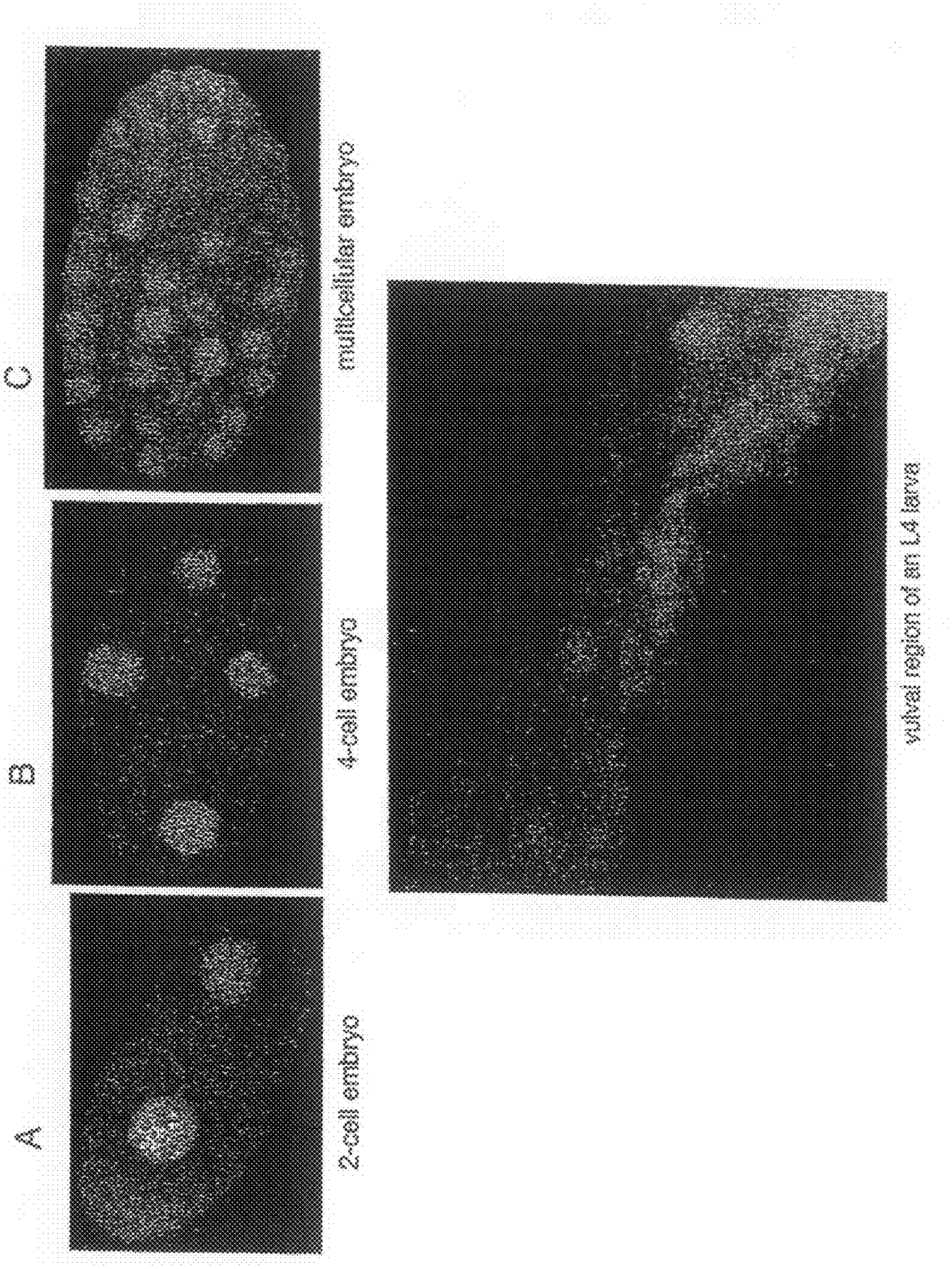
FIG. 9 shows that LIN-56 is localized to the nuclei of wild-type *C. elegans* embryos (Panels A-C), larvae (Panel D), and adults. The staining shown was obtained with affinity-purified and pre-adsorbed rabbit polyclonal antibody HM1923.
Figure 10:
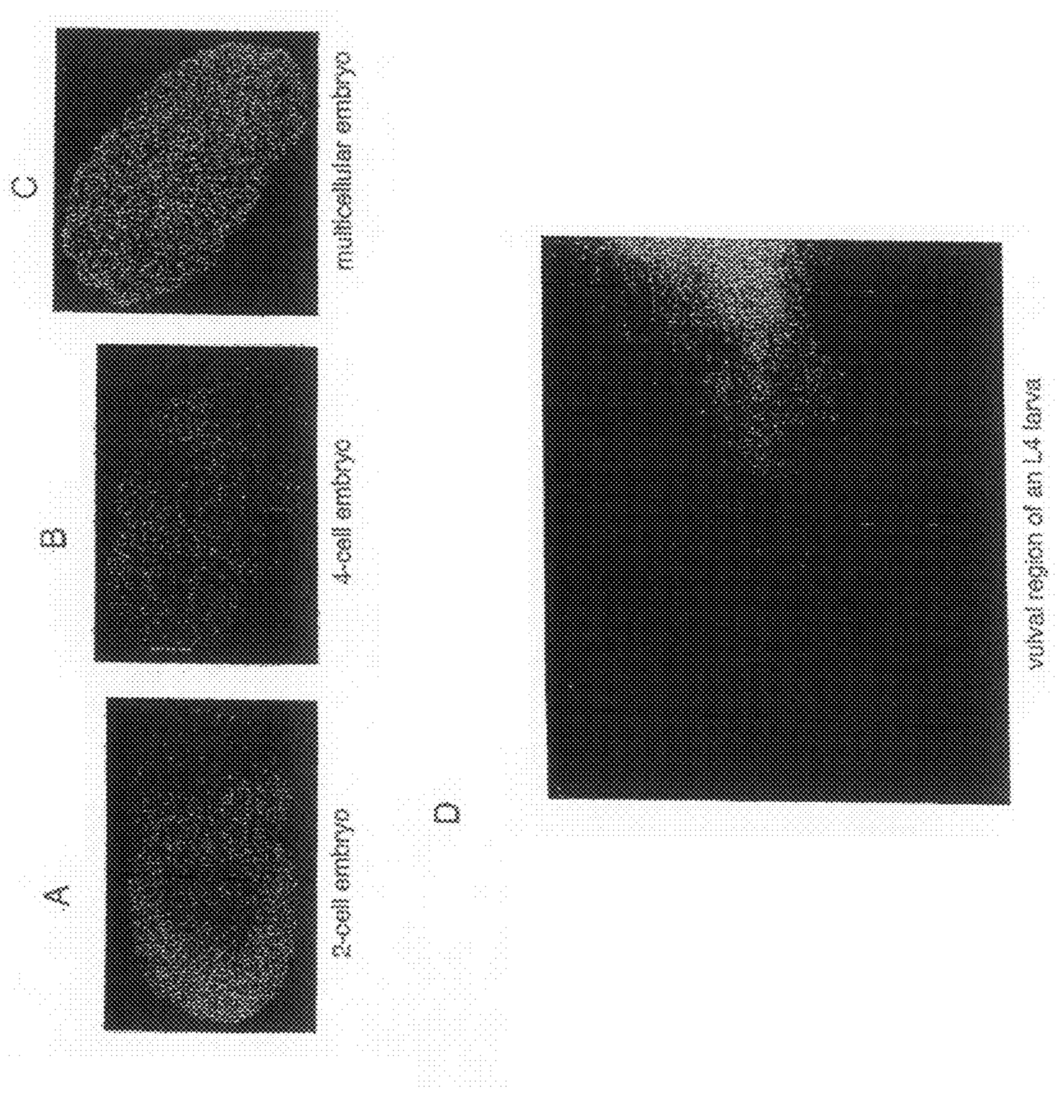
FIG. 10 shows that LIN-56 staining is absent in lin-56 (n2728) embryos (Panels A-C), larvae (Panel D), and adults. The staining shown was obtained with affinity-purified and pre-adsorbed rabbit polyclonal antibody HM1923.

In addition, the antibodies that we generated against LIN-56 (see Example 2) were also affinity purified and pre-adsorbed with extract from lin-56(n2728) worms. We used one of these anti-LIN-56 antibodies (HM1923) for Western analysis and for wholemount staining. This antibody recognizes a doublet in wild-type but not lin-56(n2728) worm extracts on Western analysis and the proteins in this doublet fractionate specifically with nuclear material. Furthermore, wholemount staining with this antibody reveals that lin-56 is expressed in the nuclei of most if not all cells throughout development and adulthood (FIG. 9 A-D). We also stained lin-56(n2728) embryos, larvae, and adults to show that the HM1923 antibody is specific for LIN-56. As is seen in FIG. 10, LIN-56 staining is absent in LIN-56 mutant worms, indicating that the antibody is specific for LIN-56.

In addition, LIN-56 appears to be absent from nuclei during part of the cell cycle, probably as a result of nuclear membrane breakdown. Furthermore, LIN-56 expression and localization appear wild-type in the synMuv A lin-8 and lin-38 mutants, but the nuclear expression of LIN-56 appears severely reduced or even absent in lin-15A(n767) and lin-15AB(n309) mutants. By Western analysis, LIN-56 protein levels do in fact appear reduced in lin-15A(n767) worm extracts, and the ratio of the bands in the detected doublet may even be altered.

10. Identification of Molecules that Modulate LIN-8, LIN-56, or LIN-61 Polypeptide Expression Isolation of lin-8, lin-56, or lin-61 cDNAs also facilitates the identification of molecules which increase or decrease LIN-8, LIN-56, or LIN-61 expression. According to one approach, candidate molecules are added at varying concentrations to the culture medium of cells or nematodes expressing LIN-8, LIN-56, or LIN-61, lin-8, lin-56, or lin-61 expression is then measured, for example, by standard Northern blot analysis (Ausubel et al. (supra)) using a lin-8, lin-56, or lin-61 cDNA (or cDNA fragment) as a hybridization probe (see also Table III). The level of lin-8, lin-56, or lin-61 expression in the presence of the candidate molecule is compared to the level measured for the same cells in the same culture medium but in the absence of the candidate molecule. When nematodes are being used, the phenotypes associated with the synMuv pathway may be utilized as the primary screen for alteration in polypeptide expression.

If desired, the effect of candidate modulators on expression may, in the alternative, be measured at the level of LIN-8, LIN-56, or LIN-61 polypeptide production using the same general approach and standard immunological detection techniques, such as Western blotting or immunoprecipitation with a LIN-8, LIN-56, or LIN-61-specific antibody (for example, the LIN-8, LIN-56, or LIN-61 antibody described herein).

Candidate modulators may be purified (or substantially purified) molecules or may be one component of a mixture of compounds (e.g., an extract or supernatant obtained from cells; Ausubel et al. (supra)). In a mixed compound assay, LIN-8, LIN-56, or LIN-61 expression is tested against progressively smaller subsets of the candidate compound pool (e.g., produced by standard purification techniques, e.g., HPLC or FPLC) until a single compound or minimal compound mixture is demonstrated to modulate LIN-8, LIN-56, or LIN-61 expression.

Alternatively, or in addition, candidate compounds may be screened for those, which modulate LIN-8, LIN-56, or LIN-61 cell proliferation. In this approach, the degree of cell proliferation, or the LIN-8, LIN-56, or LIN-61 phenotype in the presence of a candidate compound is compared to the degree of cell proliferation in its absence, under equivalent conditions. Again, such a screen may begin with a pool of candidate compounds, from which one or more useful modulator compounds are isolated in a step-wise fashion. Cell proliferation may be measured by any standard assay.

Candidate LIN-8, LIN-56, or LIN-61 modulators include peptide as well as non-peptide molecules (e.g., peptide or non-peptide molecules found, e.g., in a cell extract, mammalian serum, or growth medium on which mammalian cells have been cultured).

Modulators found to be effective at the level of LIN-8, LIN-56, or LIN-61 expression or biological activity may be confirmed as useful in animal models and, if successful, may be used as anti cancer therapeutics to increase or decrease cell proliferation.

11. lin-8, lin-56, or lin-61 Therapy

Because expression levels of lin-8, lin-56, or lin-61 genes correlate with the levels of cell proliferation, such genes also find use in gene therapy to modulate cell proliferation.

Retroviral vectors, adenoviral vectors, adeno-associated viral vectors, or other viral vectors with the appropriate tropism for cells likely to be involved in the cell proliferation disease may be used as a gene transfer delivery system for a therapeutic lin-8, lin-56, or lin-61 gene construct Numerous vectors useful for this purpose are generally known in the art (Miller, Human Gene Therapy 5-14, 1990; Friedman, Science 244:1275-1281, 1989; Eglitis and Anderson, BioTechniques 6:608-614, 1988; Tolstoshev and Anderson, Current Opinion in Biotechnology 1:55-61, 1990; Sharp, The Lancet 337: 1277-1278, 1991; Cornetta et al., Nucleic Acid Research and Molecular Biology 36:311-322, 1987; Anderson, Science 226:401-409, 1984; Moen, Blood Cells 17:407-416, 1991; and Miller and Rosman, BioTechniques 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches may also be employed for the introduction of therapeutic DNA into cells otherwise predicted to undergo insufficient or excess cell proliferation. For example, lin-8, lin-56, or lin-61 may be introduced into a cell by the techniques of lipofection (Felgner et al., Proc. Natl. Acad. Sci. USA 84:7413, 1987; Ono et al., Neuroscience Lett. 117: 259, 1990; Brigham et al., Am. J. Med. Sci. 298:278, 1989; Staubinger and Papahadjopoulos, Meth. Enz. 101:512, 1983); asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic lin-8, lin-56, or lin-61 DNA construct, or an antisense nucleic acid, is preferably applied to the site of the predicted cell proliferation event (for example, by injection), but may also be applied to tissue in the vicinity of the predicted event or even to a blood vessel supplying the cells predicted to undergo insufficient or excess cell proliferation.

In the gene therapy constructs, lin-8, lin-56, or lin-61 cDNA expression is directed from any suitable promoter (e.g., the human cytomegalovirus, simian virus 40, or metallothionein promoters), and its production is regulated by any desired regulatory element. For example, if desired, enhancers known to direct preferential gene expression in a particular cell may be used to direct lin-8, lin-56, or lin-61 expression. Such enhancers include, without limitation, those enhancers which are characterized as tissue or cell specific in their expression.

Alternatively, if a lin-8, lin-56, or lin-61 genomic clone is utilized as a therapeutic construct (for example, following its isolation by hybridization with the lin-8, lin-56, or lin-61 cDNA described above), lin-8, lin-56, or lin-61 expression is regulated by its cognate regulatory sequences or, if desired, by regulatory sequences derived from a heterologous source, e.g., any of the promoters or regulatory elements described above.

Less preferably, lin-8, lin-56, or lin-61 gene therapy is accomplished by direct administration of the lin-8, lin-56, or lin-61 mRNA to a cell predicted to undergo excess or insufficient cell proliferation. This mRNA may be produced and isolated by any standard technique, but is most readily produced by in vitro transcription using a lin-8, lin-56, or lin-61 cDNA under the control of a high efficiency promoter (e.g., the T7 promoter). Administration of lin-8, lin-56, or lin-61 mRNA to malignant cells is carried out by any of the methods for direct nucleic acid administration described above.

Ideally, the production of a LIN-8, LIN-56, or LIN-61 polypeptide by any gene therapy approach described above results in a cellular level of LIN-8, LIN-56, or LIN-61 that is at least equivalent to the normal, cellular level of LIN-8, LIN-56, or LIN-61 in an unaffected individual. Treatment by any lin-8, lin-56, or lin-61-mediated gene therapy approach may be combined with more traditional therapies.

Another therapeutic approach included within the invention involves direct administration of recombinant LIN-8, LIN-56, or LIN-61 protein, either to the site of a predicted or desirable cell proliferation event (for example, by injection) or systemically by any conventional recombinant protein administration technique. The actual dosage of LIN-8, LIN-56, or LIN-61 administered depends on a number of factors, including the size and health of the individual patient, but, generally, between 0.1 mg and 100 mg, inclusive, are administered per day to an adult in any pharmaceutically-acceptable formulation.

The nucleic acids of the present invention may also be utilized in plant cells. Such sequences may be expressed in plant cells, and used, for example, to promote plant survival or growth (e.g., by providing disease resistance).

12. Administration of LIN-8, LIN-56, or LIN-61 Polypeptides, lin-8, lin-56, or lin-61 Nucleic Acid Sequences, or Modulators of LIN-8, LIN-56, or LIN-61 Synthesis or Function A LIN-8, LIN-56, or LIN-61 polypeptide, nucleic acid sequence, or modulator may be administered with a pharmaceutically-acceptable diluent, carrier, or excipient, in unit dosage form. Conventional pharmaceutical practice may be employed to provide suitable formulations or compositions to administer LIN-8, LIN-56, or LIN-61 to patients suffering from, or presymptomatic for, a LIN-8, LIN-56, or LIN-61, or synMuv-associated cancer. Any appropriate route of administration may be employed, for example, parenteral, intravenous, subcutaneous, intramuscular, intracranial, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in Remington's Pharmaceutical Sciences (($18^{th}$ edition), ed. A Gennaro, 1990, Mack Publishing Company, Easton, Pa.). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for LIN-8, LIN-56, or LIN-61 polypeptides, nucleic acid sequences or modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a LIN-8, LIN-56, or LIN-61 polypeptide, nucleic acid sequence, or modulatory compound may be combined with more traditional therapies for the disease such as surgery, radiation, or chemotherapy for cancers.

13. Detection of A Condition Involving Altered Cell Proliferation or an Increased Likelihood of Developing a Cell Proliferation Disease LIN-8, LIN-56, or LIN-61 polypeptides and nucleic acid sequences find diagnostic use in the detection or monitoring of conditions involving aberrant levels of cell proliferation. A decrease or increase in the level of LIN-8, LIN-56, or LIN-61 production may provide an indication of a deleterious condition. Levels of LIN-8, LIN-56, or LIN-61 expression may be assayed by any standard technique. For example, its expression in a biological sample (e.g., a biopsy) may be monitored by standard Northern blot analysis, using, for example, probes designed from lin-8, lin-56, or lin-61 nucleic acid sequences, or from nucleic acid sequences that hybridize to a lin-8, lin-56, or lin-61 nucleic acid sequence. Measurement of such expression may be aided by PCR (see, e.g., Ausubel et al. (supra); *PCR Technology: Principles and Applications for DNA Amplification*, ed., H. A Ehrlich, Stockton Press, NY; and Yap and McGee, Nucl. Acids Res. 19:4294, 1991).

Alternatively, a patient sample may be analyzed for one or more mutations in the lin-8, lin-56, or lin-61 sequences using a mismatch detection approach. Generally, these techniques involve PCR amplification of nucleic acid from the patient sample, followed by identification of the mutation (i.e., mismatch) by either altered hybridization, aberrant electrophoretic gel migration, binding or cleavage mediated by mismatch binding proteins, or direct nucleic acid sequencing. Any of these techniques may be used to facilitate mutant lin-8, lin-56, or lin-61 detection, and each is well known in the art (see, for example, Orita et al., Proc. Natl. Acad. Sci. USA 86:2766-2770, 1989; and Sheffield et al., Proc. Natl. Acad. Sci. USA 86:232-236, 1989).

In yet another approach, immunoassays are used to detect or monitor a LIN-8, LIN-56, or LIN-61 polypeptide in a biological sample. LIN-8, LIN-56, or LIN-61-specific polyclonal or monoclonal antibodies (produced as described above) may be used in any standard immunoassay format (e.g., ELISA, Western blot, or RIA assay) to measure LIN-8, LIN-56, or LIN-61 polypeptide levels; again comparison is to wild-type LIN-8, LIN-56, or LIN-61 levels, and an increase or decrease in LIN-8, LIN-56, or LIN-61 production is indicative of a condition involving altered cell proliferation. Examples of immunoassays are described, e.g., in Ausubel et al. (supra). Immunohistochemical techniques may also be utilized for LIN-8, LIN-56, or LIN-61 detection. For example, a tissue sample may be obtained from a patient, and a section stained for the presence of LIN-8, LIN-56, or LIN-61 using an anti-LIN-8, LIN-56, or LIN-61 antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (supra).

In one preferred example, a combined diagnostic method may be employed that begins with an evaluation of LIN-8, LIN-56, or LIN-61 polypeptide production (for example, by immunological techniques or the protein truncation test (Hogerrorst et al., Nature Genetics 10:208-212, 1995) and also includes a nucleic acid-based detection technique designed to identify more subtle lin-8, lin-56, or lin-61 mutations (for example, point mutations). As described above, a number of mismatch detection assays are available to those skilled in the art, and any preferred technique may be used (see above). By this approach, mutations in lin-8, lin-56, or lin-61 may be detected that either result in loss of LIN-8, LIN-56, or LIN-61 expression or biological activity.

Mismatch detection assays also provide the opportunity to diagnose a lin-8, lin-56, or lin-61-mediated predisposition to diseases of cell proliferation. For example, a patient heterozygous for a lin-8, lin-56, or lin-61 mutation may show no clinical symptoms and yet possess a higher than normal probability of developing one or more types of diseases. Given this diagnosis, a patient may take precautions to minimize their exposure to adverse environmental factors (for example, UV exposure or chemical mutagens) and to carefully monitor their medical condition (for example, through frequent physical examinations). This type of lin-8, lin-56, or lin-61 diagnostic approach may also be used to detect lin-8, lin-56, or lin-61 mutations in prenatal screens.

The lin-8, lin-56, or lin-61 diagnostic assays described above may be carried out using any biological sample (for example, any biopsy sample or bodily fluid or tissue) in which lin-8, lin-56, or lin-61 is normally expressed. Identification of a mutant lin-8, lin-56, or lin-61 gene may also be assayed using these sources for test samples. Alternatively, a lin-8, lin-56, or lin-61 mutation, particularly as part of a diagnosis for predisposition to lin-8, lin-56, or lin-61-associated proliferative disease, may be tested using a DNA sample from any cell for example, by mismatch detection techniques; preferably, the DNA sample is subjected to PCR amplification prior to analysis.

The following examples are meant to illustrate the invention and should not be construed as limiting.

EXAMPLES

Example 1

Generation of Rabbit and Guinea Pig Polyclonal Antibodies Against LIN-8

We made a fusion protein of full-length LIN-8 with MBP and had Covance (Richmond, Calif.) produce LIN-8 polyclonal antibodies using two rabbits and two guinea pigs. However, anyone skilled in the art may generate antibodies against LIN-8 using the following protocol.

New Zealand White Female Rabbits were bled prior to injection of the antigen, for later use as a control in establishing background reactivity of the serum. Following the prebleed, the rabbits were injected subcutaneously at multiple sites with 250 μg protein and 0.5 mL Freund's Complete Adjuvant (FCA). Three weeks later, the rabbits received a subcutaneous, dorsal, boost injection of 125 μg protein with 1.0 mL Freund's Incomplete Adjuvant (FIA). The first test bleed was performed 11 days later, followed by a second subcutaneous, dorsal boost injection of 125 μg protein and 1.0 mL FIA 9 days after the test bleed. A second test bleed was performed 11 days after the second boost, followed by a third subcutaneous, dorsal boost of 125 μg protein and 1.0 mL FIA 10 days after the second test bleed. The first production bleed was performed 10 days after the third boost, followed by a fourth subcutaneous, dorsal boost of 125 μg and 1.0 mL FIA 10 days after the first production bleed. A second production bleed was performed 11 days after the fourth boost, followed by a fifth subcutaneous, dorsal boost of 125 μg and 1.0 mL FIA 10 days after the second production bleed. A third production bleed was performed 11 days after the fifth boost, followed by exsanguination after 6 days.

The protocol used to produce LIN-8 antibodies in guinea pigs closely follows the one outlined for rabbits above. Dunkin Hartley Guinea Pig were used and prebled prior to subcutaneous and intradermal injection of 200 μg protein and 1.0 mL FCA. Three weeks after the primary injection, the guinea pigs received a boost injection of 100 μg protein and 0.5 mL FIA, subcutaneously in the neck. After 11 days, the first test bleed was performed, followed 10 days later by a second boost of 100 μg protein and 0.5 mL FIA, subcutaneously in the neck. The second test bleed was performed after 11 days, followed 10 days later by a third boost of 100 μg protein and 0.5 mL FIA, subcutaneously in the neck. The first production bleed was performed 11 days after the third boost, followed 10 days later by a fourth subcutaneous, dorsal boost of 100 μg protein and 0.5 mL FIA. The second production bleed followed 11 days later and a fifth boost of 100 μg protein and 0.5 mL FIA was performed after 10 days. The third production bleed was performed 11 days later, followed by exsanguination after 6 days.

Generally, polyclonal antibodies are affinity purified to increase their specificity. In addition, the polyclonal antibody may be depleted of any components that do not specifically bind to the protein of interest by pre-adsorbing the antibody with an extract made from tissue that lacks the protein of interest. For example, an extract from lin-8(n2731) worms may be used to remove any antibodies that bind worm proteins besides LIN-8.

Example 2

Generation of Rabbit and Rat Polyclonal Antibodies Against LIN-56

We made a fusion protein of full-length LIN-56 with GST and had Covance (Richmond, Calif.) produce LIN-56 polyclonal antibodies using two rabbits and two rats. However, anyone skilled in the art may generate antibodies against LIN-56 using the following protocol.

New Zealand White Female Rabbits were bled prior to intradermal injection in the back with 250 μg protein and 0.5 mL FCA. Three weeks later, the rabbits received a subcutaneous nodal (groin and pit) area boost injection of 125 μg protein with 0.5 mL FIA. The first test bleed was performed 10 days later, followed by a second subcutaneous boost injection of 125 μg protein and 0.5 mL FIA in the neck, 11 days after the test bleed. A second test bleed was performed 10 days after the second boost, followed by a third subcutaneous, dorsal boost of 125 μg protein and 1.0 mL FIA 11 days after the second test bleed. The first production bleed was performed 10 days after the third boost, followed by a fourth subcutaneous nodal area (groin and pit) boost of 125 μg and 1.0 mL FIA 10 days after the first production bleed. A second production bleed was performed 11 days after the fourth boost, followed by a fifth subcutaneous, dorsal boost of 125 μg and 1.0 mL FIA 11 days after the second production bleed. A third production bleed was performed 10 days after the fifth boost, followed by exsanguination after 10 days.

The protocol used to produce LIN-56 antibodies in rats closely follows the one outlined for rabbits above. SD rats were used and prebled prior to subcutaneous injection of 200 μg protein and 0.4 mL FCA, in the neck. Three weeks after the primary injection, the rats received a boost injection of 100 μg protein and 0.4 mL FIA, subcutaneously in the neck. After 10 days, the first test bleed was performed, followed 11 days later by a second boost of 100 μg protein and 0.4 mL FIA, subcutaneously in the neck. The second test bleed was performed after 10 days, followed 11 days later by a third boost of 100 μg protein and 0.4 mL FIA, subcutaneously in the neck. The first production bleed was performed 10 days after the third boost, followed 11 days later by a fourth subcutaneous, dorsal boost of 100 μg protein and 0.4 mL FIA. The second production bleed followed 10 days later and a fifth boost of 100 μg protein and 0.4 mL FIA was performed after 11 days. The third production bleed was performed 10 days later, followed by exsanguination after 10 days.

OTHER EMBODIMENTS

While the invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and which may be applied to the essential features hereinbefore set forth.

All publications and patent applications mentioned in this specification are herein incorporated by reference to the same extent as if each independent publication or patent application was specifically and individually indicated to be incorporated by reference.

What is claimed is:

1. A method of identifying a candidate molecule for decreasing cell proliferation, wherein said method comprises:

(i) contacting a cell expressing a human homolog of a *C. elegans* lin-61 nucleic acid with said candidate molecule, wherein said human homolog encodes an amino acid sequence at least 99% identical to the amino acid sequence of SEQ ID NO: 68;

(ii) measuring the level of expression of said human homolog in said contacted cell;

(iii) comparing the level of expression of said human homolog in said contacted cell and a control cell, wherein said control cell is cultured in the absence of the candidate molecule; wherein an increase in said level of expression identifies a candidate molecule for decreasing cell proliferation.

2. The method of claim 1, wherein the human homolog encodes the amino acid sequence of SEQ ID NO: 68.

3. The method of claim 1, wherein said measuring is performed by hybridization.

4. The method of claim 1, wherein said cell expressing said human homolog is a mammalian cell.

5. The method of claim 4, wherein said mammalian cell is a human cell.

6. The method of claim 1, wherein said cell is a transformed cell.

7. The method of claim 1, wherein said candidate molecule is a peptide molecule.

8. The method of claim 7, wherein said peptide molecule is present in a cell extract.

* * * * *

UNITED STATES PATENT AND TRADEMARK OFFICE

CERTIFICATE OF CORRECTION

PATENT NO. : 7,670,778 B2
APPLICATION NO. : 11/973006
DATED : March 2, 2010
INVENTOR(S) : Horvitz et al.

It is certified that error appears in the above-identified patent and that said Letters Patent is hereby corrected as shown below:

Title Page, Item (56) OTHER PUBLICATIONS, in Clark et al., replace "*Caenothabditis*" with --*Caneorhabditis*--;

OTHER PUBLICATIONS, in Fay et al., replace "Redunancy" with --Redundancy--.

Column 1, Line 55, replace "LET60" with --LET-60--;

Line 65, replace "multivalva" with --multivulva--.

Column 9, Line 33, replace "tuncated" with --truncated--;

Line 59, replace "acids SEQ ID NO:5" with --acids of SEQ ID NO: 5--.

Column 13, Lines 62-63, replace "promoterdependent" with --promoter-dependent--.

Column 15, Line 9, replace "cytokineses" with --cytokinesis--;

Line 63, replace "lin-4" with --lin-8--.

Column 19, Line 30, replace "lin-11" with --lin-61--;

Line 67, replace "know in" with --known in--.

Signed and Sealed this
Twenty-fifth Day of January, 2011

David J. Kappos
*Director of the United States Patent and Trademark Office*

UNITED STATES PATENT AND TRADEMARK OFFICE

CERTIFICATE OF CORRECTION

| | |
|---|---|
| PATENT NO. | : 7,670,778 B2 |
| APPLICATION NO. | : 11/973006 |
| DATED | : March 2, 2010 |
| INVENTOR(S) | : Horvitz et al. |

It is certified that error appears in the above-identified patent and that said Letters Patent is hereby corrected as shown below:

Column 1, lines 19-21: Replace

"The present research was supported by a grant from the National Institutes of Health (Number GM 24663). The U.S. government has certain rights to this invention"

with

--This invention was made with government support under grant number R37 GM024663 awarded by the NIH. This government has certain rights to this invention--.

Signed and Sealed this
Twenty-first Day of June, 2011

David J. Kappos
*Director of the United States Patent and Trademark Office*

SEQUENCE LISTING

```
<160> NUMBER OF SEQ ID NOS: 78

<210> SEQ ID NO 1
<211> LENGTH: 386
<212> TYPE: PRT
<213> ORGANISM: Caenorhabditis elegans

<400> SEQUENCE: 1

Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270
```

-continued

```
Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385


<210> SEQ ID NO 2
<211> LENGTH: 1276
<212> TYPE: DNA
<213> ORGANISM: Caenorhabditis elegans

<400> SEQUENCE: 2

agaatctgcc aaaatgtcaa agataaagac acattccact ggctcaaaac ggacggtacc      60

attctacaag ctgccaccgc ccgtgccact tccaccactc ccgccacccg atccaacccg     120

gtacttctcg acggaaaagt acatcgcact gagcaaagat gagaaattca aatttgatga     180

ttacgatgtg aatgatgaga cgctgaaaaa agtggtgctc aacgagattg gcaagtgccc     240

ggatatttgg agctcgcgga gccaggcagc cattatggag cactatccga ttgttgcaac     300

tgaaacgtac aggaggacag ggttgctgtt gtctatcaaa tcgctgaaac aaatctacaa     360

atgcggaaag gacaatctcc gaaaccggct tcgcgtggca attgtaagca agcggcttac     420

accggcccaa gtagaggcct atatgtggcg ctgggagttt tacggcttta ttcgctacta     480

tcgagactat acacaacgct gggaggccga cttgttgaaa gatttggacg tggtgctcgg     540

gctcgaggct cggcgagcat cgaaaaatat ggaaaaggtg gattctgggg agctcatgga     600

gcccatggag cccatggatt ctacaatgga tgagatgtgc gtcgaggagg agccctacga     660

ggagacaggg tccaattgga gcgatccggc gccggaacca tcccaatcca aatcccagtc     720

cccagaagcc aagtaccctc aagcctacct actacctgag gcggacgaag tctacaatcc     780

tgacgatttc tatcaagagg aacatgaatc cgcatcaaac gccatgtatc ggatcgcttt     840

ctcacagcag tacggtggcg gcgggtcccc agccgtgcag aagcccgtca cttttagtgc     900

tcagccggcg ccggcgccag ttagagaggc cccaagccca gttgtggaga atgttagttc     960

atcgagtttc accccgaagc cccggccat gatcaacaat tttggtgagg agatgaacca     1020

aataacatac caagcgatcc gtattgcccg agagcagccg gaacgtctga aattgctccg    1080

taaggcactt ttcgacgttg tcctggcgtt tgatcagaag gaatacgccg atgttgggga    1140

tttgtacagg gatttggcgc aaaagaattc gtgataattt ttttttgagt tttttaattt    1200

ttaatttatt tcaatttttg ttacatgttc caatataata aacaggtgct tgtttaaaaa    1260

aaaaaaaaaa aaaaaa                                                    1276
```

-continued

<210> SEQ ID NO 3
<211> LENGTH: 322
<212> TYPE: PRT
<213> ORGANISM: Caenorhabditis elegans

<400> SEQUENCE: 3

```
Met Asp His His Ala Met Tyr Arg Thr Ala Glu Phe Asn Lys Thr Thr
 1               5                  10                  15

Val Arg Leu Leu Ala Glu Phe Ile Glu Lys Thr Gly Gln Asn Ala Thr
            20                  25                  30

Ile Val Asn Met Asp Ser Phe Leu Glu Phe Phe Ala Tyr Leu Asn Pro
        35                  40                  45

Thr Ala Pro Ile Pro Thr Val Pro Glu Ile Glu Lys Gln Leu Leu Leu
    50                  55                  60

Lys Ser Pro Ile Arg Cys Ile Val Cys Gly Met Glu Thr Glu Ser Asp
65                  70                  75                  80

Ser Ala Val Thr Leu Ser Ile Asp Asn Ala Ser Ile Ile Leu Thr Ala
                85                  90                  95

Thr Val Ile Gly Tyr Cys Arg Asp Pro Ser Asp Ala Val Asn Gln Ile
            100                 105                 110

Arg Lys Glu Ser Leu Arg Ala Cys Thr Lys His Phe Asn Ser Ile Phe
        115                 120                 125

His Val Ile Phe Glu Gly Leu Gln Ile Glu Asn Thr Tyr Cys Ala His
    130                 135                 140

His Ala Lys Tyr Ser Leu Ala Asn Arg Trp Cys Lys Val Tyr Thr Met
145                 150                 155                 160

Ile Arg Ser Ser Leu Gly Glu Gln Phe Thr Lys Phe Asp Val Arg Asn
                165                 170                 175

Phe Lys Ser Ile Leu Gln Ser Phe Leu Asp Thr Phe Gly Glu Ile Asp
            180                 185                 190

Asp Asp Lys Lys Asp Lys Glu Ser Ser His Phe Asp Glu Cys Phe Glu
        195                 200                 205

Glu Met Asp Ser Glu Asn Val Glu Ile Lys Met Glu Ser Pro Gln Glu
    210                 215                 220

Glu Ala Ala Glu Lys Ser Lys Phe Ser Glu Asn Leu Val Glu Val Lys
225                 230                 235                 240

Leu Glu Pro Ile Glu Thr His Glu Leu Asp Lys Thr Ile Ser Asp Phe
                245                 250                 255

Ser Ser Ser Asp Ile Ile Asp Ser Ser Gln Lys Leu Gln Gln Asn Gly
            260                 265                 270

Phe Pro Glu Lys Val Glu Gln Met Asp Lys Tyr Ser Asn Lys Leu Lys
        275                 280                 285

Asp Glu Ala Ser Asp Lys Lys Tyr Glu Lys Pro Gly Lys Lys Asp Tyr
    290                 295                 300

Val Glu Glu Glu Gly Tyr Trp Ala Pro Ile Thr Asp Ser Glu Asp Asp
305                 310                 315                 320

Glu Ala
```

<210> SEQ ID NO 4
<211> LENGTH: 1108
<212> TYPE: DNA
<213> ORGANISM: Caenorhabditis elegans -continued

<400> SEQUENCE: 4

```
gcaaaaaact agatattttg tggcattttt acaattaaaa aacctttaaa aaatggatca     60
ccatgctatg taccgaaccg ctgaattcaa caaaactact gtccgattat tggcggaatt    120
catcgaaaag actgggcaga atgcgacgat agtgaatatg gacagctttt tggagttctt    180
tgcgtatttg aatcccacgg ctccaattcc aacggttcca gaaattgaaa aacaattatt    240
gctaaaatca ccgattcgtt gcattgtgtg tggaatggaa actgaatcag attccgcagt    300
gacattaagc atcgataatg cttcaattat tctcacagcg acagtaattg gttactgtag    360
agatccaagt gatgcagtta atcaaattcg aaaggagagt cttcgagcat gcacgaaaca    420
tttcaacagt attttccatg tcatcttcga aggactgcaa atcgagaaca cctactgtgc    480
tcatcatgca aaatacagtc ttgccaatcg ttggtgcaaa gtctacacga tgattcgatc    540
ttccctgggc gagcagttca caaagttcga tgtgcgcaat tttaaatcaa tattgcaatc    600
atttttggat actttttggtg aaattgatga cgacaaaaag gataaagaat cttctcattt   660
tgatgaatgt tttgaagaaa tggattcaga aaacgtagaa attaaaatgg agagcccaca    720
agaagaagct gcagagaaat cgaagttttc tgaaaaccta gtggaggtaa aactggaacc    780
aattgaaact catgaacttg acaaaactat atccgacttt tcttcaagtg atataattga    840
ttcgtcccaa aaactgcagc aaaatggttt tcctgaaaaa gtggagcaaa tggacaaata    900
tagcaacaaa ttgaaagatg aagcttcaga caaaaagtat gaaaagccag gaaaaaagga    960
ctacgttgaa gaagagggat actgggcgcc gatcaccgac agcgaggatg atgaagcctg   1020
aatttattta atcaaacgtt ttggaaattt tttttgtttt tgtcaataaa accatataac   1080
aataaaaaaa aaaaaaaaaa aactcgag                                      1108
```

<210> SEQ ID NO 5
<211> LENGTH: 498
<212> TYPE: PRT
<213> ORGANISM: Caenorhabditis elegans

<400> SEQUENCE: 5

```
Met Ser Glu Phe Leu Lys Ile Val Arg Ala Asn Lys Lys Ser Asp Arg
1               5                   10                  15

Lys Leu Asp Lys Thr Tyr Leu Trp Glu Ser Tyr Leu His Gln Phe Glu
            20                  25                  30

Lys Gly Lys Thr Ser Phe Ile Pro Val Glu Ala Phe Asn Arg Asn Leu
        35                  40                  45

Thr Val Asn Phe Asn Glu Cys Val Lys Glu Gly Val Ile Phe Glu Thr
    50                  55                  60

Val Val His Asp Tyr Asp Lys Asn Cys Asp Ser Ile Gln Val Arg Trp
65                  70                  75                  80

Phe Ala Arg Ile Glu Lys Val Cys Gly Tyr Arg Val Leu Ala Gln Phe
                85                  90                  95

Ile Gly Ala Asp Thr Lys Phe Trp Leu Asn Ile Leu Ser Asp Asp Met
            100                 105                 110

Phe Gly Leu Ala Asn Ala Ala Met Ser Asp Pro Asn Met Asp Lys Ile
        115                 120                 125

Val Tyr Ala Pro Pro Leu Ala Ile Asn Glu Glu Tyr Gln Asn Asp Met
    130                 135                 140

Val Asn Tyr Val Asn Asn Cys Ile Asp Gly Glu Ile Val Gly Gln Thr
145                 150                 155                 160
```

-continued

```
Ser Leu Ser Pro Lys Phe Asp Glu Gly Lys Ala Leu Leu Ser Lys His
                165                 170                 175

Arg Phe Lys Val Gly Gln Arg Leu Glu Leu Leu Asn Tyr Ser Asn Ser
            180                 185                 190

Thr Glu Ile Arg Val Ala Arg Ile Gln Glu Ile Cys Gly Arg Arg Met
        195                 200                 205

Asn Val Ser Ile Thr Lys Lys Asp Phe Pro Glu Ser Leu Pro Asp Ala
    210                 215                 220

Asp Asp Asp Arg Gln Val Phe Ser Ser Gly Ser Gln Tyr Trp Ile Asp
225                 230                 235                 240

Glu Gly Ser Phe Phe Ile Phe Pro Val Gly Phe Ala Ala Val Asn Gly
                245                 250                 255

Tyr Gln Leu Asn Ala Lys Lys Glu Tyr Ile Glu His Thr Asn Lys Ile
            260                 265                 270

Ala Gln Ala Ile Lys Asn Gly Glu Asn Pro Arg Tyr Asp Ser Asp Asp
        275                 280                 285

Val Thr Phe Asp Gln Leu Ala Lys Asp Pro Ile Asp Pro Met Ile Trp
    290                 295                 300

Arg Lys Val Lys Val Gly Gln Lys Phe Glu Leu Ile Asp Pro Leu Ala
305                 310                 315                 320

Gln Gln Phe Asn Asn Leu His Val Ala Ser Ile Leu Lys Phe Cys Lys
                325                 330                 335

Thr Glu Gly Tyr Leu Ile Val Gly Met Asp Gly Pro Asp Ala Leu Glu
            340                 345                 350

Asp Ser Phe Pro Ile His Ile Asn Asn Thr Phe Met Phe Pro Val Gly
        355                 360                 365

Tyr Ala Glu Lys Tyr Asn Leu Glu Leu Val Pro Pro Asp Glu Phe Lys
    370                 375                 380

Gly Thr Phe Arg Trp Asp Glu Tyr Leu Glu Lys Glu Ser Ala Glu Thr
385                 390                 395                 400

Leu Pro Leu Asp Leu Phe Lys Pro Met Pro Ser Gln Glu Arg Leu Asp
                405                 410                 415

Lys Phe Lys Val Ile Leu Ile Ser Lys Arg Val Gly Leu Arg Leu Glu
            420                 425                 430

Ala Ala Asp Met Cys Glu Asn Gln Phe Ile Cys Pro Ala Thr Val Lys
        435                 440                 445

Ser Val His Gly Arg Leu Ile Asn Val Asn Phe Asp Gly Trp Asp Glu
    450                 455                 460

Glu Phe Asp Glu Leu Tyr Asp Val Asp Ser His Asp Ile Leu Pro Ile
465                 470                 475                 480

Gly Trp Cys Glu Ala His Ser Tyr Val Leu Gln Pro Pro Lys Lys Tyr
                485                 490                 495

Asn Tyr
```

<210> SEQ ID NO 6
<211> LENGTH: 1497
<212> TYPE: DNA
<213> ORGANISM: Caenorhabditis elegans

<400> SEQUENCE: 6

```
atgtctgaat ttctgaaaat tgtcagagct aacaaaaaat cggacagaaa actcgataag     60

acctacttgt gggaatccta tttacatcag ttcgagaaag gaaaaacttc tttcattcca    120

gttgaagcat tcaatcgtaa ccttacagtt aattttaacg aatgcgtgaa ggaaggagtt    180
```

-continued

```
atcttcgaaa cagtggtcca tgattatgac aagaactgcg attcgattca agtcagatgg    240

tttgcacgaa ttgaaaaagt ttgcggatac agagttctgg ctcagtttat cggagctgac    300

acgaaatttt ggctcaatat tttatcggac gatatgtttg gtttggcaaa cgccgcaatg    360

agtgatccca atatggataa aattgtatat gctccgccgc ttgcaatcaa cgaagaatac    420

caaaatgata tggtaaatta tgtaaataat tgcattgatg gcgaaatcgt cggccaaact    480

tcgctgtctc caaaattcga tgaagggaag gctctcctaa gcaagcatcg tttcaaagtt    540

ggacaacgtc ttgaactatt aaattattcc aattctactg aaatacgcgt agcgcgaatt    600

caagaaatat gtggacgacg aatgaatgta tctatcacaa agaaagactt tcccgaatcg    660

cttccagatg cagatgacga cagacaagtc tttagctctg gatctcaata ttggatagac    720

gagggaagct tcttcatatt tcctgttgga tttgcagcag tcaatggata tcaactaaat    780

gcgaaaaagg aatatattga gcacacaaat aaaattgctc aagcaataaa aaatggagaa    840

aatccaagat atgactcaga cgacgtcaca tttgatcaat tagcaaaaga tccaattgat    900

cccatgattt ggagaaaagt taaggttgga caaaagtttg agctcatcga ccccttggct    960

cagcaattca ataacctcca cgtcgcttcg attctcaaat tttgcaaaac tgaaggatat   1020

cttattgtgg gaatggatgg tccagatgca cttgaagaca gttttcctat tcatatcaat   1080

aatacattta tgttcccagt tggttatgcg gaaaagtata atttggaact tgttccgcca   1140

gatgagttca aggaacatt cagatgggat gaatacttgg agaaagaatc tgcagaaacc    1200

ctaccgcttg acttgttcaa gccaatgcct tcccaagaga gattagacaa atttaaggta   1260

attctgattt ccaaacgggt aggactacgc cttgaagctg ctgacatgtg tgaaaatcag   1320

tttatttgtc cagctacagt gaaatcagtt catggaagac tgataaatgt caatttcgac   1380

ggctgggatg aagaatttga tgaactgtat gatgtggact cccatgatat tctaccgata   1440

ggatggtgtg aagcgcacag ttatgttcta caacctccga aaaagtacaa ctattga      1497
```

<210> SEQ ID NO 7
<211> LENGTH: 100
<212> TYPE: PRT
<213> ORGANISM: Artificial Sequence
<220> FEATURE:
<223> OTHER INFORMATION: derived from Caenorhabditis elegans, Drosophila melanogaster, Mus musculus and Homo sapiens

<400> SEQUENCE: 7

```
Phe Asp Trp Glu Asp Tyr Leu Glu Glu Thr Gly Ala Arg Ala Ala Pro
 1               5                  10                  15

Val Glu Leu Phe Asp Lys Gln Pro Val Asp Ser Pro Pro Asn Gly Phe
            20                  25                  30

Lys Val Gly Met Lys Leu Glu Ala Val Asp Pro Arg Asn Pro Ser Leu
        35                  40                  45

Ile Cys Val Ala Thr Val Val Glu Val Lys Gly Tyr Arg Leu Leu Leu
    50                  55                  60

His Phe Asp Gly Trp Asp Asp Arg Tyr Asp Phe Trp Cys Asp Ala Asp
65                  70                  75                  80

Ser Pro Asp Ile Phe Pro Val Gly Trp Cys Glu Lys Asn Gly His Pro
                85                  90                  95

Leu Gln Pro Pro
            100
```

-continued

```
<210> SEQ ID NO 8
<211> LENGTH: 100
<212> TYPE: PRT
<213> ORGANISM: Drosophila melanogaster

<400> SEQUENCE: 8

Trp Ser Trp Glu Ser Tyr Leu Glu Glu Gln Lys Ala Ile Thr Ala Pro
 1               5                  10                  15

Val Ser Leu Phe Asp Ser Gln Ala Val Thr His Asn Lys Asn Gly Phe
            20                  25                  30

Lys Leu Gly Met Lys Leu Glu Gly Ile Asp Pro Gln His Pro Ser Met
        35                  40                  45

Tyr Phe Ile Leu Thr Val Ala Glu Val Cys Gly Tyr Arg Leu Arg Leu
    50                  55                  60

His Phe Asp Gly Tyr Ser Glu Cys His Asp Phe Trp Val Asn Ala Asn
65                  70                  75                  80

Ser Pro Asp Ile His Pro Ala Gly Trp Phe Glu Lys Thr Gly His Lys
                85                  90                  95

Leu Gln Leu Pro
            100


<210> SEQ ID NO 9
<211> LENGTH: 100
<212> TYPE: PRT
<213> ORGANISM: Drosophila melanogaster

<400> SEQUENCE: 9

Phe Ser Trp Ser Gln Tyr Met Cys Ser Thr Arg Ala Gln Ala Ala Pro
 1               5                  10                  15

Lys His Met Phe Val Ser Gln Ser His Ser Pro Pro Pro Leu Gly Phe
            20                  25                  30

Gln Val Gly Met Lys Leu Glu Ala Val Asp Arg Met Asn Pro Ser Leu
        35                  40                  45

Val Cys Val Ala Ser Val Thr Asp Val Val Asp Ser Arg Phe Leu Val
    50                  55                  60

His Phe Asp Asn Trp Asp Asp Thr Tyr Asp Tyr Trp Cys Asp Pro Ser
65                  70                  75                  80

Ser Pro Tyr Ile His Pro Val Gly Trp Cys Gln Lys Gln Gly Lys Pro
                85                  90                  95

Leu Thr Pro Pro
            100


<210> SEQ ID NO 10
<211> LENGTH: 96
<212> TYPE: PRT
<213> ORGANISM: Drosophila melanogaster

<400> SEQUENCE: 10

Phe Cys Trp Glu Lys Tyr Leu Glu Glu Thr Gly Ala Ser Ala Val Pro
 1               5                  10                  15

Thr Trp Ala Phe Lys Val Arg Pro Pro His Ser Phe Leu Val Asn Met
            20                  25                  30

Lys Leu Glu Ala Val Asp Arg Arg Asn Pro Ala Leu Ile Arg Val Ala
        35                  40                  45

Ser Val Glu Asp Val Glu Asp His Arg Ile Lys Ile His Phe Asp Gly
    50                  55                  60
```

-continued

Trp Ser His Gly Tyr Asp Phe Trp Ile Asp Ala Asp His Pro Asp Ile
65 70 75 80

His Pro Ala Gly Trp Cys Ser Lys Thr Gly His Pro Leu Gln Pro Pro
85 90 95

<210> SEQ ID NO 11
<211> LENGTH: 99
<212> TYPE: PRT
<213> ORGANISM: Drosophila melanogaster

<400> SEQUENCE: 11

Phe Arg Trp Ser Glu Tyr Leu Ser Lys Gly Lys Asp Val Ala Ala Pro
1 5 10 15

Ile His Leu Phe Leu Asn Pro Phe Pro Ile Ser Pro Asn Cys Phe Glu
20 25 30

Ile Gly Met Lys Leu Glu Ala Ile Asp Pro Glu Asn Cys Ser Leu Phe
35 40 45

Cys Val Cys Ser Ile Val Glu Val Arg Gly Tyr Arg Leu Lys Leu Ser
50 55 60

Phe Asp Gly Tyr Ser Ser Met Tyr Asp Phe Trp Val Asn Ala Asp Ser
65 70 75 80

Gln Asp Ile Phe Pro Pro Gly Trp Cys Asp Glu Thr Ala Arg Val Leu
85 90 95

Gln Ala Pro

<210> SEQ ID NO 12
<211> LENGTH: 100
<212> TYPE: PRT
<213> ORGANISM: Drosophila melanogaster

<400> SEQUENCE: 12

Phe Ser Trp Ser Arg Tyr Leu Val Lys Thr Gly Gly Lys Ala Ala Pro
1 5 10 15

Arg Ala Leu Phe Asn Met Gln Gln Gln Met Asp Val Arg Asn Gly Phe
20 25 30

Ala Val Gly Met His Leu Glu Ala Glu Asp Leu Asn Asp Thr Gly Lys
35 40 45

Ile Cys Val Ala Thr Val Thr Asp Ile Leu Asp Glu Arg Ile Arg Val
50 55 60

His Phe Asp Gly Trp Asp Asp Cys Tyr Asp Leu Trp Val His Ile Thr
65 70 75 80

Ser Pro Tyr Ile His Pro Cys Gly Trp His Glu Gly Arg Gln Gln Leu
85 90 95

Ile Val Pro Pro
100

<210> SEQ ID NO 13
<211> LENGTH: 96
<212> TYPE: PRT
<213> ORGANISM: Drosophila melanogaster

<400> SEQUENCE: 13

Phe Ile Trp Asp Asp Tyr Ile Ser Glu Val Gly Gly Met Ala Ala Ser
1 5 10 15

Lys Glu Leu Phe Thr Pro Arg Gln Pro Met Glu Tyr Gln Glu Arg Met
20 25 30

Lys Leu Glu Val Val Asp Gln Arg Asn Pro Cys Leu Ile Arg Pro Ala
35 40 45

-continued

```
Thr Val Val Thr Arg Lys Gly Tyr Arg Val Gln Leu His Leu Asp Cys
    50                  55                  60

Trp Pro Thr Glu Tyr Tyr Phe Trp Leu Glu Asp Asp Ser Pro Asp Leu
65                  70                  75                  80

His Pro Ile Gly Trp Cys Glu Ala Thr Ser His Glu Leu Glu Thr Pro
                85                  90                  95


<210> SEQ ID NO 14
<211> LENGTH: 99
<212> TYPE: PRT
<213> ORGANISM: Mus musculus

<400> SEQUENCE: 14

Phe Thr Trp Asp Lys Tyr Leu Lys Glu Thr Cys Ser Val Pro Ala Pro
 1               5                  10                  15

Val His Cys Phe Lys Gln Ser Tyr Thr Pro Pro Ser Asn Glu Phe Lys
            20                  25                  30

Ile Ser Met Lys Leu Glu Ala Gln Asp Pro Arg Asn Thr Thr Ser Thr
        35                  40                  45

Cys Ile Ala Thr Val Val Gly Leu Thr Gly Ala Arg Leu Arg Leu Arg
    50                  55                  60

Leu Asp Gly Ser Asp Asn Lys Asn Asp Phe Trp Arg Leu Val Asp Ser
65                  70                  75                  80

Ser Glu Ile Gln Pro Ile Gly Asn Cys Glu Lys Asn Gly Gly Met Leu
                85                  90                  95

Gln Pro Pro


<210> SEQ ID NO 15
<211> LENGTH: 100
<212> TYPE: PRT
<213> ORGANISM: Homo sapiens

<400> SEQUENCE: 15

Ser Ser Trp Pro Met Phe Leu Thr Leu Asn Gly Ser Glu Met Ala Ser
 1               5                  10                  15

Ala Thr Leu Phe Lys Lys Glu Pro Pro Lys Pro Pro Leu Asn Asn Phe
            20                  25                  30

Lys Val Gly Met Lys Leu Glu Ala Ile Asp Lys Lys Asn Pro Tyr Leu
        35                  40                  45

Ile Cys Pro Ala Thr Ile Gly Asp Val Lys Gly Asp Glu Val His Ile
    50                  55                  60

Thr Phe Asp Gly Trp Ser Gly Ala Phe Asp Tyr Trp Cys Lys Tyr Asp
65                  70                  75                  80

Ser Arg Asp Ile Phe Pro Ala Gly Trp Cys Arg Leu Thr Gly Asp Val
                85                  90                  95

Leu Gln Pro Pro
            100


<210> SEQ ID NO 16
<211> LENGTH: 1276
<212> TYPE: DNA
<213> ORGANISM: Caenorhabditis elegans

<400> SEQUENCE: 16

agaatctgcc aaaatgtcaa agataaagac acattccact ggctcaaaac ggacggtacc      60

attctacaag ccgccaccgc ccgtgccact tccaccactc ccgccacccg atccaacccg     120

gtacttctcg acggaaaagt acatcgcact gagcaaagat gagaaattca aatttgatga     180
```

-continued

```
ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc cccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaattttttg ttacatgttc caatataata aacaggtgct tgtttaaaaa   1260

aaaaaaaaaa aaaaaa                                                  1276
```

<210> SEQ ID NO 17
<211> LENGTH: 386
<212> TYPE: PRT
<213> ORGANISM: Caenorhabditis elegans

<400> SEQUENCE: 17

```
Met Ser Lys Ile Lys Thr His Ser Thr Gly Ser Lys Arg Thr Val Pro
 1               5                  10                  15

Phe Tyr Lys Pro Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175
```

-continued

```
Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385


<210> SEQ ID NO 18
<211> LENGTH: 1276
<212> TYPE: DNA
<213> ORGANISM: Caenorhabditis elegans

<400> SEQUENCE: 18

agaatctgcc aaaatgtcaa agataaagac acattccact ggctcaaaac ggacggtacc      60

attctacaag ctgccaccgc ccgtgccact tccaccactc ccgccacccg atccaacccg     120

gtacttctcg acggaaaagt acatcgcact gagcaaagat gagaaattca aatttgatga     180

ttacgatgtg aatgatgaga cgctgaaaaa agtgatgctc aacgagattg gcaagtgccc     240

ggatatttgg agctcgcgga gccaggcagc cattatggag cactatccga ttgttgcaac     300

tgaaacgtac aggaggacag ggttgctgtt gtctatcaaa tcgctgaaac aaatctacaa     360

atgcggaaag gacaatctcc gaaaccggct tcgcgtggca attgtaagca agcggcttac     420

accggcccaa gtagaggcct atatgtggcg ctgggagttt tacggcttta ttcgctacta     480

tcgagactat acacaacgct gggaggccga cttgttgaaa gatttggacg tggtgctcgg     540

gctcgaggct cggcgagcat cgaaaaatat ggaaaaggtg gattctgggg agctcatgga     600

gcccatggag cccatggatt ctacaatgga tgagatgtgc gtcgaggagg agccctacga     660

ggagacaggg tccaattgga gcgatccggc gccggaacca tcccaatcca aatcccagtc     720

cccagaagcc aagtaccctc aagcctacct actacctgag gcggacgaag tctacaatcc     780

tgacgatttc tatcaagagg aacatgaatc cgcatcaaac gccatgtatc ggatcgcttt     840

ctcacagcag tacggtggcg gcgggtcccc agccgtgcag aagcccgtca cttttagtgc     900
```

-continued

```
tcagccggcg ccggcgccag ttagagaggc cccaagccca gttgtggaga atgttagttc    960

atcgagtttc accccgaagc cccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt tttttgagt tttttaattt   1200

ttaatttatt tcaatttttg ttacatgttc caatataata aacaggtgct tgtttaaaaa   1260

aaaaaaaaaa aaaaaa                                                   1276
```

<210> SEQ ID NO 19
<211> LENGTH: 386
<212> TYPE: PRT
<213> ORGANISM: Caenorhabditis elegans

<400> SEQUENCE: 19

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Met Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300
```

-continued

```
Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385
```

<210> SEQ ID NO 20
<211> LENGTH: 1276
<212> TYPE: DNA
<213> ORGANISM: Caenorhabditis elegans

<400> SEQUENCE: 20

```
agaatctgcc aaaatgtcaa agataaagac acattccact ggctcaaaac ggacggtacc      60

attctacaag ctgccaccgc ccgtgccact tccaccactc ccgccacccg atccaacccg     120

gtacttctcg acggaaaagt acatcgcact gagcaaagat gagaaattca aatttgatga     180

ttacgatgtg aatgatgaga cgctgaaaaa agtggtgctc aacgagattg gcaagtgccc     240

ggatatttag agctcgcgga gccaggcagc cattatggag cactatccga ttgttgcaac     300

tgaaacgtac aggaggacag ggttgctgtt gtctatcaaa tcgctgaaac aaatctacaa     360

atgcggaaag gacaatctcc gaaaccggct tcgcgtggca attgtaagca agcggcttac     420

accggcccaa gtagaggcct atatgtggcg ctgggagttt tacggcttta ttcgctacta     480

tcgagactat acacaacgct gggaggccga cttgttgaaa gatttggacg tggtgctcgg     540

gctcgaggct cggcgagcat cgaaaaatat ggaaaaggtg gattctgggg agctcatgga     600

gcccatggag cccatggatt ctacaatgga tgagatgtgc gtcgaggagg agccctacga     660

ggagacaggg tccaattgga gcgatccggc gccggaacca tcccaatcca aatcccagtc     720

cccagaagcc aagtaccctc aagcctacct actacctgag gcggacgaag tctacaatcc     780

tgacgatttc tatcaagagg aacatgaatc cgcatcaaac gccatgtatc ggatcgcttt     840

ctcacagcag tacggtggcg gcgggtcccc agccgtgcag aagcccgtca cttttagtgc     900

tcagccggcg ccggcgccag ttagagaggc cccaagccca gttgtggaga atgttagttc     960

atcgagtttc accccgaagc cccggccat gatcaacaat tttggtgagg agatgaacca    1020

aataacatac caagcgatcc gtattgcccg agagcagccg gaacgtctga aattgctccg    1080

taaggcactt ttcgacgttg tcctggcgtt tgatcagaag gaatacgccg atgttgggga    1140

tttgtacagg gatttggcgc aaaagaattc gtgataattt ttttttgagt tttttaattt    1200

ttaatttatt tcaatttttg ttacatgttc caatataata aacaggtgct tgtttaaaaa    1260

aaaaaaaaaa aaaaaa                                                   1276
```

<210> SEQ ID NO 21
<211> LENGTH: 78
<212> TYPE: PRT
<213> ORGANISM: Caenorhabditis elegans -continued

<400> SEQUENCE: 21

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile
65                  70                  75
```

<210> SEQ ID NO 22
<211> LENGTH: 1276
<212> TYPE: DNA
<213> ORGANISM: Caenorhabditis elegans

<400> SEQUENCE: 22

```
agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaat aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc ccccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                   1276
```

<210> SEQ ID NO 23
<211> LENGTH: 112
<212> TYPE: PRT
<213> ORGANISM: Caenorhabditis elegans -continued

<400> SEQUENCE: 23

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110
```

<210> SEQ ID NO 24
<211> LENGTH: 1276
<212> TYPE: DNA
<213> ORGANISM: Caenorhabditis elegans

<400> SEQUENCE: 24

```
agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcacgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc cccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                  1276
```

-continued

```
<210> SEQ ID NO 25
<211> LENGTH: 386
<212> TYPE: PRT
<213> ORGANISM: Caenorhabditis elegans

<400> SEQUENCE: 25

Met Ser Lys Ile Lys Thr His Ser Thr Gly Ser Lys Arg Thr Val Pro
 1               5                   10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu His Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365
```

-continued

```
Lys Glu Tyr Ala Asp Val Gly Asp Leu Tyr Arg Asp Leu Ala Gln Lys
    370                 375                 380

Asn Ser
385


<210> SEQ ID NO 26
<211> LENGTH: 1276
<212> TYPE: DNA
<213> ORGANISM: Caenorhabditis elegans

<400> SEQUENCE: 26

agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggca ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc ccccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                   1276


<210> SEQ ID NO 27
<211> LENGTH: 386
<212> TYPE: PRT
<213> ORGANISM: Caenorhabditis elegans

<400> SEQUENCE: 27

Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60
```

-continued

```
Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp His Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385
```

<210> SEQ ID NO 28
<211> LENGTH: 1276
<212> TYPE: DNA
<213> ORGANISM: Caenorhabditis elegans

<400> SEQUENCE: 28

```
agaatctgcc aaaatgtcaa agataaagac acattccact ggctcaaaac ggacggtacc      60

attctacaag ctgccaccgc ccgtgccact tccaccactc ccgccacccg atccaacccg     120

gtacttctcg acggaaaagt acatcgcact gagcaaagat gagaaattca aatttgatga     180

ttacgatgtg aatgatgaga cgctgaaaaa agtggtgctc aacgagattg gcaagtgccc     240
```

-continued

```
ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgagagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc cccggccat gatcaacaat tttggtgagg agatgaacca    1020

aataacatac caagcgatcc gtattgcccg agagcagccg gaacgtctga aattgctccg    1080

taaggcactt ttcgacgttg tcctggcgtt tgatcagaag gaatacgccg atgttgggga    1140

tttgtacagg gatttggcgc aaaagaattc gtgataattt ttttttgagt tttttaattt    1200

ttaatttatt tcaatttttg ttacatgttc caatataata aacaggtgct tgtttaaaaa    1260

aaaaaaaaaa aaaaaa                                                   1276
```

<210> SEQ ID NO 29
<211> LENGTH: 146
<212> TYPE: PRT
<213> ORGANISM: Caenorhabditis elegans

<400> SEQUENCE: 29

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg
145
```

<210> SEQ ID NO 30
<211> LENGTH: 1276
<212> TYPE: DNA
<213> ORGANISM: Caenorhabditis elegans -continued

<400> SEQUENCE: 30

```
agaatctgcc aaaatgtcaa agataaagac acattccact ggctcaaaac ggacggtacc     60
attctacaag ctgccaccgc ccgtgccact tccaccactc ccgccacccg atccaacccg    120
gtacttctcg acggaaaagt acatcgcact gagcaaagat gagaaattca aatttgatga    180
ttacgatgtg aatgatgaga cgctgaaaaa agtggtgctc aacgagattg gcaagtgccc    240
ggatatttgg agctcgcgga gccaggcagc cattatggag cactatccga ttgttgcaac    300
tgaaacgtac aggaggacag ggttgctgtt gtctatcaaa tcgctgaaac aaatctacaa    360
atgcggaaag gacaatctcc gaaaccggct tcgcgtggca attgtaagca agcggcttac    420
accggcccaa gtagaggcct atatgtggcg ctggaagttt tacggcttta ttcgctacta    480
tcgagactat acacaacgct gggaggccga cttgttgaaa gatttggacg tggtgctcgg    540
gctcgaggct cggcgagcat cgaaaaatat ggaaaaggtg gattctgggg agctcatgga    600
gcccatggag cccatggatt ctacaatgga tgagatgtgc gtcgaggagg agccctacga    660
ggagacaggg tccaattgga gcgatccggc gccggaacca tcccaatcca aatcccagtc    720
cccagaagcc aagtaccctc aagcctacct actacctgag gcggacgaag tctacaatcc    780
tgacgatttc tatcaagagg aacatgaatc cgcatcaaac gccatgtatc ggatcgcttt    840
ctcacagcag tacggtggcg gcgggtcccc agccgtgcag aagcccgtca cttttagtgc    900
tcagccggcg ccggcgccag ttagagaggc cccaagccca gttgtggaga atgttagttc    960
atcgagtttc accccgaagc cccggccat gatcaacaat tttggtgagg agatgaacca    1020
aataacatac caagcgatcc gtattgcccg agagcagccg gaacgtctga aattgctccg   1080
taaggcactt ttcgacgttg tcctggcgtt tgatcagaag gaatacgccg atgttgggga   1140
tttgtacagg gatttggcgc aaaagaattc gtgataattt ttttttgagt tttttaattt   1200
ttaatttatt tcaatttttg ttacatgttc caatataata aacaggtgct tgtttaaaaa   1260
aaaaaaaaaa aaaaaa                                                   1276
```

<210> SEQ ID NO 31
<211> LENGTH: 386
<212> TYPE: PRT
<213> ORGANISM: Caenorhabditis elegans

<400> SEQUENCE: 31

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125
```

-continued

```
Ala Ile Val Ser Lys Arg Leu Thr Pro Ala Gln Val Glu Ala Tyr Met
    130                 135                 140

Trp Arg Trp Lys Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385
```

<210> SEQ ID NO 32
<211> LENGTH: 1276
<212> TYPE: DNA
<213> ORGANISM: Caenorhabditis elegans

<400> SEQUENCE: 32

```
agaatctgcc aaaatgtcaa agataaagac acattccact ggctcaaaac ggacggtacc      60

attctacaag ctgccaccgc ccgtgccact tccaccactc ccgccacccg atccaacccg     120

gtacttctcg acggaaaagt acatcgcact gagcaaagat gagaaattca aatttgatga     180

ttacgatgtg aatgatgaga cgctgaaaaa agtggtgctc aacgagattg gcaagtgccc     240

ggatatttgg agctcgcgga gccaggcagc cattatggag cactatccga ttgttgcaac     300

tgaaacgtac aggaggacag ggttgctgtt gtctatcaaa tcgctgaaac aaatctacaa     360

atgcggaaag gacaatctcc gaaaccggct tcgcgtggca attgtaagca agcggcttac     420

accggcccaa gtagaggcct atatgtggcg ctgggagttt tacggcttta tttgctacta     480

tcgagactat acacaacgct gggaggccga cttgttgaaa gatttggacg tggtgctcgg     540

gctcgaggct cggcgagcat cgaaaaatat ggaaaaggtg gattctgggg agctcatgga     600
```

-continued

```
gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc cccggccat gatcaacaat tttggtgagg agatgaacca    1020

aataacatac caagcgatcc gtattgcccg agagcagccg gaacgtctga aattgctccg    1080

taaggcactt ttcgacgttg tcctggcgtt tgatcagaag gaatacgccg atgttgggga    1140

tttgtacagg gatttggcgc aaaagaattc gtgataattt ttttttgagt tttttaattt    1200

ttaatttatt tcaatttttg ttacatgttc caatataata aacaggtgct tgtttaaaaa    1260

aaaaaaaaaa aaaaaa                                                  1276
```

<210> SEQ ID NO 33
<211> LENGTH: 386
<212> TYPE: PRT
<213> ORGANISM: Caenorhabditis elegans

<400> SEQUENCE: 33

```
Met Ser Lys Ile Lys Thr His Ser Thr Gly Ser Lys Arg Thr Val Pro
1               5                   10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Cys Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255
```

-continued

```
Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385


<210> SEQ ID NO 34
<211> LENGTH: 1276
<212> TYPE: DNA
<213> ORGANISM: Caenorhabditis elegans

<400> SEQUENCE: 34

agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct aggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc cccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                    1276
```

-continued

<210> SEQ ID NO 35
<211> LENGTH: 162
<212> TYPE: PRT
<213> ORGANISM: Caenorhabditis elegans

<400> SEQUENCE: 35

```
Met Ser Lys Ile Lys Thr His Ser Thr Gly Ser Lys Arg Thr Val Pro
 1              5                   10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg
```

<210> SEQ ID NO 36
<211> LENGTH: 1276
<212> TYPE: DNA
<213> ORGANISM: Caenorhabditis elegans

<400> SEQUENCE: 36

```
agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct ggaaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960
```

-continued

```
atcgagtttc accccgaagc ccccggccat gatcaacaat tttggtgagg agatgaacca   1020

aataacatac caagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                   1276


<210> SEQ ID NO 37
<211> LENGTH: 386
<212> TYPE: PRT
<213> ORGANISM: Caenorhabditis elegans

<400> SEQUENCE: 37

Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Lys Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320
```

-continued

```
Pro Lys Pro Pro Ala Met Ile Asn Asn Phe Gly Glu Glu Met Asn Gln
                325                 330                 335

Ile Thr Tyr Gln Ala Ile Arg Ile Ala Arg Glu Gln Pro Glu Arg Leu
            340                 345                 350

Lys Leu Leu Arg Lys Ala Leu Phe Asp Val Val Leu Ala Phe Asp Gln
        355                 360                 365

Lys Glu Tyr Ala Asp Val Gly Asp Leu Tyr Arg Asp Leu Ala Gln Lys
    370                 375                 380

Asn Ser
385
```

<210> SEQ ID NO 38
<211> LENGTH: 1275
<212> TYPE: DNA
<213> ORGANISM: Caenorhabditis elegans

<400> SEQUENCE: 38

```
agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaagtgg attctgggga gctcatggag    600

cccatggagc ccatggattc tacaatggat gagatgtgcg tcgaggagga gccctacgag    660

gagacagggt ccaattggag cgatccggcg ccggaaccat cccaatccaa atcccagtcc    720

ccagaagcca agtaccctca agcctaccta ctacctgagg cggacgaagt ctacaatcct    780

gacgatttct atcaagagga acatgaatcc gcatcaaacg ccatgtatcg gatcgctttc    840

tcacagcagt acggtggcgg cgggtcccca gccgtgcaga agcccgtcac ttttagtgct    900

cagccggcgc cggcgccagt tagagaggcc ccaagcccag ttgtggagaa tgttagttca    960

tcgagtttca ccccgaagcc cccggccatg atcaacaatt ttggtgagga gatgaaccaa   1020

ataacatacc aagcgatccg tattgcccga gagcagccgg aacgtctgaa attgctccgt   1080

aaggcacttt tcgacgttgt cctggcgttt gatcagaagg aatacgccga tgttggggat   1140

ttgtacaggg atttggcgca aaagaattcg tgataatttt tttttgagtt ttttaatttt   1200

taatttattt caatttttgt tacatgttcc aatataataa acaggtgctt gtttaaaaaa   1260

aaaaaaaaaa aaaaa                                                     1275
```

<210> SEQ ID NO 39
<211> LENGTH: 325
<212> TYPE: PRT
<213> ORGANISM: Caenorhabditis elegans -continued

<400> SEQUENCE: 39

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Trp Ile Leu Gly
            180                 185                 190

Ser Ser Trp Ser Pro Trp Ser Pro Trp Ile Leu Gln Trp Met Arg Cys
        195                 200                 205

Ala Ser Arg Arg Ser Pro Thr Arg Arg Gln Gly Pro Ile Gly Ala Ile
    210                 215                 220

Arg Arg Arg Asn His Pro Asn Pro Asn Pro Ser Pro Gln Lys Pro Ser
225                 230                 235                 240

Thr Leu Lys Pro Thr Tyr Tyr Leu Arg Arg Thr Lys Ser Thr Ile Leu
                245                 250                 255

Thr Ile Ser Ile Lys Arg Asn Met Asn Pro His Gln Thr Pro Cys Ile
            260                 265                 270

Gly Ser Leu Ser His Ser Ser Thr Val Ala Ala Gly Pro Gln Pro Cys
        275                 280                 285

Arg Ser Pro Ser Leu Leu Val Leu Ser Arg Arg Arg Arg Gln Leu Glu
    290                 295                 300

Arg Pro Gln Ala Gln Leu Trp Arg Met Leu Val His Arg Val Ser Pro
305                 310                 315                 320

Arg Ser Pro Arg Pro
                325
```

<210> SEQ ID NO 40
<211> LENGTH: 1276
<212> TYPE: DNA
<213> ORGANISM: Caenorhabditis elegans

<400> SEQUENCE: 40

```
agaatctgcc aaaatgtcaa agataaagac acattccact ggctcaaaac ggacggtacc      60

attctacaag ctgccaccgc ccgtgccact tccaccactc ccgccacccg atccaacccg     120

gtacttctcg acggaaaagt acatcgcact gagcaaagat gagaaattca aatttgatga     180
```

-continued

```
ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagtag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc cccggccat gatcaacaat tttggtgagg agatgaacca    1020

aataacatac caagcgatcc gtattgcccg agagcagccg gaacgtctga aattgctccg    1080

taaggcactt ttcgacgttg tcctggcgtt tgatcagaag gaatacgccg atgttgggga    1140

tttgtacagg gatttggcgc aaaagaattc gtgataattt ttttttgagt tttttaattt    1200

ttaatttatt tcaattttg ttacatgttc caatataata aacaggtgct tgtttaaaaa    1260

aaaaaaaaaa aaaaaa                                                    1276
```

<210> SEQ ID NO 41
<211> LENGTH: 278
<212> TYPE: PRT
<213> ORGANISM: Caenorhabditis elegans

<400> SEQUENCE: 41

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175
```

-continued

```
Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln
        275
```

<210> SEQ ID NO 42
<211> LENGTH: 1276
<212> TYPE: DNA
<213> ORGANISM: Caenorhabditis elegans

<400> SEQUENCE: 42

```
agaatctgcc aaaatgtcaa agataaagac acattccact ggctcaaaac ggacggtacc     60
attctacaag ctgccaccgc ccgtgccact tccaccactc ccgccacccg atccaacccg    120
gtacttctcg acggaaaagt acatcgcact gagcaaagat gagaaattca aatttgatga    180
ttacgatgtg aatgatgaga cgctgaaaaa agtggtgctc aacgagattg gcaagtgccc    240
ggatatttgg agctcgcgga gccaggcagc cattatggag cactatccga ttgttgcaac    300
tgaaacgtac aggaggacag ggttgctgtt gtctatcaaa tcgctgaaac aaatctacaa    360
atgcggaaag gacaatctcc gaaaccggct tcgcgtggca attgtaagca agcggcttac    420
accggcccaa gtagaggcct atatgtggcg ctgggagttt tacggcttta ttcgctacta    480
tcgagactat acacaacgct gggaggccga cttgttgaaa gatttggacg tggtgctcgg    540
gctcgaggct cggcgagcat cgaaaaatat ggaaaaggtg gattctgggg agctcatgga    600
gcccatggag cccatggatt ctacaatgga tgagatgtgc gtcgaggagg agccctacga    660
ggagacaggg tccaattgga gcgatccggc gccggaacca tcccaatcca aatcccagtc    720
cccagaagcc aagtaccctc aagcctacct actacctgag gcggacgaag tctacaatcc    780
tgacgatttc tatcaagagg aacatgaatc cgcatcaaac gccatgtatc ggatcgcttt    840
ctcacagcag tacggtggcg gcgggtcccc agccgtgcag aagcccgtca cttttagtgc    900
tcagccggcg ccggcgccag tttgagaggc cccaagccca gttgtggaga atgttagttc    960
atcgagtttc accccgaagc cccggccat gatcaacaat tttggtgagg agatgaacca   1020
aataacatac caagcgatcc gtattgcccg agagcagccg gaacgtctga aattgctccg   1080
taaggcactt ttcgacgttg tcctggcgtt tgatcagaag gaatacgccg atgttgggga   1140
tttgtacagg gatttggcgc aaaagaattc gtgataattt ttttttgagt tttttaattt   1200
ttaatttatt tcaatttttg ttacatgttc caatataata aacaggtgct tgtttaaaaa   1260
aaaaaaaaaa aaaaaa                                                  1276
```

<210> SEQ ID NO 43
<211> LENGTH: 303
<212> TYPE: PRT
<213> ORGANISM: Caenorhabditis elegans -continued

<400> SEQUENCE: 43

Met Ser Lys Ile Lys Thr His Ser Thr Gly Ser Lys Arg Thr Val Pro
1 5 10 15

Phe Tyr Lys Leu Pro Pro Pro Val Pro Leu Pro Pro Leu Pro Pro Pro
20 25 30

Asp Pro Thr Arg Tyr Phe Ser Thr Glu Lys Tyr Ile Ala Leu Ser Lys
35 40 45

Asp Glu Lys Phe Lys Phe Asp Asp Tyr Asp Val Asn Asp Glu Thr Leu
50 55 60

Lys Lys Val Val Leu Asn Glu Ile Gly Lys Cys Pro Asp Ile Trp Ser
65 70 75 80

Ser Arg Ser Gln Ala Ala Ile Met Glu His Tyr Pro Ile Val Ala Thr
85 90 95

Glu Thr Tyr Arg Arg Thr Gly Leu Leu Leu Ser Ile Lys Ser Leu Lys
100 105 110

Gln Ile Tyr Lys Cys Gly Lys Asp Asn Leu Arg Asn Arg Leu Arg Val
115 120 125

Ala Ile Val Ser Lys Arg Leu Thr Pro Ala Gln Val Glu Ala Tyr Met
130 135 140

Trp Arg Trp Glu Phe Tyr Gly Phe Ile Arg Tyr Tyr Arg Asp Tyr Thr
145 150 155 160

Gln Arg Trp Glu Ala Asp Leu Leu Lys Asp Leu Asp Val Val Leu Gly
165 170 175

Leu Glu Ala Arg Arg Ala Ser Lys Asn Met Glu Lys Val Asp Ser Gly
180 185 190

Glu Leu Met Glu Pro Met Glu Pro Met Asp Ser Thr Met Asp Glu Met
195 200 205

Cys Val Glu Glu Glu Pro Tyr Glu Glu Thr Gly Ser Asn Trp Ser Asp
210 215 220

Pro Ala Pro Glu Pro Ser Gln Ser Lys Ser Gln Ser Pro Glu Ala Lys
225 230 235 240

Tyr Pro Gln Ala Tyr Leu Leu Pro Glu Ala Asp Glu Val Tyr Asn Pro
245 250 255

Asp Asp Phe Tyr Gln Glu Glu His Glu Ser Ala Ser Asn Ala Met Tyr
260 265 270

Arg Ile Ala Phe Ser Gln Gln Tyr Gly Gly Gly Gly Ser Pro Ala Val
275 280 285

Gln Lys Pro Val Thr Phe Ser Ala Gln Pro Ala Pro Ala Pro Val
290 295 300

<210> SEQ ID NO 44
<211> LENGTH: 1276
<212> TYPE: DNA
<213> ORGANISM: Caenorhabditis elegans

<400> SEQUENCE: 44
agaatctgcc aaaatgtcaa agataaagac acattccact ggctcaaaac ggacggtacc 60
attctacaag ctgccaccgc ccgtgccact tccaccactc ccgccacccg atccaacccg 120
gtacttctcg acggaaaagt acatcgcact gagcaaagat gagaaattca aatttgatga 180
ttacgatgtg aatgatgaga cgctgaaaaa agtggtgctc aacgagattg gcaagtgccc 240
ggatatttgg agctcgcgga gccaggcagc cattatggag cactatccga ttgttgcaac 300
tgaaacgtac aggaggacag ggttgctgtt gtctatcaaa tcgctgaaac aaatctacaa 360

-continued

```
atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc ccccggccat gatcaacaat tttggtgagg agatgaacca   1020

aataacatac taagcgatcc gtattgcccg agagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                    1276
```

```
<210> SEQ ID NO 45
<211> LENGTH: 339
<212> TYPE: PRT
<213> ORGANISM: Caenorhabditis elegans

<400> SEQUENCE: 45

Met Ser Lys Ile Lys Thr His Ser Thr Gly Ser Lys Arg Thr Val Pro
1               5                   10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205
```

-continued

```
Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr


<210> SEQ ID NO 46
<211> LENGTH: 1276
<212> TYPE: DNA
<213> ORGANISM: Caenorhabditis elegans

<400> SEQUENCE: 46

agaatctgcc aaaatgtcaa agataaagac acattccact ggctcaaaac ggacggtacc     60

attctacaag ctgccaccgc ccgtgccact tccaccactc ccgccacccg atccaacccg    120

gtacttctcg acggaaaagt acatcgcact gagcaaagat gagaaattca aatttgatga    180

ttacgatgtg aatgatgaga cgctgaaaaa agtggtgctc aacgagattg gcaagtgccc    240

ggatatttgg agctcgcgga gccaggcagc cattatggag cactatccga ttgttgcaac    300

tgaaacgtac aggaggacag ggttgctgtt gtctatcaaa tcgctgaaac aaatctacaa    360

atgcggaaag gacaatctcc gaaaccggct tcgcgtggca attgtaagca agcggcttac    420

accggcccaa gtagaggcct atatgtggcg ctgggagttt tacggcttta ttcgctacta    480

tcgagactat acacaacgct gggaggccga cttgttgaaa gatttggacg tggtgctcgg    540

gctcgaggct cggcgagcat cgaaaaatat ggaaaaggtg gattctgggg agctcatgga    600

gcccatggag cccatggatt ctacaatgga tgagatgtgc gtcgaggagg agccctacga    660

ggagacaggg tccaattgga gcgatccggc gccggaacca tcccaatcca aatcccagtc    720

cccagaagcc aagtaccctc aagcctacct actacctgag gcggacgaag tctacaatcc    780

tgacgatttc tatcaagagg aacatgaatc cgcatcaaac gccatgtatc ggatcgcttt    840

ctcacagcag tacggtggcg gcgggtcccc agccgtgcag aagcccgtca cttttagtgc    900

tcagccggcg ccggcgccag ttagagaggc cccaagccca gttgtggaga atgttagttc    960

atcgagtttc accccgaagc ccccggccat gatcaacaat tttggtgagg agatgaacca   1020

aataacatac caagcgatcc gtattgcccg aaagcagccg gaacgtctga aattgctccg   1080

taaggcactt ttcgacgttg tcctggcgtt tgatcagaag gaatacgccg atgttgggga   1140

tttgtacagg gatttggcgc aaaagaattc gtgataattt ttttttgagt tttttaattt   1200

ttaatttatt tcaatttttg ttacatgttc caatataata aacaggtgct tgtttaaaaa   1260

aaaaaaaaaa aaaaaa                                                   1276
```

-continued

<210> SEQ ID NO 47
<211> LENGTH: 386
<212> TYPE: PRT
<213> ORGANISM: Caenorhabditis elegans

<400> SEQUENCE: 47

```
Met Ser Lys Ile Lys Thr His Ser Thr Gly Ser Lys Arg Thr Val Pro
 1               5                  10                  15

Phe Tyr Lys Leu Pro Pro Pro Val Pro Leu Pro Pro Leu Pro Pro Pro
            20                  25                  30

Asp Pro Thr Arg Tyr Phe Ser Thr Glu Lys Tyr Ile Ala Leu Ser Lys
        35                  40                  45

Asp Glu Lys Phe Lys Phe Asp Asp Tyr Asp Val Asn Asp Glu Thr Leu
    50                  55                  60

Lys Lys Val Val Leu Asn Glu Ile Gly Lys Cys Pro Asp Ile Trp Ser
65                  70                  75                  80

Ser Arg Ser Gln Ala Ala Ile Met Glu His Tyr Pro Ile Val Ala Thr
                85                  90                  95

Glu Thr Tyr Arg Arg Thr Gly Leu Leu Leu Ser Ile Lys Ser Leu Lys
            100                 105                 110

Gln Ile Tyr Lys Cys Gly Lys Asp Asn Leu Arg Asn Arg Leu Arg Val
        115                 120                 125

Ala Ile Val Ser Lys Arg Leu Thr Pro Ala Gln Val Glu Ala Tyr Met
    130                 135                 140

Trp Arg Trp Glu Phe Tyr Gly Phe Ile Arg Tyr Tyr Arg Asp Tyr Thr
145                 150                 155                 160

Gln Arg Trp Glu Ala Asp Leu Leu Lys Asp Leu Asp Val Val Leu Gly
                165                 170                 175

Leu Glu Ala Arg Arg Ala Ser Lys Asn Met Glu Lys Val Asp Ser Gly
            180                 185                 190

Glu Leu Met Glu Pro Met Glu Pro Met Asp Ser Thr Met Asp Glu Met
        195                 200                 205

Cys Val Glu Glu Glu Pro Tyr Glu Glu Thr Gly Ser Asn Trp Ser Asp
    210                 215                 220

Pro Ala Pro Glu Pro Ser Gln Ser Lys Ser Gln Ser Pro Glu Ala Lys
225                 230                 235                 240

Tyr Pro Gln Ala Tyr Leu Leu Pro Glu Ala Asp Glu Val Tyr Asn Pro
                245                 250                 255

Asp Asp Phe Tyr Gln Glu Glu His Glu Ser Ala Ser Asn Ala Met Tyr
            260                 265                 270

Arg Ile Ala Phe Ser Gln Gln Tyr Gly Gly Gly Gly Ser Pro Ala Val
        275                 280                 285

Gln Lys Pro Val Thr Phe Ser Ala Gln Pro Ala Pro Ala Pro Val Arg
    290                 295                 300

Glu Ala Pro Ser Pro Val Val Glu Asn Val Ser Ser Ser Ser Phe Thr
305                 310                 315                 320

Pro Lys Pro Pro Ala Met Ile Asn Asn Phe Gly Glu Glu Met Asn Gln
                325                 330                 335

Ile Thr Tyr Gln Ala Ile Arg Ile Ala Arg Lys Gln Pro Glu Arg Leu
            340                 345                 350

Lys Leu Leu Arg Lys Ala Leu Phe Asp Val Val Leu Ala Phe Asp Gln
        355                 360                 365
```

-continued

Lys Glu Tyr Ala Asp Val Gly Asp Leu Tyr Arg Asp Leu Ala Gln Lys
370 375 380

Asn Ser
385

<210> SEQ ID NO 48
<211> LENGTH: 1108
<212> TYPE: DNA
<213> ORGANISM: Caenorhabditis elegans

<400> SEQUENCE: 48
gcaaaaaact agatattttg tggcattttt acaattaaaa aacctttaaa aaatggatca 60
ccatgctatg taccgaaccg ctgaattcaa caaaactact gtccgattat tggcggaatt 120
catcgaaaag actgggcaga atgcgacgat agtgaatatg gacagctttt tggagttctt 180
tgcgtatttg aatcccacgg ctccaattcc aacggttcca gaaattgaaa aataattatt 240
gctaaaatca ccgattcgtt gcattgtgtg tggaatggaa actgaatcag attccgcagt 300
gacattaagc atcgataatg cttcaattat tctcacagcg acagtaattg gttactgtag 360
agatccaagt gatgcagtta atcaaattcg aaaggagagt cttcgagcat gcacgaaaca 420
tttcaacagt attttccatg tcatcttcga aggactgcaa atcgagaaca cctactgtgc 480
tcatcatgca aaatacagtc ttgccaatcg ttggtgcaaa gtctacacga tgattcgatc 540
ttccctgggc gagcagttca caaagttcga tgtgcgcaat tttaaatcaa tattgcaatc 600
atttttggat acttttggtg aaattgatga cgacaaaaag gataaagaat cttctcattt 660
tgatgaatgt tttgaagaaa tggattcaga aaacgtagaa attaaaatgg agagcccaca 720
agaagaagct gcagagaaat cgaagttttc tgaaaaccta gtggaggtaa aactggaacc 780
aattgaaact catgaacttg acaaaactat atccgacttt tcttcaagtg atataattga 840
ttcgtcccaa aaactgcagc aaaatggttt tcctgaaaaa gtggagcaaa tggacaaata 900
tagcaacaaa ttgaaagatg aagcttcaga caaaaagtat gaaaagccag gaaaaaagga 960
ctacgttgaa gaagagggat actgggcgcc gatcaccgac agcgaggatg atgaagcctg 1020
aatttattta atcaaacgtt ttggaaattt tttttgtttt tgtcaataaa accatataac 1080
aataaaaaaa aaaaaaaaaa aactcgag 1108

<210> SEQ ID NO 49
<211> LENGTH: 60
<212> TYPE: PRT
<213> ORGANISM: Caenorhabditis elegans

<400> SEQUENCE: 49

Met Asp His His Ala Met Tyr Arg Thr Ala Glu Phe Asn Lys Thr Thr
1 5 10 15

Val Arg Leu Leu Ala Glu Phe Ile Glu Lys Thr Gly Gln Asn Ala Thr
20 25 30

Ile Val Asn Met Asp Ser Phe Leu Glu Phe Phe Ala Tyr Leu Asn Pro
35 40 45

Thr Ala Pro Ile Pro Thr Val Pro Glu Ile Glu Lys
50 55 60

<210> SEQ ID NO 50

<400> SEQUENCE: 50

000

-continued

<210> SEQ ID NO 51
<211> LENGTH: 60
<212> TYPE: PRT
<213> ORGANISM: Caenorhabditis elegans

<400> SEQUENCE: 51

```
Arg Cys Ile Val Cys Gly Met Glu Thr Glu Ser Asp Ser Ala Val Thr
 1               5                  10                  15

Leu Ser Ile Asp Asn Ala Ser Ile Ile Leu Thr Ala Thr Val Ile Gly
            20                  25                  30

Tyr Cys Arg Asp Pro Ser Asp Ala Val Asn Gln Ile Arg Lys Glu Ser
        35                  40                  45

Leu Arg Ala Cys Thr Lys His Phe Asn Ser Ile Phe
    50                  55                  60
```

<210> SEQ ID NO 52
<211> LENGTH: 60
<212> TYPE: PRT
<213> ORGANISM: Caenorhabditis elegans

<400> SEQUENCE: 52

```
Pro Cys Ile Leu Cys Glu Lys Ala Leu Leu Met Arg Glu Ser Ile Ala
 1               5                  10                  15

Met Thr Asp Asn Glu Ala Val Lys Val Leu Met Ala Ala Val Met Ser
            20                  25                  30

Gly His Phe Arg Met Ala Thr Ala Glu Lys Ala Ile Arg His Glu Arg
        35                  40                  45

Leu Arg Met Cys Tyr Asp His Val Asp Phe Val Tyr
    50                  55                  60
```

<210> SEQ ID NO 53
<211> LENGTH: 60
<212> TYPE: PRT
<213> ORGANISM: Caenorhabditis elegans

<400> SEQUENCE: 53

```
Pro Cys Ile Ile Cys Gly Asn Glu Val Pro Gly His Arg Ser Ile Arg
 1               5                  10                  15

Val Ser Asp Asp Asp Ala Ala Ile Phe Leu Thr Ala Ala Val Leu Thr
            20                  25                  30

Asp Gln Lys Thr Ile Arg Gln Ala Lys Arg Asp Ile Leu Ser Glu Tyr
        35                  40                  45

Leu Thr Val Cys Leu Arg His Ser Leu His Tyr Tyr
    50                  55                  60
```

<210> SEQ ID NO 54
<211> LENGTH: 60
<212> TYPE: PRT
<213> ORGANISM: Caenorhabditis elegans

<400> SEQUENCE: 54

```
Pro Cys Leu Val Cys Asn Gln Gln Met Glu Met Thr Lys Val Arg Ser
 1               5                  10                  15

Val Asn Asn Thr Asp Ala Tyr Ile Met Ile Tyr Val Cys Val Met Asn
            20                  25                  30

Asp Lys Tyr Asp Met Asp Lys Ala Lys Glu Leu Ala Arg Met Gln Arg
        35                  40                  45

Phe Lys Cys Cys Val Ser His Leu Asp Glu Leu Tyr
    50                  55                  60
```

-continued

<210> SEQ ID NO 55
<211> LENGTH: 177
<212> TYPE: PRT
<213> ORGANISM: Caenorhabditis elegans

<400> SEQUENCE: 55

```
Met Leu Ser Ile Lys Gln Glu Leu Leu Asp Ala Pro Pro Pro Pro Pro
 1               5                  10                  15

Ala Ala Thr Pro Leu Pro Pro Ile Thr His Arg Ile Ser Leu Ser Gly
            20                  25                  30

Tyr Arg Asn Ile His Ala Lys Ser Phe Leu Lys Thr Met Thr Met Asp
        35                  40                  45

Leu Cys Val Arg Arg Val Val Leu Ser Leu Leu Glu Asn Arg Arg Ala
    50                  55                  60

Leu Trp Ile Arg Val His Lys Ser Pro Lys Ala Asp Trp Glu Val Leu
65                  70                  75                  80

Gly Val Glu Val Phe Glu Arg Thr Gly Lys Ala Val Ser Val Lys Gln
                85                  90                  95

Leu Gln Arg Ile Phe Leu Thr Ala Arg Asp Trp Leu Arg Arg Asn Leu
            100                 105                 110

Gln Leu Tyr Ile Ile Gln Arg Lys Met Asp Lys Leu Thr Leu Asp Ala
        115                 120                 125

Glu Leu Ala Lys Trp Glu Leu Tyr Pro His Phe Ile Tyr Tyr Arg Gln
    130                 135                 140

Tyr Leu Gly Gln Phe Glu Ala His Leu Arg Gly Glu Glu Trp Thr Gly
145                 150                 155                 160

Glu Leu Tyr Asp Asp Asp Ile Ile Cys Asp Gly Ile Met Gln Val Glu
                165                 170                 175

Val
```

<210> SEQ ID NO 56
<211> LENGTH: 75
<212> TYPE: PRT
<213> ORGANISM: Caenorhabditis elegans

<400> SEQUENCE: 56

```
Glu Asp Ser Val Ser Tyr Thr Lys Ile Thr Glu Asp Leu Leu Gln Lys
 1               5                  10                  15

Lys Pro His Lys His Arg Phe Ile Arg Gln Ala Leu Phe Lys Thr Ile
            20                  25                  30

Met Ala Leu Asp Asp Asp Glu Val Glu Tyr Thr Glu Leu Ala Asp Leu
        35                  40                  45

Phe Gly Asp Ile Ala Glu Gln Ser Asn Val Val Arg Arg Leu Arg Leu
    50                  55                  60

Gln Arg Gln Gln Gln Arg Gly Arg Gly Glu Gln
65                  70                  75
```

<210> SEQ ID NO 57
<211> LENGTH: 178
<212> TYPE: PRT
<213> ORGANISM: Caenorhabditis elegans

<400> SEQUENCE: 57

```
Met Ser Leu Ile Lys Gln Glu His Met His Pro Pro Pro Arg Ala Ile
 1               5                  10                  15

Thr Pro Leu Pro Pro Ala Thr His Gln Ile Thr Leu Glu Glu Tyr Lys
            20                  25                  30
```

-continued

```
Glu Arg Glu Lys Lys Asp Tyr Tyr Arg Asp Ala Thr Lys Asp Ala Ser
        35                  40                  45

Val Lys Lys Val Val Leu Ser Leu Leu Lys Asp His Pro Gly Met Trp
    50                  55                  60

Gln Asn Gly Asn Arg Phe Gln Pro Glu Lys Trp Arg Ala Leu Gly Val
65                  70                  75                  80

Asp Val Tyr Gln Arg Thr Gly Gln Ile Val Arg Val Asn Asp Met Arg
                85                  90                  95

Lys Met Leu Val Met Gly Lys Ser Val Leu Lys Lys Lys Ile Ala Ile
            100                 105                 110

Cys Ile Arg Asp Lys Lys Leu Asp Arg Ala Ala Thr Glu Lys Asp Leu
        115                 120                 125

Trp Tyr Trp Glu Tyr Tyr Arg His Phe Leu Tyr Tyr Arg Glu Thr Leu
    130                 135                 140

Gly Gln Phe Glu Ala Asn Leu Arg Gly Glu Glu Trp Thr Gly Glu Asp
145                 150                 155                 160

Gln Ile Gln Asp Glu Asp Asp Ile Ile Tyr Asp Gly Met Leu Asp Gly
                165                 170                 175

Asp Leu


<210> SEQ ID NO 58
<211> LENGTH: 73
<212> TYPE: PRT
<213> ORGANISM: Caenorhabditis elegans

<400> SEQUENCE: 58

Arg Ser Ala Gln His Ile Ala Glu Gln Ala Lys Arg Leu Phe Leu Gln
 1               5                  10                  15

Tyr Pro Glu Lys Ser Asn Leu Ile Arg Glu Thr Met Phe Lys Thr Ile
            20                  25                  30

Leu Ala Phe Asp Asp Pro Ser Ala Asp Tyr Gln Asn Val Gly Glu Ile
        35                  40                  45

Phe Asp Asp Leu Ala Ala Gln Glu Ala Ala Lys Lys Arg Lys Arg Ala
    50                  55                  60

Glu Asn Arg Ala Gln Arg Glu Gln Gln
65                  70


<210> SEQ ID NO 59
<211> LENGTH: 179
<212> TYPE: PRT
<213> ORGANISM: Caenorhabditis elegans

<400> SEQUENCE: 59

Met Ser Leu Ile Lys Gln Glu His Met Asn Pro Pro Pro Arg Thr Ile
 1               5                  10                  15

Thr Pro Leu Pro Pro Pro Thr His Gln Ile Thr Ile Glu Glu Tyr Lys
            20                  25                  30

Glu Arg Val Lys Arg Asp Tyr Tyr Arg Asn Ala Thr Lys Asp Thr Ser
        35                  40                  45

Leu Lys Lys Val Val Leu Ser Leu Ile Lys Asp Arg Lys Ala Met Trp
    50                  55                  60

Ala Pro Ala Ala Lys Pro Ser Glu Asp Lys Trp Gln Lys Leu Gly Ala
65                  70                  75                  80

Glu Val Phe Ser Arg Thr Gly Lys Val Val Ser Val Thr Gln Leu Arg
                85                  90                  95
```

-continued

```
Arg Met Leu Val Ser Ser Lys His Val Leu Lys Thr Lys Met Ser His
            100                 105                 110

Cys Ile Lys Val Lys Lys Met Asp Arg Val Ser Thr Glu Ala Tyr Leu
        115                 120                 125

Trp Asn Trp Glu Phe Tyr Arg His Phe Leu Tyr Tyr Arg Glu Met Leu
    130                 135                 140

Asp Arg Phe Glu Ala Asn Leu Arg Gly Lys Gln Trp Thr Gly Glu Asp
145                 150                 155                 160

Gln Pro Thr Asp Asp Asp Asp Asp Ile Ile Cys Asp Gly Ile Phe Glu
                165                 170                 175

Val Glu Met
```

<210> SEQ ID NO 60
<211> LENGTH: 70
<212> TYPE: PRT
<213> ORGANISM: Caenorhabditis elegans

<400> SEQUENCE: 60

```
Ser Thr Ala Glu Gln Ile Gly Glu Glu Ile Asp Arg Leu Ile Gln Leu
 1               5                  10                  15

Tyr Pro Gln Arg Glu Met Leu Ile Arg Gln Ala Phe Phe Lys Thr Ile
            20                  25                  30

Phe Ala Leu Glu Asp Glu Thr Val Glu Phe Ser Asn Leu Gly Asp Leu
        35                  40                  45

Phe Glu Asp Leu Ala Glu Gln Glu Asn Phe Lys Arg Arg Arg Arg Ser
    50                  55                  60

Arg Ala Gln Arg Leu Glu
65                  70
```

<210> SEQ ID NO 61
<211> LENGTH: 187
<212> TYPE: PRT
<213> ORGANISM: Caenorhabditis elegans

<400> SEQUENCE: 61

```
Met Leu Asn Ile Lys Gln Glu Gly Val Val Ala Asp Ala Pro Arg Ala
 1               5                  10                  15

Leu Thr Pro Ile Pro Pro Phe Ile His His Val Ser Met Glu Glu Tyr
            20                  25                  30

Met Gly Met Glu Leu Asn Ser Val Tyr Glu Glu Ala Thr Lys Asp Ser
        35                  40                  45

Ala Leu Lys Lys Val Val Leu Asp Leu Leu Lys Asp Arg Pro Gly Met
    50                  55                  60

Trp Gln Asn Gly Asn Arg Phe Gln Leu Glu Asn Trp Arg Glu Leu Gly
65                  70                  75                  80

Val Asp Val Tyr Gln Arg Thr Gly Gln Ile Val Arg Ala Glu Leu Gly
                85                  90                  95

Glu Val Ser Val Asn Asp Met His Arg Met Phe Val Val Gly Lys Ala
            100                 105                 110

Val Leu Lys Gln Lys Ile Thr Val Cys Ile Arg Tyr Lys Lys Leu Asp
        115                 120                 125

Arg Ala Ala Thr Glu Ala Asp Leu Gln Asn Trp Glu Phe Tyr Arg His
    130                 135                 140

Phe Arg Tyr Tyr Arg Glu Thr Leu Gly Gln Phe Glu Ala Asn Leu Arg
145                 150                 155                 160
```

-continued

```
Gly Glu Gln Trp Thr Gly Glu Asp Gln Pro Ala Asp Asp Asp Asp Asp
                165                 170                 175

Ile Ile Tyr Asp Gly Ile Phe Glu Val Glu Met
            180                 185


<210> SEQ ID NO 62
<211> LENGTH: 69
<212> TYPE: PRT
<213> ORGANISM: Caenorhabditis elegans

<400> SEQUENCE: 62

Ser Thr Ala Glu Gln Ile Gly Glu Glu Ile Asp Arg Leu Ile Gln Leu
 1               5                  10                  15

Tyr Pro Gln Arg Glu Met Leu Ile Arg Gln Ala Phe Phe Lys Thr Ile
            20                  25                  30

Phe Ala Leu Glu Asp Glu Thr Val Glu Phe Ser Asn Leu Gly Asp Leu
        35                  40                  45

Phe Glu Asp Leu Ala Glu Gln Glu Asn Phe Lys Arg Arg Arg Arg Ser
    50                  55                  60

Ala Gln Arg Leu Glu
65


<210> SEQ ID NO 63
<211> LENGTH: 186
<212> TYPE: PRT
<213> ORGANISM: Caenorhabditis elegans

<400> SEQUENCE: 63

Met Met Asn Pro Lys Glu Glu Pro Arg Pro Phe Ser Ile Val Pro Leu
 1               5                  10                  15

Pro Arg Pro Pro Arg Pro Thr Thr Pro Leu Pro Pro Ile Ser His Cys
            20                  25                  30

Ile Thr Met Ala Asp Tyr Leu Leu Leu Glu Asn Thr Lys Phe His Lys
        35                  40                  45

Thr Ala Thr Arg Ala Pro Lys Ile Lys Lys Val Leu Leu Ser Leu Leu
    50                  55                  60

Lys Asp Arg Pro Glu Ile Trp Asp Arg Lys Ala Gln Phe Ser Ala Lys
65                  70                  75                  80

Asn Trp Gln Asn Leu Gly Val Glu Val Tyr Glu Arg Thr Gly Tyr Ile
                85                  90                  95

Val Arg Ser Asn Asp Leu His Lys Met Leu Arg Thr Ala Lys Val Val
            100                 105                 110

Leu Lys Asn Lys Leu Arg Thr Cys Ile Gly Ile Lys Lys Leu Asp Arg
        115                 120                 125

Ala Ala Thr Glu Thr Glu Leu Trp Lys Trp Glu Tyr Tyr Pro His Phe
    130                 135                 140

Ile Tyr Tyr Arg Glu Thr Leu Gly His Phe Glu Ala Asn Leu Arg Gly
145                 150                 155                 160

Glu Pro Trp Asp Gly Glu Ala His Ile Asp Asp Asp Asp Asp Asp Ile
                165                 170                 175

Ile Tyr Glu Gly Tyr Trp Glu Ala Asp Lys
            180                 185


<210> SEQ ID NO 64
<211> LENGTH: 70
<212> TYPE: PRT
<213> ORGANISM: Caenorhabditis elegans
```

-continued

<400> SEQUENCE: 64

Asn Ser Ala Gln His Ile Gly Glu Gln Val His Arg Leu Phe Ala Gln
1 5 10 15

Tyr Pro Glu Arg Ser Lys Leu Phe Arg Glu Thr Leu Phe Lys Thr Ile
20 25 30

Leu Ala Leu Glu Glu Pro Glu Tyr Glu His Ala Ala Glu Val Phe Thr
35 40 45

Asp Leu Ala Gln Ser Glu Thr Ala Lys Arg Arg Arg Arg Ser Glu Ala
50 55 60

Thr Trp Gln Asn Gly Gln
65 70

<210> SEQ ID NO 65
<211> LENGTH: 186
<212> TYPE: PRT
<213> ORGANISM: Caenorhabditis elegans

<400> SEQUENCE: 65

Met Val Ser Ala Thr Arg Val Pro Arg Arg Ser Ser Thr Thr Thr Ser
1 5 10 15

Ala Thr Ala Gln Gln Arg Thr Pro Ser Pro Leu Met Pro Ala Ser Phe
20 25 30

Pro Ile Thr Met Asp Glu Tyr Leu Glu Lys Glu Asn Arg Glu Phe Val
35 40 45

Val Asn Ala Ser Lys Asp Ile Ala Met Lys Lys Leu Ala Leu Thr Leu
50 55 60

Leu Glu Leu Tyr Pro Glu Met Trp Lys Pro Gly Gly Pro Met Val Ala
65 70 75 80

Lys Lys Trp Gln Ala Phe Gly Ala Glu Met Tyr Arg Arg Thr Gly Lys
85 90 95

Ile Tyr Arg Cys Lys Asp Leu His Ser Val Phe Thr Leu Thr Lys Ser
100 105 110

Ser Ile Lys Arg Lys Leu Arg Thr Cys Ile Leu Ile Lys Arg Met His
115 120 125

Arg Ser Lys Thr Asp Glu Glu Met Trp Lys Tyr Glu Leu Tyr Pro Tyr
130 135 140

Phe Gln Tyr Tyr Arg Gln Ser Ile Gly Gln Phe Glu Ala Lys Leu Arg
145 150 155 160

Asp Glu Pro Trp Thr Gly Glu Asp Gln Ala Gln Glu Asp Asp Asp Ile
165 170 175

Leu Phe Asp Gly Leu Phe Glu Val Glu Asn
180 185

<210> SEQ ID NO 66
<211> LENGTH: 66
<212> TYPE: PRT
<213> ORGANISM: Caenorhabditis elegans

<400> SEQUENCE: 66

Lys Thr Ala Asp Asn Ile Gly Asp Gln Val Lys Gln Leu Phe Val Asp
1 5 10 15

His Pro Asp Arg Ala Asn Phe Phe Arg Glu Val Leu Phe Lys Thr Val
20 25 30

Leu Glu Leu Arg Asp Pro Ala Phe Thr Asn Ala Gly Val Phe Phe Asp
35 40 45

-continued

```
Glu Met Ser Ser Leu Glu Ser Ala Lys Arg Arg Arg Arg Ser Glu Met
    50                  55                  60

Asn Lys
65


<210> SEQ ID NO 67
<211> LENGTH: 178
<212> TYPE: PRT
<213> ORGANISM: Caenorhabditis elegans

<400> SEQUENCE: 67

Met Ser Arg Ile Lys Gln Glu Gln Val Asn Pro Pro Pro Pro Pro Arg
 1               5                  10                  15

Ala Ile Thr Pro Leu Pro Pro Ala Thr His Arg Ile Thr Met Asp Glu
            20                  25                  30

Tyr Lys Lys Arg Glu Lys Lys Asp Tyr Tyr Arg Asp Ala Thr Lys Asp
        35                  40                  45

Ala Ser Val Lys Lys Val Val Leu Ser Leu Leu Lys Asp Tyr Pro Asp
    50                  55                  60

Met Trp Gln Asn Gly Asn Arg Phe Gln Thr Arg Lys Trp Arg Ala Leu
65                  70                  75                  80

Gly Val Glu Val Tyr Gln Arg Thr Gly Gln Ile Val Gly Val Asp Asp
                85                  90                  95

Met Arg Lys Met Phe Met Ser Gly Lys Thr Val Leu Lys Gln Lys Ile
            100                 105                 110

Thr Phe Cys Ile Arg Asn Met Lys Met Asp Arg Ala Ala Thr Glu Ala
        115                 120                 125

Asp Leu Gln Asn Trp Glu Tyr Tyr Arg His Phe Leu Tyr Tyr Arg Gln
    130                 135                 140

Thr Leu Gly Lys Phe Glu Ala Lys Leu Arg Gly Glu Gln Trp Ile Gly
145                 150                 155                 160

Glu Asp Gln Val Glu Asp Asp Asp Glu Asp Asp Val Ile Phe Asp Gly
                165                 170                 175

Glu Ser


<210> SEQ ID NO 68
<211> LENGTH: 410
<212> TYPE: PRT
<213> ORGANISM: Homo sapiens

<400> SEQUENCE: 68

Met Gly Thr Cys Trp Gly Asp Ile Ser Glu Asn Val Arg Val Glu Val
 1               5                  10                  15

Pro Asn Thr Asp Cys Ser Leu Pro Thr Lys Val Phe Trp Ile Ala Gly
            20                  25                  30

Ile Val Lys Leu Ala Gly Tyr Asn Ala Leu Leu Arg Tyr Glu Gly Phe
        35                  40                  45

Glu Asn Asp Ser Gly Leu Asp Phe Trp Cys Asn Ile Cys Gly Ser Asp
    50                  55                  60

Ile His Pro Val Gly Trp Cys Ala Ala Ser Gly Lys Pro Leu Val Pro
65                  70                  75                  80

Pro Arg Thr Ile Gln His Lys Tyr Thr Asn Trp Lys Ala Phe Leu Val
                85                  90                  95

Lys Arg Leu Thr Gly Ala Lys Thr Leu Pro Pro Asp Phe Ser Gln Lys
            100                 105                 110
```

-continued

Val Ser Glu Ser Met Gln Tyr Pro Phe Lys Pro Cys Met Arg Val Glu
115 120 125

Val Val Asp Lys Arg His Leu Cys Arg Thr Arg Val Ala Val Val Glu
130 135 140

Ser Val Ile Gly Gly Arg Leu Arg Leu Val Tyr Glu Glu Ser Glu Asp
145 150 155 160

Arg Thr Asp Asp Phe Trp Cys His Met His Ser Pro Leu Ile His His
165 170 175

Ile Gly Trp Ser Arg Ser Ile Gly His Arg Phe Lys Arg Ser Asp Ile
180 185 190

Thr Lys Lys Gln Asp Gly His Phe Thr Asp Pro Pro His Leu Phe Ala
195 200 205

Lys Val Lys Glu Val Asp Gln Ser Gly Glu Trp Phe Lys Glu Gly Met
210 215 220

Lys Leu Glu Ala Ile Asp Pro Leu Asn Leu Ser Thr Ile Cys Val Ala
225 230 235 240

Thr Ile Lys Arg Val Leu Ala Asp Gly Phe Leu Met Ile Gly Ile Asp
245 250 255

Gly Ser Glu Ala Ala Asp Gly Ser Asp Trp Phe Cys Tyr His Ala Thr
260 265 270

Ser Pro Ser Ile Phe Pro Val Gly Phe Cys Glu Ile Asn Met Ile Glu
275 280 285

Leu Thr Pro Pro Arg Gly Tyr Thr Lys Leu Pro Phe Lys Trp Phe Asp
290 295 300

Tyr Leu Arg Glu Thr Gly Ser Ile Ala Ala Pro Val Lys Leu Phe Asn
305 310 315 320

Lys Asp Val Pro Asn His Gly Phe Arg Val Gly Met Lys Leu Glu Ala
325 330 335

Val Asp Leu Met Glu Pro Arg Leu Ile Cys Val Ala Thr Val Thr Arg
340 345 350

Ile Ile His Arg Leu Leu Arg Ile His Phe Asp Gly Trp Glu Glu Glu
355 360 365

Tyr Asp Gln Trp Val Asp Cys Glu Ser Pro Asp Leu Tyr Pro Val Gly
370 375 380

Trp Cys Gln Leu Thr Gly Tyr Gln Leu Gln Pro Pro Ala Ser Gln Cys
385 390 395 400

Lys Leu Val Tyr Arg Lys Gly Val Leu Leu
405 410

<210> SEQ ID NO 69
<211> LENGTH: 512
<212> TYPE: PRT
<213> ORGANISM: Caenorhabditis elegans

<400> SEQUENCE: 69

Met Asn Phe Ser Asn Lys Lys Val Ile Leu Lys Ala Phe Leu Ser Lys
1 5 10 15

Asn Ile Ile Tyr Tyr Phe Gln Arg Gln Tyr Asn Tyr Lys Leu Glu Glu
20 25 30

Ala Glu Tyr Arg Tyr Phe Thr Glu Glu Arg Leu Phe Tyr Arg Arg Arg
35 40 45

Asn Pro Val Glu Lys Ile Ala Gln Arg Ile Pro Lys Pro Gln Ile Glu
50 55 60

Gly Thr Phe Thr Trp Ser Asp Glu Leu Arg Cys Asn Tyr Asp Gly Asn
65 70 75 80

-continued

```
Thr Gln Phe Leu Pro Val Glu Ala Leu Glu Gly Cys Leu Pro Leu Glu
                85                  90                  95

Lys Leu Asn Gln His Leu Lys Pro Gly Phe Arg Leu Glu Val Val Val
            100                 105                 110

Arg Pro Ser Leu Asp Pro Ser Ile Thr Thr Lys Ser Pro Glu Ile Arg
        115                 120                 125

Trp Phe Gly Glu Val Thr Ala Val Cys Gly Phe Tyr Val Ala Ile Lys
    130                 135                 140

Phe Val Gly Glu Leu Asn Arg Arg Pro Cys Trp Phe His Met Leu Ser
145                 150                 155                 160

Glu Asp Ile Phe Asp Ile Gly Ser Gly Leu Lys Gln Asp Pro Ala Met
                165                 170                 175

Lys Trp Leu Gln Tyr Arg Pro Leu Ser Leu Leu Lys Pro Met Gln Cys
            180                 185                 190

Pro Lys Phe Trp Arg Arg Gly Ser Thr Pro Ala Pro Pro Val Pro Arg
        195                 200                 205

Pro Thr Glu Glu Ile Leu Asp Glu Phe Gln Ala Glu Leu His Glu Asn
    210                 215                 220

Arg Ile Ser Glu Pro Lys Ile Phe Asp Gln Leu Arg His Leu Ala His
225                 230                 235                 240

Arg Pro Ser Arg Phe Arg Leu Asn Gln Arg Val Glu Leu Leu Asn Tyr
                245                 250                 255

Leu Glu Pro Thr Glu Ile Arg Val Ala Arg Ile Leu Arg Ile Leu Gly
            260                 265                 270

Arg Arg Leu Met Val Met Val Thr Ala Gln Asp Tyr Pro Glu Asp Leu
        275                 280                 285

Pro Ser Val Glu Ala Lys Asp Arg Gln Val Gln His Glu Asn Val Glu
    290                 295                 300

Phe Trp Val Asp Glu Ser Ser Phe Phe Leu Phe Pro Val Gly Phe Ala
305                 310                 315                 320

Met Ile Asn Gly Leu Arg Thr Lys Ala Thr Glu Gly Tyr Leu Glu His
                325                 330                 335

Ser Arg Arg Ile Ala Glu Gly Ser Gly Thr Glu Lys Leu Asn Leu Leu
            340                 345                 350

Lys Val Gly Gln Lys Phe Glu Leu Leu Asp Pro Leu Ser Asp Leu Arg
        355                 360                 365

Gln Ser Phe Cys Val Ala Thr Ile Arg Lys Ile Cys Lys Thr Pro Gly
    370                 375                 380

Phe Leu Ile Ile Ser Pro Asp Glu Thr Glu Ser Asp Asp Glu Ser Phe
385                 390                 395                 400

Pro Ile His Ile Asp Asn His Phe Met His Pro Val Gly Tyr Ala Glu
                405                 410                 415

Lys Phe Gly Ile Lys Leu Asp Arg Leu Ala Gly Thr Glu Pro Gly Lys
            420                 425                 430

Phe Lys Trp Glu Gly Tyr Leu Lys Glu Lys Gln Ala Glu Lys Ile Pro
        435                 440                 445

Asp Glu Met Leu Arg Pro Leu Pro Ser Lys Glu Arg Arg His Met Phe
    450                 455                 460

Glu Phe Gly Arg Val Leu Glu Ala Val Gly Gln Asn Glu Thr Tyr Trp
465                 470                 475                 480
```

-continued

```
Ile Ser Pro Ala Ser Val Glu Glu Val His Gly Arg Thr Val Leu Ile
                485                 490                 495

Glu Phe Gln Gly Trp Asp Ser Glu Phe Ser Glu Leu Tyr Asp Met Glu
            500                 505                 510
```

<210> SEQ ID NO 70
<211> LENGTH: 411
<212> TYPE: PRT
<213> ORGANISM: Caenorhabditis elegans

<400> SEQUENCE: 70

```
Met Ser Glu Phe Leu Lys Ile Val Arg Ala Asn Lys Lys Ser Asp Arg
 1               5                  10                  15

Lys Leu Asp Lys Thr Tyr Leu Trp Glu Ser Tyr Leu His Gln Phe Glu
            20                  25                  30

Lys Gly Lys Thr Ser Phe Ile Pro Val Glu Ala Phe Asn Arg Asn Leu
        35                  40                  45

Thr Val Asn Phe Asn Glu Cys Val Lys Glu Gly Val Ile Phe Glu Thr
    50                  55                  60

Val Val His Asp Tyr Asp Lys Asn Cys Asp Ser Ile Gln Val Arg Trp
65                  70                  75                  80

Phe Ala Arg Ile Glu Lys Val Cys Gly Tyr Arg Val Leu Ala Gln Phe
                85                  90                  95

Ile Gly Ala Asp Thr Lys Phe Trp Leu Asn Ile Leu Ser Asp Asp Met
            100                 105                 110

Phe Gly Leu Ala Asn Ala Ala Met Ser Asp Pro Asn Met Asp Lys Ile
        115                 120                 125

Val Tyr Ala Pro Pro Leu Ala Ile Asn Glu Glu Tyr Gln Asn Asp Met
    130                 135                 140

Val Asn Tyr Val Asn Asn Cys Ile Asp Gly Glu Ile Val Gly Gln Thr
145                 150                 155                 160

Ser Leu Ser Pro Lys Phe Asp Glu Gly Lys Ala Leu Leu Ser Lys His
                165                 170                 175

Arg Phe Lys Val Gly Gln Arg Leu Glu Leu Leu Asn Tyr Ser Asn Ser
            180                 185                 190

Thr Glu Ile Arg Val Ala Arg Ile Gln Glu Ile Cys Gly Arg Arg Met
        195                 200                 205

Asn Val Ser Ile Thr Lys Lys Asp Phe Pro Glu Ser Leu Pro Asp Ala
    210                 215                 220

Asp Asp Asp Arg Gln Val Phe Ser Ser Gly Ser Gln Tyr Trp Ile Asp
225                 230                 235                 240

Glu Gly Ser Phe Phe Ile Phe Pro Val Gly Phe Ala Ala Val Asn Gly
                245                 250                 255

Tyr Gln Leu Asn Ala Lys Lys Glu Tyr Ile Glu His Thr Asn Lys Ile
            260                 265                 270

Ala Gln Ala Ile Lys Asn Gly Glu Asn Pro Arg Tyr Asp Ser Asp Asp
        275                 280                 285

Val Thr Phe Asp Gln Leu Ala Lys Asp Pro Ile Asp Pro Met Ile Trp
    290                 295                 300

Arg Lys Val Lys Val Gly Gln Lys Phe Glu Leu Ile Asp Pro Leu Ala
305                 310                 315                 320

Gln Gln Phe Asn Asn Leu His Val Ala Ser Ile Leu Lys Phe Cys Lys
                325                 330                 335

Thr Glu Gly Tyr Leu Ile Val Gly Met Asp Gly Pro Asp Ala Leu Glu
            340                 345                 350
```

-continued

```
Asp Ser Phe Pro Ile His Ile Asn Asn Thr Phe Met Phe Pro Val Gly
        355                 360                 365

Tyr Ala Glu Lys Tyr Asn Leu Glu Leu Val Pro Pro Asp Glu Phe Lys
    370                 375                 380

Gly Thr Phe Arg Trp Asp Glu Tyr Leu Glu Lys Glu Ser Ala Glu Thr
385                 390                 395                 400

Leu Pro Leu Asp Leu Phe Lys Pro Met Pro Ser
                405                 410


<210> SEQ ID NO 71
<211> LENGTH: 498
<212> TYPE: PRT
<213> ORGANISM: Caenorhabditis elegans

<400> SEQUENCE: 71

Met Ser Glu Phe Leu Lys Ile Val Arg Ala Asn Lys Lys Ser Asp Arg
 1               5                  10                  15

Lys Leu Asp Lys Thr Tyr Leu Trp Glu Ser Tyr Leu His Gln Phe Glu
            20                  25                  30

Lys Gly Lys Thr Ser Phe Ile Pro Val Glu Ala Phe Asn Arg Asn Leu
        35                  40                  45

Thr Val Asn Phe Asn Glu Cys Val Lys Glu Gly Val Ile Phe Glu Thr
    50                  55                  60

Val Val His Asp Tyr Asp Lys Asn Cys Asp Ser Ile Gln Val Arg Trp
65                  70                  75                  80

Phe Ala Arg Ile Glu Lys Val Cys Gly Tyr Arg Val Leu Ala Gln Phe
                85                  90                  95

Ile Gly Ala Asp Thr Lys Phe Trp Leu Asn Ile Leu Ser Asp Asp Met
            100                 105                 110

Phe Gly Leu Ala Asn Ala Ala Met Ser Asp Pro Asn Met Asp Lys Ile
        115                 120                 125

Val Tyr Ala Pro Pro Leu Ala Ile Asn Glu Glu Tyr Gln Asn Asp Met
    130                 135                 140

Val Asn Tyr Val Asn Asn Cys Ile Asp Gly Glu Ile Val Gly Gln Thr
145                 150                 155                 160

Ser Leu Ser Pro Lys Phe Asp Glu Gly Lys Ala Leu Leu Ser Lys His
                165                 170                 175

Arg Phe Lys Val Gly Gln Arg Leu Glu Leu Leu Asn Tyr Ser Asn Ser
            180                 185                 190

Thr Glu Ile Arg Val Ala Arg Ile Gln Glu Ile Cys Gly Arg Arg Met
        195                 200                 205

Asn Val Ser Ile Thr Lys Lys Asp Phe Pro Glu Ser Leu Pro Asp Ala
    210                 215                 220

Asp Asp Asp Arg Gln Val Phe Ser Ser Gly Ser Gln Tyr Trp Ile Asp
225                 230                 235                 240

Glu Gly Ser Phe Phe Ile Phe Pro Val Gly Phe Ala Ala Val Asn Gly
                245                 250                 255

Tyr Gln Leu Asn Ala Lys Lys Glu Tyr Ile Glu His Thr Asn Lys Ile
            260                 265                 270

Ala Gln Ala Ile Lys Asn Gly Glu Asn Pro Arg Tyr Asp Ser Asp Asp
        275                 280                 285

Val Thr Phe Asp Gln Leu Ala Lys Asp Pro Ile Asp Pro Met Ile Trp
    290                 295                 300

Arg Lys Val Lys Val Gly Gln Lys Phe Glu Leu Ile Asp Pro Leu Ala
305                 310                 315                 320
```

-continued

Gln Gln Phe Asn Asn Leu His Val Ala Ser Ile Leu Lys Phe Cys Lys
325 330 335

Thr Glu Gly Tyr Leu Ile Val Gly Met Asp Gly Pro Asp Ala Leu Glu
340 345 350

Asp Asn Phe Pro Ile His Ile Asn Asn Thr Phe Met Phe Pro Val Gly
355 360 365

Tyr Ala Glu Lys Tyr Asn Leu Glu Leu Val Pro Pro Asp Glu Phe Lys
370 375 380

Gly Thr Phe Arg Trp Asp Glu Tyr Leu Glu Lys Glu Ser Ala Glu Thr
385 390 395 400

Leu Pro Leu Asp Leu Phe Lys Pro Met Pro Ser Gln Glu Arg Leu Asp
405 410 415

Lys Phe Lys Val Ile Leu Ile Ser Lys Arg Val Gly Leu Arg Leu Glu
420 425 430

Ala Ala Asp Met Cys Glu Asn Gln Phe Ile Cys Pro Ala Thr Val Lys
435 440 445

Ser Val His Gly Arg Leu Ile Asn Val Asn Phe Asp Gly Trp Asp Glu
450 455 460

Glu Phe Asp Glu Leu Tyr Asp Val Asp Ser His Asp Ile Leu Pro Ile
465 470 475 480

Gly Trp Cys Glu Ala His Ser Tyr Val Leu Gln Pro Pro Lys Lys Tyr
485 490 495

Asn Tyr

<210> SEQ ID NO 72
<211> LENGTH: 498
<212> TYPE: PRT
<213> ORGANISM: Caenorhabditis elegans

<400> SEQUENCE: 72

Met Ser Glu Phe Leu Lys Ile Val Arg Ala Asn Lys Lys Ser Asp Arg
1 5 10 15

Lys Leu Asp Lys Thr Tyr Leu Trp Glu Ser Tyr Leu His Gln Phe Glu
20 25 30

Lys Gly Lys Thr Ser Phe Ile Pro Val Glu Ala Phe Asn Arg Asn Leu
35 40 45

Thr Val Asn Phe Asn Glu Cys Val Lys Glu Gly Val Ile Phe Glu Thr
50 55 60

Val Val His Asp Tyr Asp Lys Asn Cys Asp Ser Ile Gln Val Arg Trp
65 70 75 80

Phe Ala Arg Ile Glu Lys Val Cys Gly Tyr Arg Val Leu Ala Gln Phe
85 90 95

Ile Gly Ala Asp Thr Lys Phe Trp Leu Asn Ile Leu Ser Asp Asp Met
100 105 110

Phe Gly Leu Ala Asn Ala Ala Met Ser Asp Pro Asn Met Asp Lys Ile
115 120 125

Val Tyr Ala Ser Pro Leu Ala Ile Asn Glu Glu Tyr Gln Asn Asp Met
130 135 140

Val Asn Tyr Val Asn Asn Cys Ile Asp Gly Glu Ile Val Gly Gln Thr
145 150 155 160

Ser Leu Ser Pro Lys Phe Asp Glu Gly Lys Ala Leu Leu Ser Lys His
165 170 175

Arg Phe Lys Val Gly Gln Arg Leu Glu Leu Leu Asn Tyr Ser Asn Ser
180 185 190

-continued

```
Thr Glu Ile Arg Val Ala Arg Ile Gln Glu Ile Cys Gly Arg Arg Met
        195                 200                 205

Asn Val Ser Ile Thr Lys Lys Asp Phe Pro Glu Ser Leu Pro Asp Ala
    210                 215                 220

Asp Asp Asp Arg Gln Val Phe Ser Ser Gly Ser Gln Tyr Trp Ile Asp
225                 230                 235                 240

Glu Gly Ser Phe Phe Ile Phe Pro Val Gly Phe Ala Ala Val Asn Gly
                245                 250                 255

Tyr Gln Leu Asn Ala Lys Lys Glu Tyr Ile Glu His Thr Asn Lys Ile
            260                 265                 270

Ala Gln Ala Ile Lys Asn Gly Glu Asn Pro Arg Tyr Asp Ser Asp Asp
        275                 280                 285

Val Thr Phe Asp Gln Leu Ala Lys Asp Pro Ile Asp Pro Met Ile Trp
    290                 295                 300

Arg Lys Val Lys Val Gly Gln Lys Phe Glu Leu Ile Asp Pro Leu Ala
305                 310                 315                 320

Gln Gln Phe Asn Asn Leu His Val Ala Ser Ile Leu Lys Phe Cys Lys
                325                 330                 335

Thr Glu Gly Tyr Leu Ile Val Gly Met Asp Gly Pro Asp Ala Leu Glu
            340                 345                 350

Asp Ser Phe Pro Ile His Ile Asn Asn Thr Phe Met Phe Pro Val Gly
        355                 360                 365

Tyr Ala Glu Lys Tyr Asn Leu Glu Leu Val Pro Pro Asp Glu Phe Lys
    370                 375                 380

Gly Thr Phe Arg Trp Asp Glu Tyr Leu Glu Lys Glu Ser Ala Glu Thr
385                 390                 395                 400

Leu Pro Leu Asp Leu Phe Lys Pro Met Pro Ser Gln Glu Arg Leu Asp
                405                 410                 415

Lys Phe Lys Val Ile Leu Ile Ser Lys Arg Val Gly Leu Arg Leu Glu
            420                 425                 430

Ala Ala Asp Met Cys Glu Asn Gln Phe Ile Cys Pro Ala Thr Val Lys
        435                 440                 445

Ser Val His Gly Arg Leu Ile Asn Val Asn Phe Asp Gly Trp Asp Glu
    450                 455                 460

Glu Phe Asp Glu Leu Tyr Asp Val Asp Ser His Asp Ile Leu Pro Ile
465                 470                 475                 480

Gly Trp Cys Glu Ala His Ser Tyr Val Leu Gln Pro Pro Lys Lys Tyr
                485                 490                 495

Asn Tyr
```

<210> SEQ ID NO 73
<211> LENGTH: 1497
<212> TYPE: DNA
<213> ORGANISM: Caenorhabditis elegans

<400> SEQUENCE: 73

```
atgtctgaat ttctgaaaat tgtcagagct aacaaaaaat cggacagaaa actcgataag      60

acctacttgt gggaatccta tttacatcag ttcgagaaag gaaaaacttc tttcattcca     120

gttgaagcat tcaatcgtaa ccttacagtt aattttaacg aatgcgtgaa ggaaggagtt     180

atcttcgaaa cagtggtcca tgattatgac aagaactgcg attcgattca agtcagatgg     240

tttgcacgaa ttgaaaaagt ttgcggatac agagttctgg ctcagtttat cggagctgac     300

acgaaatttt ggctcaatat tttatcggac gatatgtttg gtttggcaaa cgccgcaatg     360
```

-continued

```
agtgatccca atatggataa aattgtatat gctccgccgc ttgcaatcaa cgaagaatac    420
caaaatgata tggtaaatta tgtaaataat tgcattgatg gcgaaatcgt cggccaaact    480
tcgctgtctc caaaattcga tgaagggaag gctctcctaa gcaagcatcg tttcaaagtt    540
ggacaacgtc ttgaactatt aaattattcc aattctactg aaatacgcgt agcgcgaatt    600
caagaaatat gtggacgacg aatgaatgta tctatcacaa agaaagactt tcccgaatcg    660
cttccagatg cagatgacga cagacaagtc tttagctctg gatctcaata ttggatagac    720
gagggaagct tcttcatatt tcctgttgga tttgcagcag tcaatggata tcaactaaat    780
gcgaaaaagg aatatattga gcacacaaat aaaattgctc aagcaataaa aaatggagaa    840
aatccaagat atgactcaga cgacgtcaca tttgatcaat tagcaaaaga tccaattgat    900
cccatgattt ggagaaaagt taaggttgga caaaagtttg agctcatcga ccccttggct    960
cagcaattca ataacctcca cgtcgcttcg attctcaaat tttgcaaaac tgaaggatat   1020
cttattgtgg gaatggatgg tccagatgca cttgaagaca gttttcctat tcatatcaat   1080
aatacattta tgttcccagt tggttatgcg gaaaagtata atttggaact tgttccgcca   1140
gatgagttca aggaacattt cagatgggat gaatacttgg agaaagaatc tgcagaaacc   1200
ctaccgcttg acttgttcaa gccaatgcct tcctaagaga gattagacaa atttaaggta   1260
attctgattt ccaaacgggt aggactacgc cttgaagctg ctgacatgtg tgaaaatcag   1320
tttatttgtc cagctacagt gaaatcagtt catggaagac tgataaatgt caatttcgac   1380
ggctgggatg aagaatttga tgaactgtat gatgtggact cccatgatat tctaccgata   1440
ggatggtgtg aagcgcacag ttatgttcta caacctccga aaaagtacaa ctattga      1497
```

<210> SEQ ID NO 74
<211> LENGTH: 1497
<212> TYPE: DNA
<213> ORGANISM: Caenorhabditis elegans

<400> SEQUENCE: 74

```
atgtctgaat ttctgaaaat tgtcagagct aacaaaaaat cggacagaaa actcgataag     60
acctacttgt gggaatccta tttacatcag ttcgagaaag gaaaaacttc tttcattcca    120
gttgaagcat tcaatcgtaa ccttacagtt aattttaacg aatgcgtgaa ggaaggagtt    180
atcttcgaaa cagtggtcca tgattatgac aagaactgcg attcgattca agtcagatgg    240
tttgcacgaa ttgaaaaagt ttgcggatac agagttctgg ctcagtttat cggagctgac    300
acgaaatttt ggctcaatat tttatcggac gatatgtttg gtttggcaaa cgccgcaatg    360
agtgatccca atatggataa aattgtatat gctccgccgc ttgcaatcaa cgaagaatac    420
caaaatgata tggtaaatta tgtaaataat tgcattgatg gcgaaatcgt cggccaaact    480
tcgctgtctc caaaattcga tgaagggaag gctctcctaa gcaagcatcg tttcaaagtt    540
ggacaacgtc ttgaactatt aaattattcc aattctactg aaatacgcgt agcgcgaatt    600
caagaaatat gtggacgacg aatgaatgta tctatcacaa agaaagactt tcccgaatcg    660
cttccagatg cagatgacga cagacaagtc tttagctctg gatctcaata ttggatagac    720
gagggaagct tcttcatatt tcctgttgga tttgcagcag tcaatggata tcaactaaat    780
gcgaaaaagg aatatattga gcacacaaat aaaattgctc aagcaataaa aaatggagaa    840
aatccaagat atgactcaga cgacgtcaca tttgatcaat tagcaaaaga tccaattgat    900
cccatgattt ggagaaaagt taaggttgga caaaagtttg agctcatcga ccccttggct    960
cagcaattca ataacctcca cgtcgcttcg attctcaaat tttgcaaaac tgaaggatat   1020
```

-continued

```
cttattgtgg gaatggatgg tccagatgca cttgaagaca attttcctat tcatatcaat   1080

aatacattta tgttcccagt tggttatgcg gaaaagtata atttggaact tgttccgcca   1140

gatgagttca aaggaacatt cagatgggat gaatacttgg agaaagaatc tgcagaaacc   1200

ctaccgcttg acttgttcaa gccaatgcct tcccaagaga gattagacaa atttaaggta   1260

attctgattt ccaaacgggt aggactacgc cttgaagctg ctgacatgtg tgaaaatcag   1320

tttatttgtc cagctacagt gaaatcagtt catggaagac tgataaatgt caatttcgac   1380

ggctgggatg aagaatttga tgaactgtat gatgtggact cccatgatat tctaccgata   1440

ggatggtgtg aagcgcacag ttatgttcta caacctccga aaaagtacaa ctattga      1497
```

<210> SEQ ID NO 75
<211> LENGTH: 1497
<212> TYPE: DNA
<213> ORGANISM: Caenorhabditis elegans

<400> SEQUENCE: 75

```
atgtctgaat ttctgaaaat tgtcagagct aacaaaaaat cggacagaaa actcgataag     60

acctacttgt gggaatccta tttacatcag ttcgagaaag gaaaaacttc tttcattcca    120

gttgaagcat tcaatcgtaa ccttacagtt aattttaacg aatgcgtgaa ggaaggagtt    180

atcttcgaaa cagtggtcca tgattatgac aagaactgcg attcgattca agtcagatgg    240

tttgcacgaa ttgaaaaagt ttgcggatac agagttctgg ctcagtttat cggagctgac    300

acgaaatttt ggctcaatat tttatcggac gatatgtttg gtttggcaaa cgccgcaatg    360

agtgatccca atatggataa aattgtatat gcttcgccgc ttgcaatcaa cgaagaatac    420

caaaatgata tggtaaatta tgtaaataat tgcattgatg gcgaaatcgt cggccaaact    480

tcgctgtctc caaaattcga tgaagggaag gctctcctaa gcaagcatcg tttcaaagtt    540

ggacaacgtc ttgaactatt aaattattcc aattctactg aaatacgcgt agcgcgaatt    600

caagaaatat gtggacgacg aatgaatgta tctatcacaa agaaagactt tcccgaatcg    660

cttccagatg cagatgacga cagacaagtc tttagctctg gatctcaata ttggatagac    720

gagggaagct tcttcatatt tcctgttgga tttgcagcag tcaatggata tcaactaaat    780

gcgaaaaagg aatatattga gcacacaaat aaaattgctc aagcaataaa aaatggagaa    840

aatccaagat atgactcaga cgacgtcaca tttgatcaat tagcaaaaga tccaattgat    900

cccatgattt ggagaaaagt taaggttgga caaaagtttg agctcatcga ccccttggct    960

cagcaattca ataacctcca cgtcgcttcg attctcaaat tttgcaaaac tgaaggatat   1020

cttattgtgg gaatggatgg tccagatgca cttgaagaca gttttcctat tcatatcaat   1080

aatacattta tgttcccagt tggttatgcg gaaaagtata atttggaact tgttccgcca   1140

gatgagttca aaggaacatt cagatgggat gaatacttgg agaaagaatc tgcagaaacc   1200

ctaccgcttg acttgttcaa gccaatgcct tcccaagaga gattagacaa atttaaggta   1260

attctgattt ccaaacgggt aggactacgc cttgaagctg ctgacatgtg tgaaaatcag   1320

tttatttgtc cagctacagt gaaatcagtt catggaagac tgataaatgt caatttcgac   1380

ggctgggatg aagaatttga tgaactgtat gatgtggact cccatgatat tctaccgata   1440

ggatggtgtg aagcgcacag ttatgttcta caacctccga aaaagtacaa ctattga      1497
```

<210> SEQ ID NO 76
<211> LENGTH: 2307
<212> TYPE: DNA
<213> ORGANISM: Caenorhabditis elegans -continued

<400> SEQUENCE: 76

```
atgctaaaat tagtcatttt gtgcttcgcg ttgttctaca atacagtcag ttcgacaaga      60
tttctgtttg gcgtcgaagt taagtgtgat tttgatgaag tgttccaatt aacagtgtcg     120
cattgggaag acgatggcaa tactttttgg gatcgcgatg aagacatcac tggacgtatg     180
actatgtttg ctcgaaagaa aatatttttc tatcaggacg gccatcatgg atttgaattt     240
ggaaagctcg agccttatgg gtggtttctg cacaattgca cgaaaaatgg aaattttcgc     300
gagtataggc acgggttgag tagcaccagt ggatccaatg ggttggagta tattgagtac     360
actgtgaatt tgacgaacgc ctgagaaata tcaaatcaaa tcgaactaac tttcaatttc     420
aataaacatt ctctctaatt acgttttaaa ccagtcttaa tttcagatgt ctgaatttct     480
gaaaattgtc agagctaaca aaaaatcgga cagaaaactc gataagacct acttgtggga     540
atcctattta catcagttcg agaaaggaaa aacttctttc attccagttg aagcattcaa     600
tcgtaacctt acagttaatt ttaacgaatg cgtgaaggaa ggagttatcg tgagttcata     660
ttgttcgtaa atcggtttta aaatacaatt tttgtagttc gaaacagtgg tccatgatta     720
tgacaagaac tgcgattcga ttcaagtcag atggtttgca cgaattgaaa aagtttgcgg     780
atacagagtt ctggctcagt ttatcggagc tgacacgaaa ttttggctca atattttatc     840
ggacgatatg tttggtttgg caaagtaagt tggacgctca gctctttcta ctattctaaa     900
taaataatgg ttctgttaca taaaattcta gagaacaatc gtattaaaac ttcgaaacat     960
ttgtataata gtaaaatttg aacatttcag cgccgcaatg agtgatccca atatggataa    1020
aattgtatat gctccgccgc ttgcaatcaa cgaagaatac caaaatgata tggtaaatta    1080
tgtaaatgta agtttgtttt tttccgaatt tatgttaata tcatctcaca acttcagaat    1140
tgcattgatg gcgaaatcgt cggccaaact tcgctgtctc caaaattcga tgaagggaag    1200
gctctcctaa gcaagcatcg tttcaaagtt ggacaacgtc ttgaactatt aaattattcc    1260
aattctactg aaatacgcgt agcgcgaatt caagaaatat gtggacgacg aatgaatgta    1320
tctatcacaa agaaagactt tcccgaatcg cttccagatg cagatgacga cagacaagtc    1380
tttagctctg gatctcaata ttggatagac gagggaagct tcttcatatt tcctgttgga    1440
tttgcagcag tcaatggata tcaactaaat gcgaaaaagg aatatattga gcacacaaat    1500
aaaattgctc aagcaataaa aaatggagaa aatccaagat atgactcaga cgacgtcaca    1560
tttgatcaat tagcaaaaga tccaattgat cccatgattt ggagaaaagt taaggttgga    1620
caaaagtttg agctcatcga ccccttggct cagcaattca ataacctcca cgtcgcttcg    1680
attctcaaat tttgcaaaac tgaaggatat cttattgtgg gaatggatgg tccagatgca    1740
cttgaagaca gttttcctat tcatatcaat aatacattta tgttcccagt tggttatgcg    1800
gaaaagtata atttggaact tgttccgcca gatgagttca aaggaacatt cagatgggat    1860
gaatacttgg agaaagaatc tgcagaaacc ctaccgcttg acttgttcaa gccaatgcct    1920
tcccaagaga gattagacaa atttaaggta attctgattt ccaaacgggt tgttttatat    1980
cgtttgagat tgtttcacta ttaatagtta ttcataattg tttcttgttt taaggtagga    2040
ctacgccttg aagctgctga catgtgtgaa aatcagttta tttgtccagc tacagtgaaa    2100
tcagttcatg gaagactgat aaatgtcaat ttcgacggct gggatgaaga atttgatgaa    2160
ctgtatgatg tggagtgagt ttatcatgac cgaacgacat tttttcaatg aaaattctat    2220
catttcagct cccatgatat tctaccgata ggatggtgtg aagcgcacag ttatgttcta    2280
caacctccga aaaagtacaa ctattga                                        2307
```

-continued

<210> SEQ ID NO 77
<211> LENGTH: 2307
<212> TYPE: DNA
<213> ORGANISM: Caenorhabditis elegans

<400> SEQUENCE: 77
atgctaaaat tagtcatttt gtgcttcgcg ttgttctaca atacagtcag ttcgacaaga 60
tttctgtttg gcgtcgaagt taagtgtgat tttgatgaag tgttccaatt aacagtgtcg 120
cattgggaag acgatggcaa tactttttgg gatcgcgatg aagacatcac tggacgtatg 180
actatgtttg ctcgaaagaa aatatttttc tatcaggacg gccatcatgg atttgaattt 240
ggaaagctcg agccttatgg gtggtttctg cacaattgca cgaaaaatgg aaattttcgc 300
gagtataggc acgggttgag tagcaccagt ggatccaatg ggttggagta tattgagtac 360
actgtgaatt tgacgaacgc ctgagaaata tcaaatcaaa tcgaactaac tttcaatttc 420
aataaacatt ctctctaatt acgttttaaa ccagtcttaa tttcagatgt ctgaatttct 480
gaaaattgtc agagctaaca aaaaatcgga cagaaaactc gataagacct acttgtggga 540
atcctattta catcagttcg agaaaggaaa aacttctttc attccagttg aagcattcaa 600
tcgtaacctt acagttaatt ttaacgaatg cgtgaaggaa ggagttatcg tgagttcata 660
ttgttcgtaa atcggtttta aaatacaatt tttgtagttc gaaacagtgg tccatgatta 720
tgacaagaac tgcgattcga ttcaagtcag atggtttgca cgaattgaaa aagtttgcgg 780
atacagagtt ctggctcagt ttatcggagc tgacacgaaa ttttggctca atattttatc 840
ggacgatatg tttggtttgg caaagtaagt tggacgctca gctctttcta ctattctaaa 900
taaataatgg ttctgttaca taaaattcta gagaacaatc gtattaaaac ttcgaaacat 960
ttgtataata gtaaaatttg aacatttcag cgccgcaatg agtgatccca atatggataa 1020
aattgtatat gctccgccgc ttgcaatcaa cgaagaatac caaaatgata tggtaaatta 1080
tgtaaatgta agtttgtttt tttccgaatt tatgttaata tcatctcaca acttcagaat 1140
tgcattgatg gcgaaatcgt cggccaaact tcgctgtctc caaaattcga tgaagggaag 1200
gctctcctaa gcaagcatcg tttcaaagtt ggacaacgtc ttgaactatt aaattattcc 1260
aattctactg aaatacgcgt agcgcgaatt caagaaatat gtggacgacg aatgaatgta 1320
tctatcacaa agaaagactt tcccgaatcg cttccagatg cagatgacga cagacaagtc 1380
tttagctctg gatctcaata ttggatagac gagggaagct tcttcatatt tcctgttgga 1440
tttgcagcag tcaatggata tcaactaaat gcgaaaaagg aatatattga gcacacaaat 1500
aaaattgctc aagcaataaa aaatggagaa aatccaagat atgactcaga cgacgtcaca 1560
tttgatcaat tagcaaaaga tccaattgat cccatgattt ggagaaaagt taaggttgga 1620
caaaagtttg agctcatcga cccccttggct cagcaattca ataacctcca cgtcgcttcg 1680
attctcaaat tttgcaaaac tgaaggatat cttattgtgg gaatggatgg tccagatgca 1740
cttgaagaca gttttcctat tcatatcaat aatacattta tgttcccagt tggttatgcg 1800
gaaaagtata atttggaact tgttccgcca gatgagttca aaggaacatt cagatgggat 1860
gaatacttgg agaaagaatc tgcagaaacc ctaccgcttg acttgttcaa gccaatgcct 1920
tcccaagaga gattagacaa atttaaggta attctgattt ccaaacgggt tgttttatat 1980
cgtttgagat tgtttcacta ttaatagtta ttcataattg tttcttgttt taaggtagga 2040
ctacgccttg aagctgctga catgtgtgaa aatcagttta tttgtccagc tacagtgaaa 2100
tcagttcatg gaagactgat aaatgtcaat ttcgacggct gggatgaaga atttgatgaa 2160

-continued ctgtatgatg tggagtgagt ttatcatgac cgaacgacat tttttcaatg aaaattctat 2220
catttcaact cccatgatat tctaccgata ggatggtgtg aagcgcacag ttatgttcta 2280
caacctccga aaaagtacaa ctattga 2307

<210> SEQ ID NO 78
<211> LENGTH: 2307
<212> TYPE: DNA
<213> ORGANISM: Caenorhabditis elegans

<400> SEQUENCE: 78
atgctaaaat tagtcatttt gtgcttcgcg ttgttctaca atacagtcag ttcgacaaga 60
tttctgtttg gcgtcgaagt taagtgtgat tttgatgaag tgttccaatt aacagtgtcg 120
cattgggaag acgatggcaa tactttttgg gatcgcgatg aagacatcac tggacgtatg 180
actatgtttg ctcgaaagaa aatatttttc tatcaggacg gccatcatgg atttgaattt 240
ggaaagctcg agccttatgg gtggtttctg cacaattgca cgaaaaaatgg aaattttcgc 300 gagtataggc acgggttgag tagcaccagt ggatccaatg ggttggagta tattgagtac 360
actgtgaatt tgacgaacgc ctgagaaata tcaaatcaaa tcgaactaac tttcaatttc 420
aataaacatt ctctctaatt acgttttaaa ccagtcttaa tttcagatgt ctgaatttct 480
gaaaattgtc agagctaaca aaaaatcgga cagaaaactc gataagacct acttgtggga 540
atcctattta catcagttcg agaaaggaaa aacttctttc attccagttg aagcattcaa 600
tcgtaacctt acagttaatt ttaacgaatg cgtgaaggaa ggagttatcg tgagttcata 660
ttgttcgtaa atcggtttta aaatacaatt tttgtagttc gaaacagtgg tccatgatta 720
tgacaagaac tgcgattcga ttcaagtcag atggtttgca cgaattgaaa aagtttgcgg 780
atacagagtt ctggctcagt ttatcggagc tgacacgaaa ttttggctca atattttatc 840
ggacgatatg tttggtttgg caaagtaagt tggacgctca gctctttcta ctattctaaa 900
taaataatgg ttctgttaca taaaattcta gagaacaatc gtattaaaac ttcgaaacat 960
ttgtataata gtaaaatttg aacatttcag cgccgcaatg agtgatccca atatggataa 1020
aattgtatat gctccgccgc ttgcaatcaa cgaagaatac caaaatgata tggtaaatta 1080
tgtaaatgta agtttgtttt tttccgaatt tatgttaata tcatctcaca acttcaaaat 1140
tgcattgatg gcgaaatcgt cggccaaact tcgctgtctc caaaattcga tgaagggaag 1200
gctctcctaa gcaagcatcg tttcaaagtt ggacaacgtc ttgaactatt aaattattcc 1260
aattctactg aaatacgcgt agcgcgaatt caagaaatat gtggacgacg aatgaatgta 1320
tctatcacaa agaaagactt tcccgaatcg cttccagatg cagatgacga cagacaagtc 1380
tttagctctg gatctcaata ttggatagac gagggaagct tcttcatatt tcctgttgga 1440
tttgcagcag tcaatggata tcaactaaat gcgaaaaagg aatatattga gcacacaaat 1500
aaaattgctc aagcaataaa aaatggagaa aatccaagat atgactcaga cgacgtcaca 1560
tttgatcaat tagcaaaaga tccaattgat cccatgattt ggagaaaagt taaggttgga 1620
caaaagtttg agctcatcga ccccttggct cagcaattca ataacctcca cgtcgcttcg 1680
attctcaaat tttgcaaaac tgaaggatat cttattgtgg gaatggatgg tccagatgca 1740
cttgaagaca gttttcctat tcatatcaat aatacattta tgttcccagt tggttatgcg 1800
gaaaagtata atttggaact tgttccgcca gatgagttca aaggaacatt cagatgggat 1860
gaatacttgg agaaagaatc tgcagaaacc ctaccgcttg acttgttcaa gccaatgcct 1920
tcccaagaga gattagacaa atttaaggta attctgattt ccaaacgggt tgttttatat 1980

-continued

```
cgtttgagat tgtttcacta ttaatagtta ttcataattg tttcttgttt taaggtagga   2040

ctacgccttg aagctgctga catgtgtgaa aatcagttta tttgtccagc tacagtgaaa   2100

tcagttcatg gaagactgat aaatgtcaat ttcgacggct gggatgaaga atttgatgaa   2160

ctgtatgatg tggagtgagt ttatcatgac cgaacgacat tttttcaatg aaaattctat   2220

catttcagct cccatgatat tctaccgata ggatggtgtg aagcgcacag ttatgttcta   2280

caacctccga aaaagtacaa ctattga                                       2307
```